(12) United States Patent
McAuley et al.

(10) Patent No.: US 12,714,817 B2
(45) Date of Patent: Aug. 25, 2026

(54) NASAL INTERFACE

(71) Applicant: Fisher & Paykel Healthcare Limited, Auckland (NZ)

(72) Inventors: Alastair Edwin McAuley, Auckland (NZ); Jason Peter van Beurden, Auckland (NZ); Craig Karl White, Auckland (NZ); Tristan Andrew Leslie, Auckland (NZ); Christopher Earl Nightingale, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/456,360

(22) Filed: Aug. 25, 2023

(65) Prior Publication Data

US 2024/0139454 A1 May 2, 2024

Related U.S. Application Data

(63) Continuation of application No. 16/514,126, filed on Jul. 17, 2019, now abandoned, which is a (Continued)

(51) Int. Cl.
*A61M 16/06* (2006.01)
*A61M 16/00* (2006.01)
(Continued)

(52) U.S. Cl.
CPC .... *A61M 16/0666* (2013.01); *A61M 16/0069* (2014.02); *A61M 16/06* (2013.01); (Continued)

(58) Field of Classification Search
CPC .............. A61M 16/06; A61M 16/0666; A61M 16/0683; A61M 16/0616; A61M 16/0875
See application file for complete search history.

(56) References Cited

U.S. PATENT DOCUMENTS 301,111 A 7/1884 Genese
472,238 A 4/1892 Van Orden
(Continued)

FOREIGN PATENT DOCUMENTS

AU 2009321054 7/2015
CA 1311662 12/1992
(Continued)

OTHER PUBLICATIONS

MatWeb Material Property Data, “Overview of Materials for Polycarbonate, Molded”, https://www.matweb.com/search/DataSheet.aspx?MatGUID=84b257896b674f93a39596d00d999d77, accessed May 1, 2024 (Year: 2024).*
(Continued)

*Primary Examiner* — Douglas Y Sul
(74) *Attorney, Agent, or Firm* — VIA LLP

(57) ABSTRACT

A nasal cannula for use in a system for providing a flow of respiratory gases to a user is described. The nasal cannula comprises a body made from a pliable material. The body has an inlet and at least one nasal prong fluidly connected to the inlet. In use a conduit providing a flow of gases to the cannula is connected to the inlet, and the nasal prong is inserted into a user's nostril. The cannula is arranged to direct the flow of gases from the nasal prong towards the front wall of the user's nasal passage within the user's nose.

20 Claims, 19 Drawing Sheets

Related U.S. Application Data continuation of application No. 15/946,391, filed on Apr. 5, 2018, now Pat. No. 10,384,029, which is a continuation of application No. 15/425,145, filed on Feb. 6, 2017, now Pat. No. 10,821,251, which is a continuation of application No. 15/078,970, filed on Mar. 23, 2016, now Pat. No. 9,561,339, which is a continuation of application No. 13/510,468, filed as application No. PCT/NZ2010/000229 on Nov. 16, 2010, now Pat. No. 10,137,271.

(60) Provisional application No. 61/262,297, filed on Nov. 18, 2009.

(51) Int. Cl.
*A61M 16/08* (2006.01)
*A61M 16/10* (2006.01)
*A61M 16/16* (2006.01)

(52) U.S. Cl.
CPC .... *A61M 16/0616* (2014.02); *A61M 16/0683* (2013.01); *A61M 16/0816* (2013.01); *A61M 16/0825* (2014.02); *A61M 16/085* (2014.02); *A61M 16/0866* (2014.02); *A61M 16/0875* (2013.01); *A61M 16/105* (2013.01); *A61M 16/109* (2014.02); *A61M 16/1095* (2014.02); *A61M 16/16* (2013.01); *A61M 16/161* (2014.02); *A61M 2205/3368* (2013.01); *A61M 2205/3653* (2013.01); *A61M 2205/42* (2013.01); *A61M 2205/502* (2013.01); *A61M 2210/0618* (2013.01)

(56) References Cited

U.S. PATENT DOCUMENTS 577,926 A 3/1897 Miller
718,470 A 1/1903 Jones
751,091 A 2/1904 Moran
770,013 A 9/1904 Linn
1,635,545 A 7/1927 Drager
2,126,755 A 8/1938 Dreyfus
2,228,218 A 1/1941 Schwartz
2,241,535 A 5/1941 Boothby et al.
2,296,150 A 9/1942 Dockson et al.
2,353,643 A 7/1944 Bulbulian
2,359,506 A 10/1944 Battley et al.
2,388,604 A 11/1945 Eisenbud
2,415,846 A 2/1947 Francis
2,452,845 A 11/1948 Fisher
2,508,050 A 5/1950 Valente
2,684,066 A 7/1954 Glidden
2,693,800 A 11/1954 Caldwell
2,738,788 A 3/1956 Matheson et al.
2,749,910 A 6/1956 Faulconer
2,837,090 A 6/1958 Bloom
2,843,121 A 7/1958 Hudson
2,859,748 A 11/1958 Hudson
2,875,759 A 3/1959 Galleher
2,894,506 A 7/1959 Rose
2,939,458 A 6/1960 Lundquist
3,234,940 A 2/1966 Morton
3,330,273 A 7/1967 Ray
3,424,633 A 1/1969 Corrigall et al.
3,490,452 A 1/1970 Greenfield
3,545,437 A 12/1970 Quackenbush
3,599,635 A 8/1971 Kenneth
3,682,171 A 8/1972 Dali et al.
3,834,682 A 9/1974 McPhee
3,850,171 A 11/1974 Ball et al.
3,894,562 A 7/1975 Mosley et al.
3,972,321 A 8/1976 Proctor
3,977,432 A 8/1976 Vidal
3,982,532 A 9/1976 Halldin et al.
3,992,720 A 11/1976 Nicolinas
4,090,510 A 5/1978 Segersten
D250,047 S 10/1978 Lewis et al.
D250,131 S 10/1978 Lewis et al.
4,127,130 A 11/1978 Naysmith
4,150,464 A 4/1979 Tracy
D252,322 S 7/1979 Johnson
4,201,205 A 5/1980 Bartholomew
4,258,710 A 3/1981 Reber
4,266,540 A 5/1981 Panzik et al.
4,278,082 A 7/1981 Blackmer
4,354,488 A 10/1982 Bartos
4,367,735 A 1/1983 Dali
4,378,011 A 3/1983 Warncke et al.
4,437,462 A 3/1984 Piljay
4,454,880 A 6/1984 Muto et al.
4,574,799 A 3/1986 Warncke et al.
4,603,602 A 8/1986 Montesi
4,621,632 A 11/1986 Bartels et al.
4,644,974 A 2/1987 Zingg
4,676,241 A 6/1987 Webb et al.
4,677,977 A 7/1987 Wilcox
D293,613 S 1/1988 Wingler
4,753,233 A 6/1988 Grimes
4,773,411 A 9/1988 Downs
4,782,832 A 11/1988 Trimble et al.
4,803,981 A 2/1989 Vickery
4,804,160 A 2/1989 Harbeke
4,836,200 A 6/1989 Clark et al.
4,856,508 A 8/1989 Tayebi
4,907,584 A 3/1990 McGinnis
4,915,104 A 4/1990 Marcy
4,915,105 A 4/1990 Lee
4,919,128 A 4/1990 Kopala et al.
4,938,209 A 7/1990 Fry
4,941,467 A 7/1990 Takata
4,944,310 A 7/1990 Sullivan
D310,431 S 9/1990 Bellm
4,958,658 A 9/1990 Zajac
4,971,051 A 11/1990 Toffolon
4,986,269 A 1/1991 Hakkinen
5,010,925 A 4/1991 Atkinson et al.
5,016,625 A 5/1991 Hsu et al.
5,031,261 A 7/1991 Fenner
5,042,478 A 8/1991 Kopala et al.
5,046,491 A 9/1991 Derrick
D320,677 S 10/1991 Kumagai et al.
D321,419 S 11/1991 Wallace
5,062,421 A 11/1991 Burns et al.
5,065,756 A 11/1991 Rapoport
D322,318 S 12/1991 Sullivan et al.
5,074,297 A 12/1991 Venegas
5,094,236 A 3/1992 Tayebi
5,113,857 A 5/1992 Dickerman et al.
5,121,745 A 6/1992 Israel et al.
5,148,802 A 9/1992 Sanders et al.
5,164,652 A 11/1992 Johnson et al.
5,231,979 A 8/1993 Rose
5,243,971 A 9/1993 Sullivan et al.
5,245,995 A 9/1993 Sullivan et al.
D340,317 S 10/1993 Cole
5,259,377 A 11/1993 Schroeder
5,267,556 A 12/1993 Feng
5,269,296 A 12/1993 Landis et al.
5,315,859 A 5/1994 Schommer
5,349,949 A 9/1994 Schegerin
5,353,789 A 10/1994 Schobohm
5,366,805 A 11/1994 Fujiki et al.
D354,128 S 1/1995 Rinehart
D355,484 S 2/1995 Rinehart
5,400,776 A 3/1995 Bartholomew
5,429,683 A 7/1995 Le Mitouard
5,438,979 A 8/1995 Johnson et al.
5,441,046 A 8/1995 Starr et al.
5,449,206 A 9/1995 Lockwood
5,449,234 A 9/1995 Gipp et al.
5,458,202 A 10/1995 Fellows et al.
5,460,174 A 10/1995 Chang

(56) References Cited

U.S. PATENT DOCUMENTS 5,461,932 A 10/1995 Hall
5,477,852 A 12/1995 Landis et al.
5,513,634 A 5/1996 Jackson
5,518,802 A 5/1996 Colvin et al.
5,533,506 A 7/1996 Wood
5,540,223 A 7/1996 Starr et al.
5,542,128 A 8/1996 Lomas
5,551,419 A 9/1996 Froehlich et al.
5,558,090 A 9/1996 James
5,560,354 A 10/1996 Berthon-Jones et al.
5,570,689 A 11/1996 Starr et al.
5,588,423 A 12/1996 Smith
5,595,174 A 1/1997 Gwaltney
5,601,078 A 2/1997 Schaller et al.
D378,610 S 3/1997 Reischel et al.
5,649,532 A 7/1997 Griffiths
5,657,752 A 8/1997 Landis et al.
5,662,101 A 9/1997 Ogden et al.
5,664,566 A 9/1997 Mcdonald et al.
5,687,715 A 11/1997 Landis
5,690,097 A 11/1997 Howard et al.
5,724,677 A 3/1998 Bryant et al.
5,724,965 A 3/1998 Handke et al.
5,746,201 A 5/1998 Kidd
5,752,510 A 5/1998 Goldstein
5,755,578 A 5/1998 Contant et al.
5,789,660 A 8/1998 Kofoed et al.
5,806,727 A 9/1998 Joseph
5,807,295 A 9/1998 Hutcheon et al.
5,857,460 A 1/1999 Popitz
5,884,624 A 3/1999 Barnett et al.
5,904,278 A 5/1999 Barlow et al.
5,918,598 A 7/1999 Belfer
5,921,239 A 7/1999 McCall et al.
5,924,420 A 7/1999 Reischel
5,941,245 A 8/1999 Hannah et al.
5,943,473 A 8/1999 Levine
5,953,763 A 9/1999 Gouget
5,966,745 A 10/1999 Schwartz et al.
6,016,804 A 1/2000 Gleason et al.
6,017,315 A 1/2000 Starr et al.
6,019,101 A 2/2000 Cotner et al.
6,021,528 A 2/2000 Jurga
6,039,044 A 3/2000 Sullivan
6,050,260 A 4/2000 Daniell et al.
6,112,746 A 9/2000 Kwok et al.
6,116,235 A 9/2000 Walters et al.
6,119,693 A 9/2000 Kwok et al.
6,119,694 A 9/2000 Correa et al.
6,127,071 A 10/2000 Lu
6,135,109 A 10/2000 Blasdell et al.
6,135,432 A 10/2000 Hebblewhite et al.
6,192,886 B1 2/2001 Rudolph
D440,302 S 4/2001 Wolfe
6,272,933 B1 8/2001 Gradon et al.
6,298,850 B1 10/2001 Argraves
6,302,105 B1 10/2001 Wickham et al.
6,341,606 B1 1/2002 Bordewick et al.
6,347,631 B1 2/2002 Hansen et al.
6,354,293 B1 3/2002 Madison
D455,891 S 4/2002 Biedrzycki
6,398,197 B1 6/2002 Dickinson et al.
6,412,487 B1 7/2002 Gunaratnam et al.
6,412,488 B1 7/2002 Barnett
6,418,928 B1 7/2002 Bordewick et al.
6,418,929 B1 7/2002 Norfleet
6,422,238 B1 7/2002 Lithgow
6,427,694 B1 8/2002 Hecker et al.
6,431,172 B1 8/2002 Bordewick
6,435,181 B1 8/2002 Jones, Jr. et al.
6,439,234 B1 8/2002 Curti et al.
6,457,473 B1 10/2002 Brostrom et al.
6,467,483 B1 10/2002 Kopacko et al.
6,470,886 B1 10/2002 Jestrabek-Hart
6,478,026 B1 11/2002 Wood
6,484,725 B1 11/2002 Chi et al.
6,488,664 B1 12/2002 Solomon et al.
6,491,034 B1 12/2002 Gunaratnam et al.
6,513,526 B2 2/2003 Kwok et al.
6,526,978 B2 3/2003 Dominguez
6,530,373 B1 3/2003 Patron et al.
6,561,188 B1 5/2003 Ellis
6,561,190 B1 5/2003 Kwok
6,561,191 B1 5/2003 Kwok
6,571,798 B1 6/2003 Thornton
6,581,594 B1 6/2003 Drew et al.
6,581,601 B2 6/2003 Ziaee
6,581,602 B2 6/2003 Kwok et al.
6,584,977 B1 7/2003 Serowski
6,588,424 B2 7/2003 Bardel
6,615,832 B1 9/2003 Chen
6,629,531 B2 10/2003 Gleason et al.
6,631,718 B1 10/2003 Lovell
6,634,358 B2 10/2003 Kwok et al.
6,637,434 B2 10/2003 Noble
6,644,315 B2 11/2003 Ziaee
6,651,658 B1 11/2003 Hill et al.
6,651,663 B2 11/2003 Barnett et al.
6,659,102 B1 12/2003 Sico
6,662,803 B2 12/2003 Gradon et al.
6,668,828 B1 12/2003 Figley et al.
D485,905 S 1/2004 Moore
6,679,257 B1 1/2004 Robertson et al.
6,679,265 B2 1/2004 Strickland et al.
6,691,707 B1 2/2004 Gunaratnam et al.
6,712,072 B1 3/2004 Lang
6,736,139 B1 5/2004 Wix
6,769,432 B1 8/2004 Keifer
6,772,760 B2 8/2004 Frater et al.
6,772,761 B1 8/2004 Rucker, Jr.
6,796,308 B2 9/2004 Gunaratnam et al.
6,817,362 B2 11/2004 Gelinas et al.
6,823,869 B2 11/2004 Raje et al.
6,851,425 B2 2/2005 Jaffre et al.
6,851,428 B2 2/2005 Dennis
6,883,177 B1 4/2005 Ouellette et al.
6,892,729 B2 5/2005 Smith et al.
6,895,965 B2 5/2005 Scarberry et al.
6,907,882 B2 6/2005 Ging et al.
6,918,390 B2 7/2005 Lithgow et al.
6,951,218 B2 10/2005 Gradon et al.
6,953,354 B2 10/2005 Edirisuriya et al.
6,997,187 B2 2/2006 Wood et al.
7,004,165 B1 2/2006 Salcido
7,007,696 B2 3/2006 Palkon et al.
7,021,311 B2 4/2006 Gunaratnam et al.
D520,140 S 5/2006 Chaggares
7,051,765 B1 5/2006 Kelley et al.
7,066,179 B2 6/2006 Eaton et al.
7,077,126 B2 7/2006 Kummer et al.
D526,094 S 8/2006 Chen
7,096,864 B1 8/2006 Mayer et al.
D533,269 S 12/2006 McAuley et al.
7,178,525 B2 2/2007 Matula, Jr. et al.
7,178,528 B2 2/2007 Lau
7,201,169 B2 4/2007 Wilkie et al.
7,207,333 B2 4/2007 Tohara
7,210,481 B1 5/2007 Lovell et al.
7,219,669 B1 5/2007 Lovell et al.
7,225,811 B2 6/2007 Ruiz et al.
7,255,106 B2 8/2007 Gallem et al.
7,261,104 B2 8/2007 Keifer
7,287,528 B2 10/2007 Ho et al.
7,290,546 B2 11/2007 Sprinkle et al.
7,296,575 B1 11/2007 Radney
7,318,437 B2 1/2008 Gunaratnam et al.
7,353,827 B2 4/2008 Geist
7,357,136 B2 4/2008 Ho et al.
7,406,966 B2 8/2008 Wondka et al.
7,448,386 B2 11/2008 Ho et al.
7,487,772 B2 2/2009 Ging et al.
7,493,902 B2 2/2009 White et al.
D589,139 S 3/2009 Guney
7,523,754 B2 4/2009 Lithgow et al.

(56) References Cited

U.S. PATENT DOCUMENTS 7,549,420 B2 6/2009 Martinez et al.
D595,841 S 7/2009 McAuley et al.
7,562,658 B2 7/2009 Madaus et al.
7,597,100 B2 10/2009 Ging
7,640,934 B2 1/2010 Zollinger et al.
7,647,926 B2 1/2010 Gerder et al.
7,658,189 B2 2/2010 Davidson et al.
7,665,464 B2 2/2010 Kopacko et al.
D612,933 S 3/2010 Prentice
7,681,575 B2 3/2010 Wixey et al.
7,694,677 B2 4/2010 Tang
7,703,457 B2 4/2010 Barnett et al.
7,708,017 B2 5/2010 Davidson
7,753,051 B2 7/2010 Burrow et al.
D623,288 S 9/2010 Lubke
7,814,911 B2 10/2010 Bordewick et al.
7,827,990 B1 11/2010 Melidis et al.
7,828,990 B1 11/2010 Melidis
7,856,982 B2 12/2010 Matula et al.
7,861,715 B2 1/2011 Jones et al.
7,877,817 B1 2/2011 Ho
7,896,003 B2 3/2011 Matula et al.
7,931,024 B2 4/2011 Ho et al.
7,934,501 B2 5/2011 Fu
7,942,150 B2 5/2011 Guney et al.
7,992,560 B2 8/2011 Burton et al.
8,042,539 B2 10/2011 Chandran et al.
8,042,541 B2 10/2011 Amarasinghe et al.
8,109,271 B2 2/2012 Vandine et al.
8,136,524 B2 3/2012 Ging et al.
8,136,525 B2 3/2012 Lubke et al.
8,171,933 B2 5/2012 Xue et al.
D661,796 S 6/2012 Andrews et al.
8,245,711 B2 8/2012 Matula et al.
8,272,382 B2 9/2012 Howard et al.
8,371,302 B2 2/2013 Ging et al.
8,397,727 B2 3/2013 Ng et al.
8,443,807 B2 5/2013 McAuley et al.
D686,313 S 7/2013 Matula et al.
8,479,726 B2 7/2013 McAuley
8,479,741 B2 7/2013 McAuley et al.
8,567,404 B2 10/2013 Davidson et al.
8,631,793 B2 1/2014 Omura et al.
8,631,799 B2 1/2014 Davenport
8,636,005 B2 1/2014 Gradon et al.
8,701,667 B1 * 4/2014 Ho .................... A61M 16/0605 128/207.18
8,714,157 B2 5/2014 McAuley et al.
8,720,444 B2 5/2014 Chang
8,757,157 B2 6/2014 Price et al.
8,783,257 B2 7/2014 McAuley et al.
8,869,797 B2 10/2014 Davidson et al.
8,869,798 B2 10/2014 Wells et al.
8,875,709 B2 11/2014 Davidson et al.
8,944,061 B2 2/2015 D'Souza et al.
8,950,404 B2 2/2015 Formica et al.
8,960,196 B2 2/2015 Henry
9,010,331 B2 4/2015 Lang et al.
9,027,556 B2 5/2015 Ng et al.
9,032,955 B2 5/2015 Lubke et al.
9,032,956 B2 5/2015 Scheiner et al.
9,072,852 B2 7/2015 McAuley et al.
9,095,673 B2 8/2015 Barlow et al.
9,119,929 B2 9/2015 McAuley et al.
9,119,931 B2 9/2015 D'Souza et al.
9,138,555 B2 9/2015 McAuley et al.
9,149,596 B2 10/2015 Valcic et al.
9,186,474 B1 11/2015 Rollins
9,242,062 B2 1/2016 Melidis et al.
9,292,799 B2 3/2016 McAuley et al.
9,295,799 B2 3/2016 McAuley et al.
9,302,065 B2 4/2016 Smith et al.
9,320,566 B1 4/2016 Alston, Jr.
9,320,866 B2 4/2016 McAuley et al.
9,333,315 B2 5/2016 McAuley et al.
9,339,622 B2 5/2016 McAuley et al.
9,339,624 B2 5/2016 McAuley
9,375,545 B2 6/2016 Darkin et al.
9,381,316 B2 7/2016 Ng et al.
9,457,162 B2 10/2016 Ging et al.
9,486,601 B2 11/2016 Stallard et al.
9,517,317 B2 12/2016 McAuley et al.
9,522,246 B2 12/2016 Frater et al.
9,539,405 B2 1/2017 McAuley et al.
9,550,038 B2 1/2017 McAuley et al.
9,561,338 B2 2/2017 McAuley et al.
9,561,339 B2 2/2017 McAuley et al.
9,744,385 B2 8/2017 Henry et al.
9,884,160 B2 2/2018 Mcauley et al.
9,901,699 B2 2/2018 Veliss et al.
9,901,700 B2 2/2018 McAuley et al.
9,907,925 B2 3/2018 McAuley et al.
9,974,914 B2 5/2018 McAuley
10,080,856 B2 9/2018 McLaren et al.
10,137,271 B2 11/2018 McAuley et al.
10,201,678 B2 2/2019 Guney et al.
10,252,015 B2 4/2019 McAuley et al.
10,258,756 B2 4/2019 Mainusch et al.
10,258,757 B2 4/2019 Allan et al.
10,272,218 B2 4/2019 McAuley et al.
10,328,226 B2 6/2019 Allan et al.
10,363,387 B2 7/2019 Allan et al.
10,384,029 B2 8/2019 McAuley et al.
10,413,694 B2 9/2019 Allan et al.
10,463,825 B2 11/2019 McAuley et al.
10,792,451 B2 10/2020 Allan et al.
10,821,251 B2 11/2020 McAuley et al.
10,835,702 B2 11/2020 McAuley et al.
10,842,964 B2 11/2020 McAuley et al.
10,980,962 B2 4/2021 McAuley et al.
11,179,535 B2 11/2021 McAuley et al.
11,247,013 B2 2/2022 McAuley et al.
11,260,194 B2 3/2022 McAuley et al.
11,291,790 B2 4/2022 McAuley et al.
11,357,944 B2 6/2022 McAuley et al.
11,395,894 B2 7/2022 McAuley et al.
11,471,635 B2 10/2022 McAuley et al.
11,541,197 B2 1/2023 McAuley et al.
11,554,234 B2 1/2023 McAuley et al.
11,559,650 B2 1/2023 McAuley et al.
11,660,413 B2 5/2023 McAuley et al.
11,712,532 B2 8/2023 McAuley et al.
11,766,535 B2 9/2023 McAuley et al.
2001/0017134 A1 8/2001 Bahr
2001/0020474 A1 9/2001 Hecker et al.
2001/0029952 A1 10/2001 Curran
2002/0005198 A1 1/2002 Kwok et al.
2002/0014241 A1 2/2002 Gradon et al.
2002/0020416 A1 2/2002 Namey
2002/0026934 A1 3/2002 Lithgow et al.
2002/0029780 A1 3/2002 Frater et al.
2002/0039867 A1 4/2002 Curro et al.
2002/0046755 A1 4/2002 Voss
2002/0053347 A1 5/2002 Ziaee
2002/0059935 A1 5/2002 Wood
2002/0069467 A1 6/2002 Immediato et al.
2002/0092527 A1 7/2002 Wood
2002/0096173 A1 7/2002 Berthon-Jones
2002/0096176 A1 7/2002 Gunaratnam et al.
2002/0096178 A1 7/2002 Ziaee
2002/0100474 A1 8/2002 Kellner et al.
2002/0100479 A1 8/2002 Scarberry et al.
2002/0108613 A1 8/2002 Gunaratnam et al.
2002/0117177 A1 8/2002 Kwok
2003/0000533 A1 1/2003 Olsen et al.
2003/0005509 A1 1/2003 Kelzer
2003/0005931 A1 1/2003 Jaffre et al.
2003/0005933 A1 1/2003 Izuchukwu
2003/0019495 A1 1/2003 Palkon et al.
2003/0019496 A1 1/2003 Kopacko et al.
2003/0029454 A1 2/2003 Gelinas et al.
2003/0047185 A1 3/2003 Olsen et al.
2003/0051732 A1 3/2003 Smith et al.
2003/0075180 A1 4/2003 Raje

(56) References Cited

U.S. PATENT DOCUMENTS

2003/0075182 A1 4/2003 Heidmann et al.
2003/0079749 A1 5/2003 Strickland et al.
2003/0084996 A1 5/2003 Alberg et al.
2003/0089373 A1 5/2003 Gradon et al.
2003/0094177 A1 5/2003 Smith et al.
2003/0121519 A1 7/2003 Estes et al.
2003/0145857 A1 8/2003 Sullivan et al.
2003/0149384 A1 8/2003 Davis et al.
2003/0164170 A1 9/2003 Drew et al.
2003/0172936 A1 9/2003 Wilkie et al.
2003/0196655 A1 10/2003 Ging et al.
2003/0196656 A1 10/2003 Moore
2003/0196658 A1* 10/2003 Ging ................ A61M 16/0666 128/201.22
2003/0196659 A1 10/2003 Gradon et al.
2003/0196664 A1 10/2003 Jacobson
2003/0200970 A1 10/2003 Stenzler et al.
2003/0217746 A1 11/2003 Gradon et al.
2003/0221691 A1 12/2003 Biener
2004/0011087 A1 1/2004 Rebouillat et al.
2004/0025882 A1 2/2004 Madaus et al.
2004/0035427 A1 2/2004 Bordewick et al.
2004/0065328 A1 4/2004 Amarasinghe et al.
2004/0067333 A1 4/2004 Amarasinghe
2004/0092999 A1 5/2004 Lojewski
2004/0094157 A1 5/2004 Dantanarayana et al.
2004/0107968 A1 6/2004 Griffiths
2004/0112377 A1 6/2004 Amarasinghe et al.
2004/0112384 A1 6/2004 Lithgow et al.
2004/0112385 A1 6/2004 Drew
2004/0113406 A1 6/2004 Elqadah
2004/0118212 A1 6/2004 Orr et al.
2004/0118406 A1 6/2004 Lithgow
2004/0118412 A1 6/2004 Piletti-Reyes
2004/0133604 A1 7/2004 Ging
2004/0139973 A1 7/2004 Wright
2004/0149280 A1 8/2004 Semeniuk
2004/0182398 A1 9/2004 Sprinkle et al.
2004/0211427 A1 10/2004 Jones et al.
2004/0221850 A1 11/2004 Ging et al.
2004/0226566 A1 11/2004 Gunaratnam et al.
2004/0255949 A1 12/2004 Lang et al.
2004/0261797 A1* 12/2004 White ............... A61M 16/0003 128/206.11
2005/0011521 A1 1/2005 Sprinkle et al.
2005/0011524 A1* 1/2005 Thomlinson ...... A61M 16/0825 128/207.18
2005/0016532 A1 1/2005 Farrell
2005/0016544 A1 1/2005 Thornton
2005/0028822 A1 2/2005 Sleeper et al.
2005/0028833 A1 2/2005 Vena et al.
2005/0033247 A1 2/2005 Thompson
2005/0045182 A1 3/2005 Wood et al.
2005/0051171 A1 3/2005 Booth
2005/0051177 A1 3/2005 Wood
2005/0066976 A1 3/2005 Wondka
2005/0076913 A1 4/2005 Ho et al.
2005/0092327 A1 5/2005 Fini et al.
2005/0098183 A1 5/2005 Nash et al.
2005/0121030 A1 6/2005 Bateman et al.
2005/0121037 A1 6/2005 Wood
2005/0133038 A1 6/2005 Rutter
2005/0150497 A1 7/2005 Eifler et al.
2005/0155604 A1 7/2005 Ging et al.
2005/0172969 A1 8/2005 Ging
2005/0199239 A1 9/2005 Lang et al.
2005/0199241 A1 9/2005 Ging et al.
2005/0199242 A1 9/2005 Matula et al.
2005/0205096 A1 9/2005 Matula
2005/0235999 A1 10/2005 Wood et al.
2005/0241644 A1 11/2005 Guney et al.
2006/0027237 A1 2/2006 Sleeper
2006/0032504 A1 2/2006 Burton et al.
2006/0042629 A1 3/2006 Geist
2006/0042632 A1 3/2006 Bishop et al.
2006/0054169 A1 3/2006 Han et al.
2006/0060200 A1 3/2006 Ho et al.
2006/0076019 A1 4/2006 Ho
2006/0081250 A1 4/2006 Bordewick et al.
2006/0081256 A1 4/2006 Palmer
2006/0096598 A1 5/2006 Ho et al.
2006/0102185 A1 5/2006 Drew et al.
2006/0107958 A1 5/2006 Sleeper
2006/0118117 A1 6/2006 Berthon-Jones et al.
2006/0124131 A1 6/2006 Chandran
2006/0130844 A1 6/2006 Ho et al.
2006/0137690 A1 6/2006 Gunaratnam et al.
2006/0169286 A1 8/2006 Eifler et al.
2006/0174887 A1 8/2006 Chandran et al.
2006/0178645 A1 8/2006 Peppel
2006/0196511 A1 9/2006 Lau et al.
2006/0201514 A1 9/2006 Jones et al.
2006/0207599 A1 9/2006 Busch
2006/0213516 A1 9/2006 Hoffman
2006/0225740 A1 10/2006 Eaton et al.
2006/0231103 A1 10/2006 Matula et al.
2006/0237017 A1 10/2006 Davidson et al.
2006/0237018 A1 10/2006 McAuley et al.
2006/0249159 A1 11/2006 Ho
2006/0254593 A1 11/2006 Chang
2006/0266361 A1 11/2006 Hernandez
2006/0283456 A1 12/2006 Geiselhart et al.
2006/0283458 A1 12/2006 Woodard
2006/0283459 A1 12/2006 Geiselhart et al.
2006/0283461 A1 12/2006 Lubke et al.
2007/0000492 A1 1/2007 Hansel et al.
2007/0010786 A1 1/2007 Casey et al.
2007/0044804 A1 3/2007 Matula et al.
2007/0062536 A1 3/2007 McAuley
2007/0089749 A1 4/2007 Ho et al.
2007/0107733 A1 5/2007 Ho
2007/0107737 A1* 5/2007 Landis ............. A61M 16/0666 128/207.18
2007/0125384 A1 6/2007 Zollinger et al.
2007/0125385 A1 6/2007 Ho et al.
2007/0125387 A1 6/2007 Zollinger et al.
2007/0137653 A1 6/2007 Wood
2007/0142785 A1 6/2007 Lundgaard et al.
2007/0157353 A1 7/2007 Guney et al.
2007/0163594 A1 7/2007 Ho et al.
2007/0163600 A1 7/2007 Hoffman
2007/0174952 A1 8/2007 Jacob
2007/0175480 A1 8/2007 Gradon et al.
2007/0209663 A1 9/2007 Marque et al.
2007/0215158 A1 9/2007 Kroupa et al.
2007/0215161 A1 9/2007 Frater et al.
2007/0221227 A1 9/2007 Ho
2007/0227541 A1 10/2007 Van Den
2007/0267022 A1 11/2007 Chiam
2007/0272247 A1 11/2007 Porat
2007/0272249 A1 11/2007 Chandran
2007/0295335 A1 12/2007 Nashed
2008/0035152 A1 2/2008 Ho et al.
2008/0041388 A1 2/2008 McAuley et al.
2008/0041393 A1 2/2008 Bracken
2008/0047560 A1 2/2008 Veliss et al.
2008/0053446 A1 3/2008 Sleeper et al.
2008/0053450 A1 3/2008 Van Kerkwyk et al.
2008/0060648 A1 3/2008 Thornton et al.
2008/0060653 A1 3/2008 Hallett et al.
2008/0060657 A1 3/2008 McAuley et al.
2008/0066745 A1 3/2008 Janbakhsh
2008/0066755 A1 3/2008 Janbakhsh
2008/0078387 A1 4/2008 Vandine
2008/0078396 A1 4/2008 Janbakhsh
2008/0083412 A1 4/2008 Henry et al.
2008/0092905 A1 4/2008 Gunaratnam
2008/0099024 A1 5/2008 Gunaratnam et al.
2008/0105257 A1 5/2008 Klasek et al.
2008/0110464 A1 5/2008 Davidson et al.
2008/0127978 A1 6/2008 Rubin et al.
2008/0135050 A1 6/2008 Hitchcock et al.
2008/0142019 A1 6/2008 Lewis
2008/0149104 A1 6/2008 Eifler

(56) References Cited

U.S. PATENT DOCUMENTS

2008/0171737 A1 7/2008 Fensome
2008/0178875 A1 7/2008 Henry
2008/0178886 A1 7/2008 Lieberman et al.
2008/0190432 A1 8/2008 Blochlinger et al.
2008/0190436 A1 8/2008 Jaffe et al.
2008/0196728 A1 8/2008 Ho
2008/0210241 A1 9/2008 Schulz et al.
2008/0223370 A1 9/2008 Kim
2008/0230068 A1 9/2008 Rudolph
2008/0236586 A1 10/2008 Mcdonald et al.
2008/0245369 A1 10/2008 Matula et al.
2008/0257354 A1 10/2008 Davidson
2008/0264422 A1 10/2008 Fishman
2008/0271739 A1 11/2008 Facer et al.
2008/0276937 A1 11/2008 Davidson et al.
2008/0302366 A1 12/2008 McGinnis et al.
2008/0314388 A1 12/2008 Brambilla et al.
2008/0314390 A1 12/2008 Kwok et al.
2008/0319334 A1 12/2008 Yamamori
2009/0014007 A1 1/2009 Brambilla et al.
2009/0032024 A1 2/2009 Burz et al.
2009/0044808 A1* 2/2009 Guney .............. A61M 16/0875 128/207.18
2009/0078267 A1 3/2009 Burz et al.
2009/0090364 A1 4/2009 Daugaard et al.
2009/0107504 A1 4/2009 McAuley et al.
2009/0114227 A1 5/2009 Gunaratnam et al.
2009/0120442 A1 5/2009 Ho
2009/0126739 A1 5/2009 Ng et al.
2009/0133697 A1 5/2009 Kwok et al.
2009/0139527 A1 6/2009 Ng et al.
2009/0145429 A1 6/2009 Ging et al.
2009/0151729 A1 6/2009 Judson et al.
2009/0173349 A1 7/2009 Hernandez et al.
2009/0183734 A1 7/2009 Kwok et al.
2009/0183739 A1 7/2009 Wondka
2009/0188507 A1 7/2009 Lacava
2009/0211583 A1 8/2009 Carroll et al.
2009/0223519 A1 9/2009 Eifler et al.
2009/0223521 A1 9/2009 Howard
2009/0223523 A1* 9/2009 Chang ............... A61M 16/0616 128/207.11
2009/0320842 A1 12/2009 Doherty
2009/0320851 A1 12/2009 Selvarajan et al.
2010/0000538 A1 1/2010 Edwards et al.
2010/0000539 A1 1/2010 Woodard
2010/0000543 A1 1/2010 Berthon-Jones et al.
2010/0037897 A1 2/2010 Wood
2010/0051031 A1 3/2010 Lustenberger et al.
2010/0051034 A1 3/2010 Howard
2010/0083969 A1 4/2010 Crumblin
2010/0108072 A1 5/2010 D'Souza
2010/0132717 A1 6/2010 Davidson et al.
2010/0154798 A1 6/2010 Henry et al.
2010/0170516 A1 7/2010 Grane
2010/0192957 A1* 8/2010 Hobson ............ A61M 16/0672 128/207.18
2010/0199992 A1 8/2010 Ho
2010/0229868 A1 9/2010 Rummery et al.
2010/0229872 A1 9/2010 Ho
2010/0258132 A1 10/2010 Moore
2010/0258136 A1 10/2010 Doherty et al.
2010/0294281 A1 11/2010 Ho
2010/0307502 A1 12/2010 Rummery et al.
2010/0313891 A1 12/2010 Veliss et al.
2010/0319700 A1 12/2010 Ng et al.
2010/0326445 A1 12/2010 Veliss et al.
2011/0067704 A1* 3/2011 Kooij ................ A61M 16/0858 128/207.18
2011/0072553 A1 3/2011 Ho
2011/0088699 A1 4/2011 Skipper
2011/0126838 A1 6/2011 Alberici
2011/0162654 A1 7/2011 Carroll et al.
2011/0232649 A1 9/2011 Collazo et al.
2011/0253136 A1 10/2011 Sweeney
2011/0253156 A1 10/2011 Sweeney
2011/0259337 A1 10/2011 Hitchcock et al.
2011/0265796 A1 11/2011 Amarasinghe et al.
2011/0290253 A1 12/2011 McAuley
2012/0125339 A1 5/2012 Ho et al.
2012/0132208 A1 5/2012 Judson et al.
2012/0132209 A1 5/2012 Rummery
2012/0138061 A1* 6/2012 Dravitzki .......... A61M 16/0633 128/205.25
2012/0204879 A1 8/2012 Cariola et al.
2012/0285457 A1 11/2012 Mansour et al.
2012/0304999 A1 12/2012 Swift et al.
2012/0318265 A1 12/2012 Amirav et al.
2013/0133659 A1 5/2013 Ng et al.
2013/0133664 A1 5/2013 Startare
2013/0152918 A1 6/2013 Rummery et al.
2013/0160769 A1 6/2013 Ng et al.
2014/0026888 A1 1/2014 Matula
2014/0083428 A1 3/2014 Rothermel et al.
2014/0083430 A1 3/2014 Matula, Jr. et al.
2014/0137870 A1 5/2014 Barlow et al.
2014/0261432 A1 9/2014 Eves et al.
2014/0290669 A1 10/2014 Ngo
2014/0311492 A1 10/2014 Stuebiger et al.
2014/0338672 A1 11/2014 D'Souza et al.
2014/0373834 A1 12/2014 Gunaratnam et al.
2015/0033457 A1 2/2015 Tryner et al.
2015/0090266 A1 4/2015 Melidis et al.
2015/0246198 A1 9/2015 Bearne et al.
2015/0335846 A1 11/2015 Romagnoli et al.
2015/0352308 A1 12/2015 Cullen et al.
2015/0374944 A1 12/2015 Edwards et al.
2016/0001028 A1 1/2016 McAuley et al.
2016/0008558 A1 1/2016 Huddart et al.
2016/0015922 A1 1/2016 Chodkowski et al.
2016/0038707 A1 2/2016 Allan et al.
2016/0051786 A1 2/2016 McAuley et al.
2016/0213873 A1 7/2016 McAuley et al.
2016/0213874 A1 7/2016 Davidson et al.
2016/0296720 A1 10/2016 Henry et al.
2017/0246411 A1 8/2017 Mashal et al.
2017/0296770 A1 10/2017 Gunaratnam et al.
2017/0368288 A1 12/2017 Stephens et al.
2018/0221615 A1 8/2018 Sevincli
2018/0250483 A1 9/2018 Olsen et al.
2018/0256844 A1 9/2018 Galgali et al.
2019/0001095 A1 1/2019 Rose et al.
2020/0046928 A1 2/2020 Allan
2020/0171260 A1 6/2020 McLaren
2020/0197644 A1 6/2020 McAuley et al.
2021/0228829 A1 7/2021 McAuley et al.
2022/0105294 A1 4/2022 McAuley et al.
2022/0249794 A1 8/2022 McAuley et al.
2022/0331539 A1 10/2022 McAuley et al.
2023/0084024 A1 3/2023 McAuley et al.
2023/0086085 A1 3/2023 McAuley et al.
2023/0256188 A1 8/2023 McAuley et al.
2023/0381440 A1 11/2023 Allan et al.

FOREIGN PATENT DOCUMENTS

CA 2648690 11/2007
CD 000966064-0001 9/2008
CD 0009660640002 9/2008
CD 0009660640003 9/2008
CD 0009660640004 9/2008
CD 0009660640017 9/2008
CN 2172538 7/1994
CN 1780265 12/2005
CN 1750854 3/2006
CN 1784250 6/2006
CN 1901961 1/2007
CN 100502972 C 6/2009
CN 101991897 A 3/2011
CN 307174593 3/2022
DE 895692 11/1953
DE 29723101 U1 7/1998
DE 19603949 11/1998
DE 102005041717 4/2006

(56) References Cited

FOREIGN PATENT DOCUMENTS

| | | | |
|---|---|---|---|
| DE | 102006011151 | | 9/2007 |
| EP | 0 281 275 | | 9/1988 |
| EP | 0350322 | | 1/1990 |
| EP | 0 427 474 | | 5/1991 |
| EP | 0427474 | A2 | 5/1991 |
| EP | 0462701 | | 12/1991 |
| EP | 0 747 078 | | 12/1996 |
| EP | 0830180 | | 3/1998 |
| EP | 1099452 | | 5/2001 |
| EP | 1 258 266 | | 11/2002 |
| EP | 1 306 098 | | 5/2003 |
| EP | 1 488 820 | | 12/2004 |
| EP | 1 582 231 | | 10/2005 |
| EP | 1582231 | A1 | 10/2005 |
| EP | 2 042 209 | | 4/2009 |
| EP | 2042209 | A1 | 4/2009 |
| EP | 2 130 563 | | 12/2009 |
| EP | 2130563 | A1 | 12/2009 |
| EP | 2 145 645 | | 1/2010 |
| EP | 1 753 495 | | 9/2010 |
| EP | 2145645 | B1 | 1/2012 |
| EP | 2451518 | | 5/2012 |
| EP | 1 481 702 | | 9/2012 |
| EP | 2 749 176 | | 7/2014 |
| EP | 1 646 910 | | 8/2015 |
| EP | 2 022 528 | | 3/2016 |
| EP | 1 841 482 | | 7/2016 |
| FR | 2658725 | | 8/1991 |
| FR | 2749176 | | 12/1997 |
| FR | 2823122 | | 10/2002 |
| GB | 190224431 | | 12/1902 |
| GB | 880824 | | 10/1961 |
| GB | 979357 | | 1/1965 |
| GB | 1467828 | | 3/1977 |
| GB | 2133275 | | 7/1984 |
| GB | 2173274 | | 10/1986 |
| GB | 2186801 | | 8/1987 |
| GB | 2385533 | | 8/2003 |
| GB | 2408459 | A | 1/2005 |
| GB | 2406797 | A | 4/2005 |
| JP | 62-024721 | | 2/1987 |
| JP | S6224721 | | 2/1987 |
| JP | H09-010311 | | 1/1997 |
| JP | 2000-325481 | | 11/2000 |
| JP | 2004-016488 | | 1/2004 |
| JP | 2005-529687 | | 10/2005 |
| JP | 2005-537906 | | 12/2005 |
| JP | 2007-516750 | | 6/2007 |
| NZ | 531332 | | 2/2004 |
| NZ | 534606 | | 8/2004 |
| NZ | 528029 | | 3/2005 |
| NZ | 548575 | | 7/2006 |
| NZ | 551103 | | 11/2006 |
| NZ | 567740 | | 12/2009 |
| WO | WO 82/003548 | | 10/1982 |
| WO | WO 97/00092 | | 1/1997 |
| WO | WO 97/32494 | | 9/1997 |
| WO | WO 97/45154 | | 12/1997 |
| WO | 1998004311 | A1 | 2/1998 |
| WO | WO 98/04310 | | 2/1998 |
| WO | WO 98/04311 | | 2/1998 |
| WO | WO 98/018514 | | 5/1998 |
| WO | WO 98/024499 | | 6/1998 |
| WO | WO 98/048878 | | 11/1998 |
| WO | WO 98/57691 | | 12/1998 |
| WO | WO 99/04842 | | 2/1999 |
| WO | WO 99/43375 | | 9/1999 |
| WO | WO 99/058181 | | 11/1999 |
| WO | WO 99/058198 | | 11/1999 |
| WO | WO 00/050122 | | 8/2000 |
| WO | WO 00/057942 | | 10/2000 |
| WO | WO 00/069497 | | 11/2000 |
| WO | WO 00/74509 | | 12/2000 |
| WO | WO 00/074758 | | 12/2000 |
| WO | WO 00/078384 | | 12/2000 |
| WO | WO 01/00266 | | 1/2001 |
| WO | WO 01/32250 | | 5/2001 |
| WO | WO 01/041854 | | 6/2001 |
| WO | WO 01/058293 | | 8/2001 |
| WO | WO 01/062326 | | 8/2001 |
| WO | WO 01/89381 | | 11/2001 |
| WO | WO 01/94721 | | 12/2001 |
| WO | WO 01/097892 | | 12/2001 |
| WO | WO 01/97892 | | 12/2001 |
| WO | WO 01/097893 | | 12/2001 |
| WO | WO 02/005883 | | 1/2002 |
| WO | WO 02/011804 | | 2/2002 |
| WO | WO 02/047749 | | 6/2002 |
| WO | WO 02/074372 | | 9/2002 |
| WO | WO 03/035156 | | 5/2003 |
| WO | WO 03/076020 | | 9/2003 |
| WO | WO 03/082406 | | 10/2003 |
| WO | WO 03/092755 | | 11/2003 |
| WO | WO 04/007010 | | 1/2004 |
| WO | WO 04/096332 | | 1/2004 |
| WO | WO 04/012803 | | 2/2004 |
| WO | WO 04/022146 | | 3/2004 |
| WO | WO 04/022147 | | 3/2004 |
| WO | WO 04/030510 | | 4/2004 |
| WO | WO 04/030736 | | 4/2004 |
| WO | WO 04/041341 | | 5/2004 |
| WO | WO 04/041342 | | 5/2004 |
| WO | WO 04/052438 | | 6/2004 |
| WO | WO 04/071565 | | 8/2004 |
| WO | WO 04/073777 | | 9/2004 |
| WO | WO 04/073778 | | 9/2004 |
| WO | WO 04/079066 | | 9/2004 |
| WO | WO 05/010608 | | 2/2005 |
| WO | WO 05/016403 | | 2/2005 |
| WO | WO 05/018523 | | 3/2005 |
| WO | WO 05/021075 | | 3/2005 |
| WO | WO 05/051468 | | 6/2005 |
| WO | WO 05/063326 | | 7/2005 |
| WO | WO 05/063328 | | 7/2005 |
| WO | WO 05/076874 | | 8/2005 |
| WO | WO 05/079726 | | 9/2005 |
| WO | WO 05/086943 | | 9/2005 |
| WO | WO 05/086946 | | 9/2005 |
| WO | WO 05/097247 | | 10/2005 |
| WO | WO 05/123166 | | 12/2005 |
| WO | WO 06/000046 | | 1/2006 |
| WO | WO 06/050559 | | 5/2006 |
| WO | WO 06/069415 | | 7/2006 |
| WO | WO 06/074513 | | 7/2006 |
| WO | WO 06/074514 | | 7/2006 |
| WO | WO 06/074515 | | 7/2006 |
| WO | WO 06/096924 | | 9/2006 |
| WO | WO 06/130903 | | 12/2006 |
| WO | WO 06/138346 | | 12/2006 |
| WO | WO 06/138416 | | 12/2006 |
| WO | WO 07/006089 | | 1/2007 |
| WO | WO 07/009182 | | 1/2007 |
| WO | WO 07/021777 | | 2/2007 |
| WO | WO 07/022562 | | 3/2007 |
| WO | WO 07/041751 | | 4/2007 |
| WO | WO 07/041786 | | 4/2007 |
| WO | WO 07/045008 | | 4/2007 |
| WO | WO 07/048174 | | 5/2007 |
| WO | WO 07/053878 | | 5/2007 |
| WO | WO 07/114492 | | 10/2007 |
| WO | WO 07/147088 | | 12/2007 |
| WO | WO 08/007985 | | 1/2008 |
| WO | WO 08/011682 | | 1/2008 |
| WO | WO-2008007985 | A1 * | 1/2008 ........ A61M 16/0057 |
| WO | WO 08/014543 | | 2/2008 |
| WO | WO 08/030831 | | 3/2008 |
| WO | WO 08/036625 | | 3/2008 |
| WO | WO 08/043134 | | 4/2008 |
| WO | WO 08/060295 | | 5/2008 |
| WO | WO 08/068966 | | 6/2008 |
| WO | WO 08/070929 | | 6/2008 |
| WO | WO 08/106716 | | 9/2008 |
| WO | WO 08/148086 | | 12/2008 |
| WO | WO 09/026627 | | 3/2009 |

(56) References Cited

FOREIGN PATENT DOCUMENTS

| | | |
|---|---|---|
| WO | WO 09/022248 | 4/2009 |
| WO | WO 09/052560 | 4/2009 |
| WO | WO 09/059353 | 5/2009 |
| WO | WO 09/092057 | 7/2009 |
| WO | WO 09/109005 | 9/2009 |
| WO | WO 09/133561 | 11/2009 |
| WO | WO 09/139647 | 11/2009 |
| WO | WO 10/066004 | 6/2010 |
| WO | WO 10/073142 | 7/2010 |
| WO | WO 10/131189 | 11/2010 |
| WO | WO 10/135785 | 12/2010 |
| WO | WO 10/148453 | 12/2010 |
| WO | WO 11/014931 | 2/2011 |
| WO | WO 11/059346 | 5/2011 |
| WO | WO 11/060479 | 5/2011 |
| WO | WO 11/077254 | 6/2011 |
| WO | WO 12/040791 | 4/2012 |
| WO | WO 12/045127 | 4/2012 |
| WO | WO 12/052902 | 4/2012 |
| WO | WO 12/143822 | 10/2012 |
| WO | WO 14/015382 | 1/2014 |
| WO | WO 14/020469 | 2/2014 |
| WO | WO 14/109749 | 7/2014 |
| WO | WO 14/175752 | 10/2014 |
| WO | WO 14/175753 | 10/2014 |
| WO | WO 15/033287 | 3/2015 |
| WO | WO 16/000040 | 1/2016 |
| WO | WO 17/049356 | 3/2017 |
| WO | WO 17/049357 | 3/2017 |
| WO | WO 18/007966 | 1/2018 |
| WO | WO 18/064712 | 4/2018 |

OTHER PUBLICATIONS

MatWeb Material Property Data, "Overview of Materials for Silicone Rubber", https://www.matweb.com/search/DataSheet.aspx?MatGUID=cbe7a469897a47eda563816c86a73520, accessed May 1, 2024 (Year: 2024).*

Opponent's outline of submissions in the matter of Australian patent applications Nos. 20223628, 2021201838, 2021201840, 2021201841, 2021201842 and 2021201843, dated Mar. 13, 2024, 51 pp.

Applicant's Outline of Submissions in the matter of Australian Patent Application Nos. 2020223628, 2021201838, 2021201840, 2021201841, 2021201842, 2021201843 dated Mar. 20, 2024, 72 pp.

U.S. Appl. No. 60/493,515, filed Aug. 8, 2002, Sleeper et al.

U.S. Appl. No. 60/496,059, filed Aug. 18, 2003, Ho et al.

U.S. Appl. No. 60/529,696, filed Dec. 16, 2003, Lithgow et al.

U.S. Appl. No. 61/064,406, filed Mar. 4, 2008, Wehbeh.

U.S. Appl. No. 61/071,893, filed May 22, 2008, Wehbeh et al.

U.S. Appl. No. 61/136,617, filed Sep. 19, 2008, Wehbeh et al.

Resmed Mirage Swift™ II Nasal Pillows System product page (http://www.resmed.com/en-us/products/masks/mirage_swift_II_nasal_pillows._system/Mirage-Swift-II-Nasal-Pillows-System.html?menu=products); archived Jul. 21, 2008, 2 pp.

Resmed Mirage Swift™ II user brochure (http://www.resmed.com/en us/products/masks/mirage-swift_II_nasal_pillows_system/documents/mirage-swift-ii-np-brochure-patient-english-USA.pdf) copyright 2007, 4 pp.

ResMed Mirage Swift II Fitting guide (http://www;resmed.com/en-us/products/masks/mirage_swift_II_nasal_pillows_system/documents/mirage-swift_ii_np-fitting English.pdf) copyright 2006, 2 pp.

ResMed Mirage Swift II comparison to older Swift patient interface (http://www.resmed.com/en-us/products/masks/mirage_swift_II_nasal_pillows_system/documents/mirage-swift-ii-np-comparison-guide.pdf, 2007, 6 pp.

ResMed Mirage Swift II user guide (http://www.resmed.com/en-us/products/service_and_support/documents/60893rl_mirage_swiftll_nasal_userglide_us_multi.pdf) copyright 2006, 1 p.

ResMed Mirage Swift II component card (http://www.resmed.com/en-us/products/masks/mirage_swift_II_nasal_pillows_system/documents/mirage-swift-ii-np-cc-USA.pdf); copyright 2006, 2 pp.

Resmed Swift™ LT Nasal Pillows System, product page, (http://www.resmed.com/en- us/products/masks/mirage_swift_II_nasal_pillows_system/Mirage-Swift-II-Nasal_Pillows-System.html?menu=products), Jul. 3, 2008, 2 pp.

Resmed Swift LT user brochure, (http://www.resmed.com/en-us/products/masks/mirage_swift_II_nasal_pillows_system/documents/mirage-swift-ii-np-brochure-patient-english-USA.pdf), copyright 2008, 4 pp.

Resmed Swift™ LT component card (http://www.resmed.com/en-us/assets/documents/product/swift_lt/components_card/1012463_swift-lt_components-card _usa_eng.pdf) copyright 2008, 46 pp.

Resmed Swift™ LT fitting guide, (http://www.resmed.com/en-us/assets/documents/product/swift-ll/clinical_fact_sheet/1012406 swift-ii_fact-sheet_usa_eng.pdf), 2008, 2 pp.

Resmed Swift™ LT fact sheet (http://www.resmcd.com/en-us/assets/documents/product/swift-lt/clinical_fact_sheet/1012406 swiftlt_fact-sheet_usa_eng.pdf, copyright 2008, 4 pp.

Resmed Swift™ LT image gallery (http://www.resmed.com/en-us/products/masks/swift_l_nasal_pillows_system/imagegallery.html?menu=products, Apr. 25, 2008, 2 pp.

Resmed Swift™ LT interactive fitting guide—screenshot from troubleshooting part (http://www.resmed.com/enus/assets/multimedia/product/swift-lt/flash/swift-lt-fitting-eng.swf), Jul. 3, 2008, 2 pp.

Puritan Bennett Breeze® SleepGear® CPAP Interface, product page (http:/puritanbennett.com/prod/product.aspx?id=233); archived Oct. 19, 2007, 2 pp.

Puritan Bennett Breeze® SleepGear® User's Guide (http://puritanbennett.com/_catalog/pdf/dfu/107598a00[l].pdf); copyright 2007, 18 pp.

Puritan Bennett Breeze® SleepGear® sales sheet (http://www.puritanbennett.com/_Catalog/PDF/Product/BreezeSleepGear.pdf) copyright 2016, 7 PP.

Puritan Bennett mask coding matrix (http://www.puritanbennett.com/_Catalog/PDF/Product/BreezeSlpGear(ST03700).pdf) copyright 2006, 3 pp.

Puritan Bennett Breeze fitting guide (http://www.puritanbennett.com/_Catalog/PDF/Product/BreezeFittingPoster.pdf, Oct. 19, 2007, 1 p.

Respironics Optilife Pillows mask product page (http://optilife.respironics.com:80/); archived Nov. 21, 2007, 2 pp.

Respironics Optilife Pillows mask part numbers page (http://optilife.respironics.com:80/Parts.aspx); archived Nov. 23, 2007, 4 pp.

Respironics Optilife Pillows mask FAQ (http;//optilife.respironics.com:80/fags.aspx); archived Nov. 23, 2007, 6 pp.

Respironics Optilife Pillows mask feature page (http://optilife.respironics.com:80/features.aspx); archived Nov. 23, 2007, 4 pp.

Respironics Optilife Pillows mask fitting guide screen shot (http://optilife.respironics.com:80/fittingGuide.aspx); archived Aug. 7, 2008, 1 p.

Respironics Optilife Pillows mask adjustment video screenshots, https://www.youtube.com/watch?v=shjcNmvvcBA); uploaded Aug. 3, 2008, 2 pp.

Puritan Bennett Breeze description; copyright 2000 by Mallinckrodt Inc., 4 pp.

Fisher & Paykel Opus product page, archived Sep. 3, 2009, 2 pp.

Fisher & Paykel Opus patient interface product photographs, Jul. 2007, 6 pp.

Photographs of Opus 360 nasal pillows mask patient instructions RevB, Jul. 2007, 4 pp.

Respironics Optilife brochure detailing updates; copyright 2008; dated Mar. 26, 2008, 3 pp.

Fisher & Paykel Opus product page, archived Sep. 7, 2009, 2 pp.

Fisher & Paykel Opus "Off-the-lips" pillows explanation page, archived Aug. 23, 2009, 2 pp.

Fisher & Paykel Opus "Off-the-lips" patient interface brochure, archived Oct. 14, 2009, 6 pp.

Fisher & Paykel Opus user-guide, archived Nov. 17, 2009, 2 pp.

Fisher & Paykel HC200 Series Nasal CPAP Blower & Heated Humidifier User Manual, 17 pp., May 1998.

Fisher & Paykel Healthcare, FlexiFit®431 Full Face Mask instructions, 2010, 4 pp.

Fisher & Paykel Healthcare, FlexiFit™ 431 Full Face Mask, specification sheet, 2004, 2 pp.

(56) References Cited

OTHER PUBLICATIONS

Fisher & Paykel Healthcare, Interface Solutions Product Profile, 2006, 12 pp.
Fisher & Paykel MR810 Manual, Rev. C, 2004, 43 pp.
HomeDepot.com—Ring Nut Sales Page (Retrieved Oct. 16, 2015 from http://www.homedepot.com/p/Everbilt-1-2-in-Galvanized-HexNut-804076/20464- 7893), 4 pp.
Malloy, 1994, Plastic Part Design for Injection Molding, Hanser Gardner Publications, Inc, Cincinnati, OH, 14 pp.
Merriam-Webster's Collegiate Dictionary, Eleventh Edition, 2004, pp. 703, 905, 1074, 1184.
Philips Respironics 'System One Heated Humidifier—User Manual', 2011, pp. 1-16, [retrieved on Nov. 25, 2013] from the internet: URL: http://www.cpapxchange.com/cpap-machines-biap-machines/system-one-60-seri- es-cpap-humidifier-manual.pdf front cover, pp. 3-4 and 6.
ResMed Exhibit, FlexiFit™ 431, product brochure, web pages (Wayback Machine), 2006, 23 pp.
ResMed Origins Brochure (Retrieved Apr. 17, 2016 from http://www.resmed.com/us/dam/documents/articles/resmedorigins.pdf), 64 pp.
ResMed Ultra Mirage™ Full Face Mask, product brochure, 2004, 2 pp.
ResMed Ultra Mirage™ Full Face Mask, product brochure, web pages (Wayback Machine), 2006, 9 pp.
ResMed, Mirage Swift™ Nasal Pillows System from ResMed, product brochure, 2004, 6 pp.
ResMed, Mirage Swift™ Nasal Pillows System: User's Guide, product brochure, 2004, 11 pp.
ResMed, Mirage Vista™ Nasal Mask: Components Card, product brochure, 2005, 1 p.
The American Heritage Dictionary of the English Language, Fourth Edition, 2006, pp. 1501, 1502, 1650.
WeddingBands.com—Men's Wedding Ring Shopping Page (Retrieved Oct. 16, 2015 from http://www.weddingbands.com/ProductPop.sub.--wedding.sub.--band- s.sub.--metal/48214W.html), 3 pp.
ResMed, Oct. 1999, Mirage® Full Face Mask Update, Product Bulletin No. 161, 3 pp.
ResMed, Dec. 6, 1998, Mirage Full Face Cushion—Medium, drawing, 1 p.
ResMed, Jun. 20, 2000, Brochure, Mirage Full Face Mask, 5 pp.
ResMed, Oct. 4, 2000, Mirage® Full Face Mask, User's Guide, 3 pp.
U.S. Appl. No. 61/064,406, 34 pages, copy provided by USPTO on Feb. 23, 2009.
U.S. Appl. No. 61/071,893, 43 pages, copy provided by USPTO on Feb. 23, 2009.
U.S. Appl. No. 61/136,617, 82 pages, copy provided by USPTO on Feb. 23, 2009.
Petition for Inter Partes Review of U.S. Pat. No. 8,479,741 Pursuant to 35 U.S.C. §§ 311-19, 37 C.F.R. § 42, IPR2016-01714, dated Sep. 7, 2016.
Patent Owner Preliminary Response to Petition for Inter Partes Review of U.S. Pat. No. 8,479,741, IPR2016-01714, filed Dec. 14, 2016.
Decision Denying Institution of Inter Partes Review of U.S. Pat. No. 8,479,741 Pursuant to 37 C.F.R. § 42.108, IPR2016-01714, entered Mar. 10, 2017.
Declaration of Dr. John Izuchukwu, Ph.D., P.E., U.S. Pat. No. 8,443,807, IPR Nos. 2016-1726 & 2016-1734, dated Sep. 7, 2016.
Declaration of Dr. John Izuchukwu, Ph.D., P.E., U.S. Pat. No. 8,479,741, IPR Nos. 2016-1714 & 2016- 1718, dated Sep. 7, 2016.
Patent Owner Preliminary Response to Petition for Inter Partes Review of U.S. Pat. No. 8,479,741, IPR2016-01718, filed Dec. 16, 2016.
Decision Denying Institution of Inter Partes Review of U.S. Pat. No. 8,479,741 Pursuant to 37 C.F.R. § 42.108, IPR2016-01718, entered Mar. 13, 2017.
Petition for Inter Partes Review of U.S. Pat. No. 8,479,741 Pursuant to 35 U.S.C. §§ 311-19, 37 C.F.R. § 42, IPR2016-01718, dated Sep. 7, 2016.
Petition for Inter Partes Review of U.S. Pat. No. 8,443,807 Pursuant to 35 U.S.C. §§ 311-19, 37 C.F.R. § 42, IPR2016-01726, dated Sep. 7, 2016.
Patent Owner Preliminary Response to Petition for Inter Partes Review of U.S. Pat. No. 8,443,807, IPR2016-01726, filed Dec. 13, 2016.
Petition for Inter Partes Review of U.S. Pat. No. 8,443,807 Pursuant to 35 U.S.C. §§ 311-19, 37 C.F.R. § 42, IPR2016-01734, dated Sep. 7, 2016.
Patent Owner Preliminary Response to Petition for Inter Partes Review of U.S. Pat. No. 8,443,807, IPR2016-01734, filed Dec. 22, 2016.
Decision Denying Institution of Inter Partes Review of U.S. Pat. No. 8,443,807 Pursuant to 37 C.F.R. § 42.108, IPR2016-01734, entered Mar. 13, 2017.
File History of U.S. Pat. No. 8,479,741 to McAuley et al., published Oct. 1, 2009.
File History of U.S. Pat. No. 8,443,807 to McAuley et al., published Jan. 7, 2010.
Patent Owner's Complaint for *Fisher & Paykel Healthcare Ltd.* v. *ResMed Corp.*, Case No. 2:16-cv-06099-R-AJW (C.D. Cal.), dated Aug. 15, 2016.
Patent Owner's Notice of Voluntary Dismissal Without Prejudice for *Fisher & Paykel Healthcare Ltd.* v. *ResMed Corp.*, Case No. 2:16-cv-06099-R-AJW (C.D. Cal.), dated Aug. 16, 2016.
Patent Owner's Complaint for *Fisher & Paykel Healthcare Ltd.* v. *ResMed Corp.*, Case No. 3:16-cv-02068-GPC-WVG (S.D. Cal.), dated Aug. 16, 2016.
Petitioners' Complaint for *ResMed Inc., et al.* v. *Fisher & Paykel Healthcare Corp. Ltd., et al.*, Case No. 3:16-cv-02072-JAH-MDD (S.D. Cal.), dated Aug. 16, 2016.
Petitioners' Notice of Voluntary Dismissal Without Prejudice for *ResMed Inc., et al.* v. *Fisher & Paykel Healthcare Corp. Ltd., et al.*, Case No. 3:16-cv-02072-JAH-MDD (S.D. Cal.) , dated Aug. 18, 2016.
Statutory Declaration made by Alistair Edwin McAuley, Apr. 9, 2015, in the matter of an Opposition by Fisher & Paykel Healthcare Limited of Australian patent application 2009221630 in the name of ResMed Limited.
Statutory Declaration made by Alistair Edwin McAuley, Apr. 14, 2015, in the matter of an Opposition by Fisher & Paykel Healthcare Limited of Australian patent application 2009221630 in the name of ResMed Limited.
Statutory Declaration made by Alistair Edwin McAuley, Apr. 17, 2015, in the matter of an Opposition by Fisher & Paykel Healthcare Limited of Australian patent application 2009221630 in the name of ResMed Limited.
Statutory Declaration made by Alistair Edwin McAuley, Sep. 16, 2015, in the matter of an Opposition by Fisher & Paykel Healthcare Limited of Australian patent application 2009221630 in the name of ResMed Limited.
First Affidavit of Alistair Edwin McAuley, Dec. 5, 2016, in the matter of *Fisher and Paykel Healthcare Limited* v. *ResMed Limited* filed in the Federal Court of Australia.
Second Affidavit of Alistair Edwin McAuley, Dec. 21, 2016, in the matter of *Fisher and Paykel Healthcare Limited* v. *ResMed Limited* filed in the Federal Court of Australia.
Third Affidavit of Alistair Edwin McAuley, Jan. 31, 2017, in the matter of *Fisher and Paykel Healthcare Limited* v. *ResMed Limited* filed in the Federal Court of Australia, 284 pp.
Declaration of Anthony Michael Ging in IPR 2019-000172, IPR 2019-000173, IPR 2019-000177, IPR 2019-000178, dated Nov. 8, 2018, 329 pp.
McGraw-Hill Dictionary of Scientific and Technical Terms, Sixth Edition, 2003, Tube, p. 2200.
Claim Chart for AirFit P10, U.S. Pat. No. 9,333,315, dated Nov. 7, 2018, 3 pp.
Scheduling Order dated Jul. 16, 2019 in IPR2019-00180, 12 pp.
Decision to Institute dated Jul. 16, 2019 in IPR2019-00180, 34 pp.

(56) References Cited

OTHER PUBLICATIONS lDecision Denying Institute of Inter Partes Review dated Jul. 16, 2019 in IRP2019-00179, 32 pp.
An extract of parallel infringement proceedings on the basis of the opposed patent that a reinforcing member necessarily limits the lateral expansion of the cushion, dated Sep. 16, 2016, 3 pp.
Cleaning Instruction for the "Respironics ComfortClassic nasal mask" dated 2002, 4 pp.
A submission of Jan. 2, 2018 in parallel proceedings in New Zealand.
Excerpt from a notice of Sep. 6, 2017 in parallel proceedings pending in Germany.
Excerpt from a notice of Sep. 8, 2018 in parallel proceedings pending in Australia, 3 pp.
Excerpt from a submission of Jan. 31, 2017 in parallel proceedings pending in New Zealand, 2 pp.
lExpert opinion of Mr. Herbert T. Bauer, dated Sep. 4, 2017, 18 pp.
Extract of patentee's submission of Oct. 24, 2016 made in preliminary injunction proceedings based on the opposed patent.
FDA Home Medical Devised Databases, 510(k) Premarket Notification, 3 pp., Decision Date Jan. 31, 1996.
ResMed, Instruction manual of the "MAP Papillon mask", 2005.
Invoice for a Respironics ComfortClassic nasal mask, dated Jun. 13, 2003.
Letter of May 16, 2018 from the procedure of European patent No. EP 1 841 482 B1 with enclosures.
Opposition Division preliminary opinion in EP 1 841 482 B1 (with enclosures), filed Aug. 22, 2019.
Overview table regarding the auxiliary requests filed by the patentee, submitted May 16, 2018, 1 p.
Respironics Inc, Securities and Exchange Commission Form 10-K Annual Report, Jun. 30, 1998, 79 pp.
Respironics Monarch Mini, 1 p. with 7 pp. of photos dated Jul. 20, 2005.
Respironics, Inc, Sep. 30, 1997, Solo™ CPAP System, User Instructions, 33 pp.
Respironics ComfortCurve, 1 p. with 7 pp. of photos dated Nov. 4, 2005.
Affidavit of Christopher Bryn Sparks regarding European patent No. EP1841482B1, dated Nov. 12, 2018, 5 pp.
Affidavit of Christopher Earl Nightingale regarding European patent No. EP1841482B1, dated May 15, 2018, 16 pp.
Affidavit of Christopher Earl Nightingale regarding European patent No. EP1841482B1, dated May 9, 2018, 22 pp.
Affidavit of Richard Joseph Lordo regarding European patent No. EP1841482B1, dated Nov. 26, 2019, 3 pp.
Affidavit of Richard Joseph Lordo regarding European patent No. EP1841482B1, dated Nov. 29, 2018, 5 pp.
Department of Health and Human Services, May 7, 1997, Premarket Notification [501 (k)] review, Appendix 2, ResMed Operating Manual, Autoset Home System, 7 pp.
Resmed, Aug. 26, 1997, Mask frames, nasal cushions and headgear, web page, http://web/archive/org/web/199806111424/http:/www.resmed.com:80/maskframes/standard.htm., 3 pp.
ResMed, Feb. 12, 2001, Modular mask components and part numbers, https://web.archive.org/web/20010212075443/http:www.resmed.com:80/products/modular_components.htm, 1 p.
Photos of the Fisher and Paykel Healthcare Aclaim Mask, photos taken Oct. 6, 2023, 133 pp. (uploaded in 4 parts) The Fisher & Paykel Aclaim Mask has been publicly displayed, offered for sale and sold by the Applicant since at least 200.
Photos of the Healthdyne Soft Series Mask, photos taken Oct. 6, 2023, 45 pp. The Healthdyne Soft Series Mask has been publicly displayed, offered for sale and sold since at least 1993.
Letter to IP Australia dated Jun. 14, 2023 in Australian patent application No. 2021240146, 1 pp.
Opposition—Statement of Grounds and Particulars dated Jul. 18, 2023 in Australian patent application No. 2021240146, 20 pp.
The ResMed Mirage Activa Nasal Mask has been publicly displayed, offered for sale and sold by ResMed Pty Ltd since at least 2003 (Uploaded in 2 parts).
Photos of the ResMed Activa LT Mask and Associated Packaging, photos taken Feb. 3, 2023, 75 pp. (uploaded in 5 parts) The ResMed Mirage Activa LT Nasal Mask has been publicly displayed, offered for sale and sold by ResMed Pty Ltd since at least 2008 (Uploaded in 5 parts).
Photos of the Respironics Comfort Curve and Associated Packaging, photos taken Feb. 3, 2023, 143 pp. The Respironics Comfort Curve has been publicly displayed, offered for sale and sold by Respironics since at least 2005.
Photos of the Respironics Monarch Mini and Associated Packaging, photos taken Feb. 3, 2023, 152 pp. The Respironics Monarch Mini has been publicly displayed, offered for sale and sold by Respironics since at least 2000.
Statement of Grounds and Particulars dated Jun. 9, 2023 in Australian patent application No. 2021240146, 16 pp.
Statement of Grounds and Particulars dated Jul. 12, 2023 in Australian patent application No. 202173595, 19 pp.
Statutory Declaration for David John Palkon dated Sep. 7, 2023 in Australian patent application Nos. 2021240146 and 2021273595, 1879 pp. (uploaded in 4 parts).
Statutory Declaration for Melody Crinion dated Sep. 7, 2023 in Australian patent application Nos. 2021240146 and 2021273595, 98 pp.
Statutory Declaration of Robynne Lyndsay Sanders dated Sep. 7, 2023 in Australian patent application Nos. 2021240146 and 2021273595, 6566 pp (uploaded in 54 parts).
Photos of the Sullivan Bubble Mask, photos taken Feb. 3, 2023, 49 pp. (uploaded in 2 parts) The Sullivan Bubble Mask has been publicly displayed, offered for sale and sold by ResMed Pty Ltd (or its predecessor in title) since at least 1996.
Declaration of Jason Eaton dated Dec. 11, 2023 in the matter of Australian Patent Applications No. 2021240146 and 2021273595 in the name of Fisher & Paykel Healthcare Limited and Opposition by ResMed Pty Ltd, 227 pp.
ResMed FlexiFit brochure.
ResMed, Jun. 29, 1997, Mask Frames (Source: Wayback Machine Internet Archive); http://web.archive.org/web/19970629053430/http://www.resmed.com-Maskframes/mask.htm, 2 pp.
Decision Denying institution of Inter Partes Review of U.S. Pat. No. 8,443,807 Pursuant to 37 C.F.R. § 42.108, IPR2016-01726, entered Mar. 6, 2017.
Japanese Pretrial Examination Report dated Jan. 7, 2020 in patent application No. 2017-238259.
Patent Owner Preliminary Response to Petition for Inter Partes Review of U.S. Appl. No. 8,479,741, IPR2016-01718, filed Dec. 16, 2016.
Affidavit of Martina Elise Muellers regarding the purchase of a sample of the "Respironics ComfortClassic nasal mask" dated Nov. 20, 2018.
Declaration of Greg Olsen regarding the "Respironics ComfortClassic nasal mask" Nov. 20, 2018.
Feature analysis of claim 1 of EP 1 841 482 B1, dated Apr. 12, 2018, 1 p.
Instructions for Use for the "Respironics ComfortClassic Nasal Mask" (English and German version), 7 PP.

* cited by examiner

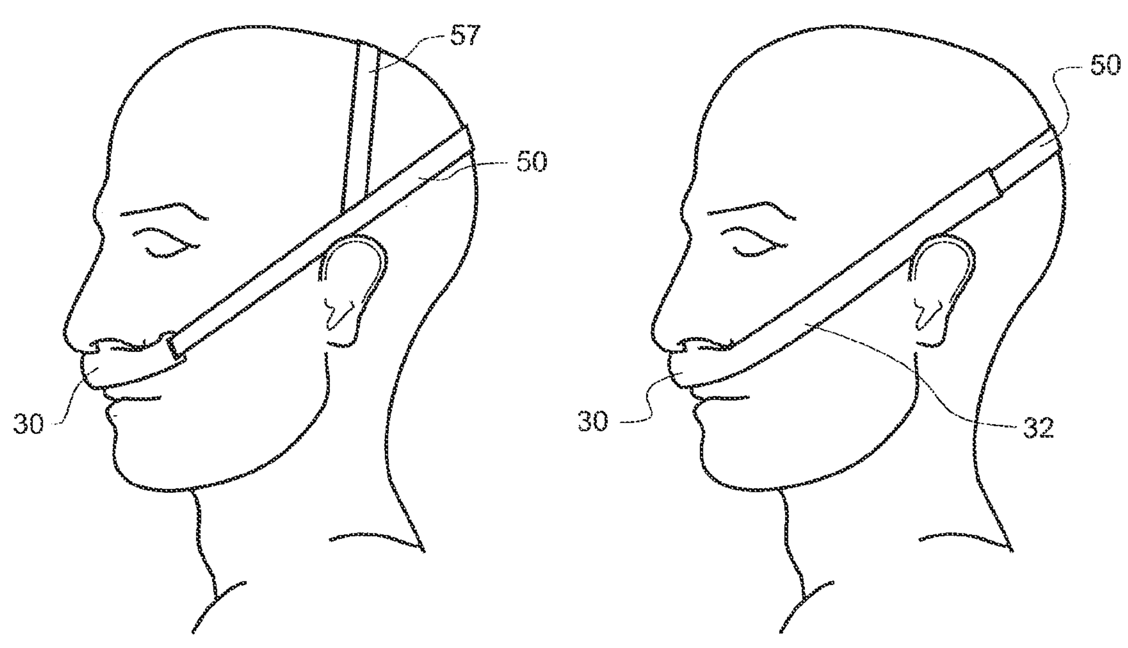
FIGURE 5A
FIGURE 5B
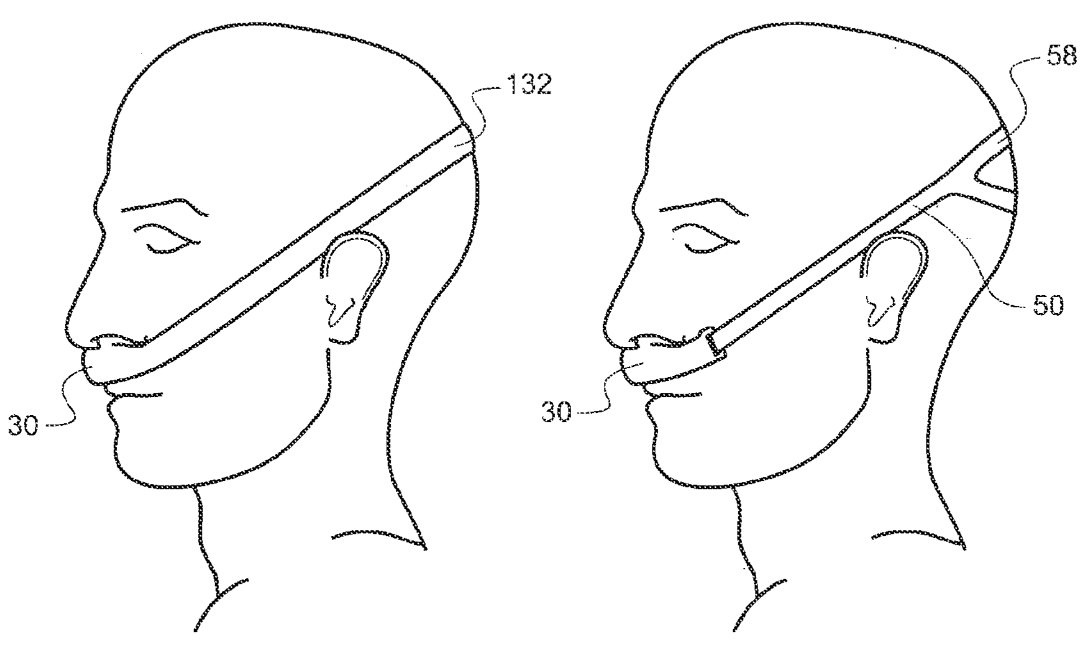
FIGURE 5C
FIGURE 5D

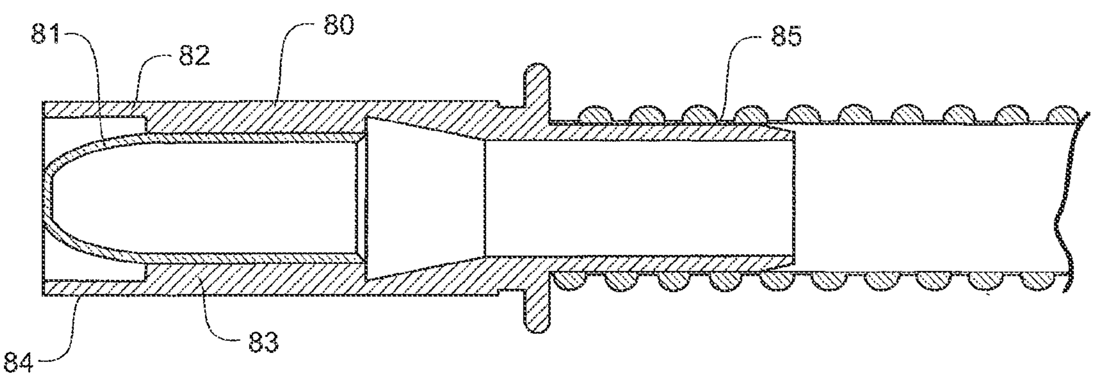
FIGURE 17
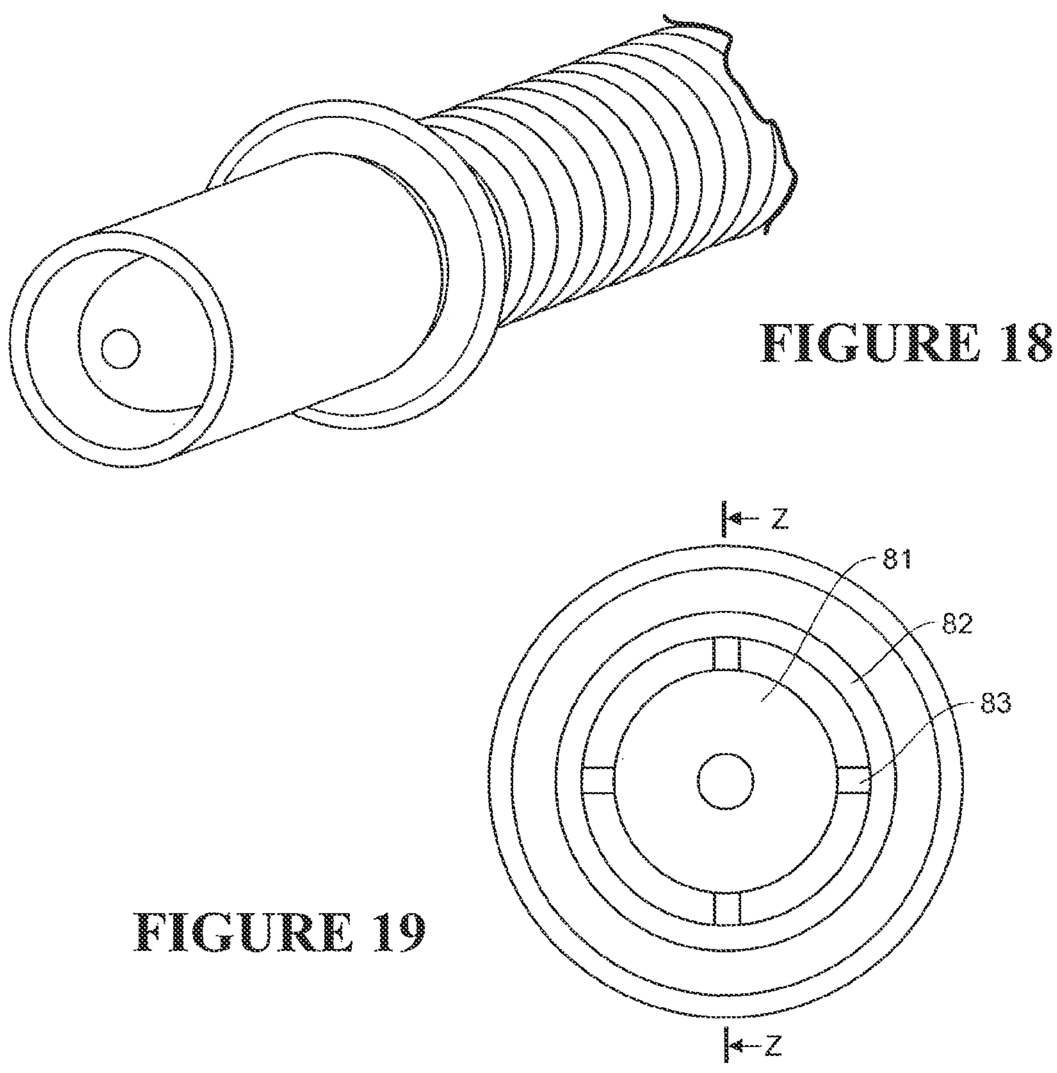
FIGURE 18
FIGURE 19

FIGURE 20
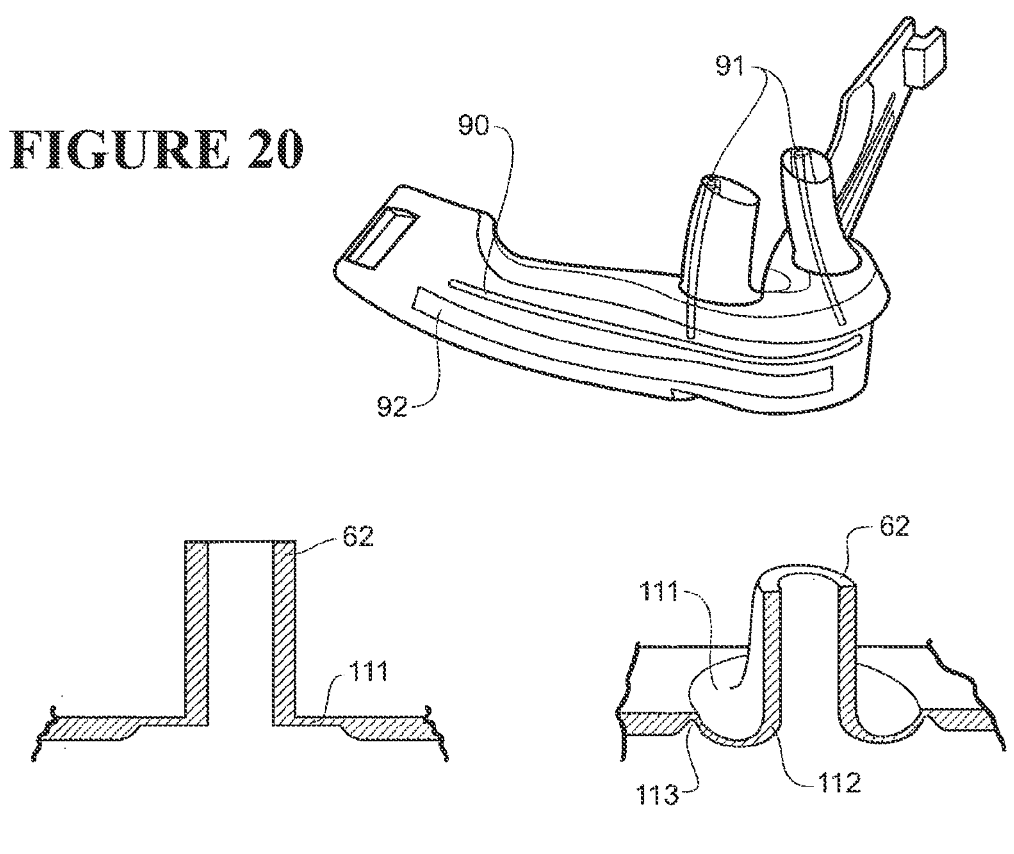
FIGURE 21A
FIGURE 21B
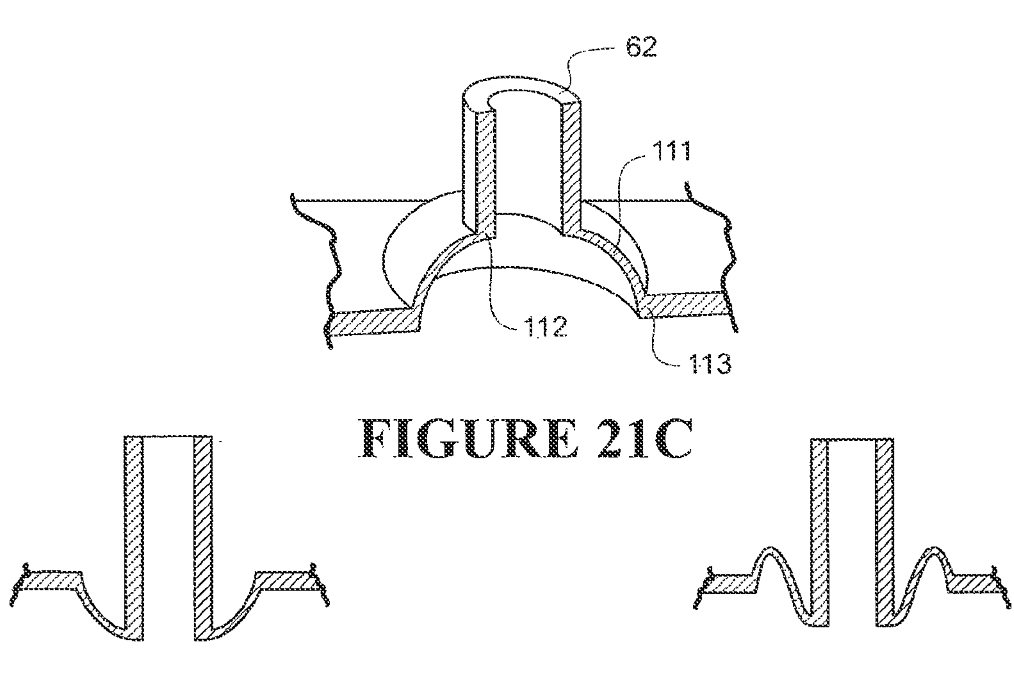
FIGURE 21C
FIGURE 21D
FIGURE 21E 60
31
40
45
79
62

78
77
69
31
40
60
62

NASAL INTERFACE

INCORPORATION BY REFERENCE TO ANY PRIORITY APPLICATIONS

Any and all applications for which a foreign or domestic priority claim is identified in the Application Data Sheet as filed with the present application are hereby incorporated by reference herein and made a part of the present disclosure.

BACKGROUND OF THE INVENTION

Field of the Invention

The present invention relates to a nasal interface for providing a flow of respiratory gases to a user.

Description of the Related Art

Nasal interfaces for providing a flow of gases to a user include interfaces having nasal outlets with pillows that provide a seal at a user's nostrils, and nasal cannulae interfaces where the nasal outlets are nasal prongs for insertion into a user's nostrils. A typical nasal cannula interface includes a plenum portion and entry tubing or a manifold section (symmetric or single sided) and a pair of open-ended prongs which protrude from the plenum or manifold and extend into the nostrils of the user in use to supply the patient with gases. Generally, but not always, the prongs of a nasal cannula are sized and shaped so that they do not seal against the nostrils of a patient. Nasal cannulae are used because these are advantageous in certain situations. For example, in circumstances where a patient is breathing normally, but requires supplementary gases such as oxygen. The existing market for nasal cannula includes devices suitable for delivery of gases in the 0 to 5 litres per minute range. These devices are typically supported by a double entry lumen of small diameter (2-3 mm range) that supply both sides of the nasal cannula and provides even or equal airflow to each nasal prong. These devices typically deliver dry gas flows of between 0 to 5 litres per minute, when the patient is self-breathing, and it is not necessary for the cannula prongs to seal against the nares of a user. A user will entrain the supplementary gases provided from the cannula along with atmospheric air as they inhale normally.

An example of a nasal cannula interface that seals against the nostrils is the Nasal-Aire interface made by Innomed, where gases are provided to the interface and the prongs by conduits or hoses that extend from the users nose across their cheeks, over their ears and around the back of their head.

WO 2008/060295 describes a non-sealing cannula that includes nasal prongs. There are many configurations described. The nasal prongs are adapted to deliver air to a patient's nasal passage and the different embodiments of prongs described include various external features, and may include passages that pass through the wall of the prongs to allow sensors or similar to measure the properties of gases in the prongs.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide an improved nasal interface or to at least provide the industry or public with a useful choice.

SUMMARY OF THE INVENTION

In one aspect, the present invention consists in a nasal interface for use in a system for providing a flow of respiratory gases to a user, the nasal interface comprising: a body made from a pliable first material, the body having an inlet for connection to a conduit providing a flow of gases and at least one nasal outlet comprising a tubular structure for interfacing with a user's nostril in use, the at least one nasal outlet fluidly connected to the inlet, a frame made from a second material more rigid than the first material, the frame attached to or integrally formed with the body, the frame adapted to engage the conduit to secure the conduit relative to the body.

Preferably the frame has a first projection for engaging the conduit to secure the conduit to the frame.

Preferably the frame comprises a second projection for engaging the body to removably secure the body to the frame thereby securing the conduit relative to the body.

Preferably the frame is permanently attached to the body.

Preferably the body is overmoulded to the frame.

Preferably the first projection is a first flange substantially perpendicular to the longitudinal axis of the conduit for engaging about a circumference of the conduit near an end of the conduit, the first flange having a hole open on one side for receiving the conduit, the diameter of the hole being matched to an external diameter of said circumference, the width of the opening being less than the external diameter of said circumference, in use the frame being elastically deformed during attachment to the conduit.

Preferably the body comprises a recess for receiving the second projection.

Preferably the second projection is a second flange substantially perpendicular to the longitudinal axis of the conduit, and the recess is a corresponding slot for receiving the second flange.

Preferably the inlet of the body is an aperture for receiving the end of the conduit, in use a rim around the aperture being sandwiched between the first flange and a surface extending radially from the conduit adjacent said circumference, sealingly engaging the inlet to the conduit.

Preferably the body has an annular groove extending about the aperture for receiving the surface extending radially from the conduit.

Preferably the interface further comprises the conduit for providing a flow of gases to the inlet, the conduit having a first radially extending surface and a second radially extending surface, the first flange engaging the conduit about a circumference between the first and second radially extending surfaces, the first flange being captured in a direction along the axis of the conduit between the first and second radially extending surfaces.

Preferably the nasal interface includes the conduit, the conduit connecting to the body from below the body, the inlet being directly below the nasal outlets.

Preferably the body comprises a pair of side arms, each side arm extending from a central portion of the body to in use pass across and contact a user's upper lip region Preferably in use, a distal end of each side arm rests substantially on the front of a user's face adjacent a side of the user's nose.

Preferably the body is an integrally formed unit comprising the inlet, nasal outlets and side arms.

Preferably a connection is formed in each side arm for connecting the nasal interface to headgear for holding the nasal interface in place on a user's head in use.

Preferably the frame comprises a pair of side arms, each side arm extending from a central portion of the frame to in use pass across a user's upper lip region.

Preferably in use, a distal end of each frame side arm rests substantially on the front of a user's face adjacent a side of the user's nose.

Preferably the frame is an integrally formed unit comprising the central portion, the first and second projections and the side arms.

Preferably in use the body arms rest in between a user's face and the frame side arms.

Preferably the distal end of each frame side arm is provided with a connection for attachment to head gear for holding the interface in place on a user's face in use.

Preferably the connection is a slot in a said side arm for receiving a head gear strap through to attach the head gear to the side arm, the slot being substantially perpendicular to a longitudinal axis of the side arm.

Preferably each body side arm comprises a retainer for attaching the body side arm to the corresponding frame side arm.

Preferably the connection is a slot for receiving a head gear strap through to attach the head gear to the side arm, the slot being substantially perpendicular to a longitudinal axis of the side arm, and the retainer is a tab located adjacent a distal end of the body side arm, in use the tab being received in said slot.

Preferably each connection is a quick release connector provided with a said side arm, the quick release connector adapted to quickly disconnect the head gear from at least one side.

Preferably the nasal interface is a nasal cannula, the at least one nasal outlet is a prong for insertion into a user's nostril in use.

Alternatively the at least one nasal outlet is a nasal pillow for providing a seal against a user's nostril in use.

In another aspect, the present invention consists in a nasal cannula for use in a system for providing a flow of respiratory gases to a user, the nasal cannula comprising: a body comprising an inlet for receiving a flow of gases and at least one nasal prong for insertion into a user's nostril in use, the at least one nasal prong fluidly connected to the inlet, an area for contacting the user's face or nose or both, in use contact between the area and the user's nose or face or both setting the position of the prongs forwardly in the user's nostrils to provide a gap between a rear extent of the nasal prong and the back of the user's nostril.

Preferably the size of the gap between the rear extent of the prong and the back of the user's nostril is at least 50% of the diameter of the prong.

Preferably the size of the gap between the rear extent of the prong and the back of the user's nostril is at least 100% of the diameter of the prong.

Preferably the area contacts an upper lip region of the user, in use headgear pulling the area against the user's upper lip region.

Preferably the area extends across most of the user's upper lip region.

Preferably the area contacts the user's septum.

Preferably the area contacts the junction between the user's septum and the user's upper lip, in use the headgear pulling the cannula against said junction.

Preferably in use contact between the area and the user's nose or face or both sets the angle of the prongs in the user's nasal passage so that the flow of gases are directed towards a front wall of the user's nasal passage.

Preferably the nasal prong is curved about a centre of curvature located towards the front of the user's nose so that the prong curves towards the front of the user's nasal passage in use.

Preferably wherein the nasal prong is substantially straight.

Preferably the body comprises a pair of side arms, each side arm in use passing across a user's upper lip region.

Preferably in use, a distal end of each side arm rests substantially on the front of a user's face adjacent a side of the user's nose.

Preferably the body is an integrally formed unit comprising the inlet, nasal prongs and side arms.

Preferably a connection is formed in each side arm for connecting the nasal cannula to headgear for holding the nasal cannula in place on a user's head in use.

Preferably the body comprises a bridge portion, in use the bridge portion supporting the cannula on a user's upper lip region, the bridge portion providing a channel between the bridge portion and a rear extent of the nasal prongs, the channel providing a path for exhaled gases to flow.

Preferably the cross section of the channel is adjustable to adjust the distance the nasal prongs are spaced from the area of the body in contact with a user's upper lip region in use.

Preferably the cross section of the channel is adjustable by a screw received in a screw thread.

Preferably the nasal cannula comprises a single nasal prong for insertion into a user's nostril in use, the user's other nostril being vacant, and the body comprising a channel aligned with the vacant nostril for exhaled gases to flow through.

In another aspect, the present invention consists in a nasal cannula for use in a system for providing a flow of respiratory gases to a user, the nasal cannula comprising: a body comprising an inlet for receiving a flow of gases and at least one nasal prong for insertion into a user's nostril in use, the at least one nasal prong fluidly connected to the inlet, the cannula comprising an area in contact with the user's face or nose or both, in use contact between the area and the user's nose or face or both setting the angle of the prongs in the user's nasal passage so that the flow of gases are directed towards a front wall of the user's nasal passage.

Preferably in use a longitudinal axis of each nasal prong at the tip of each nasal prong is parallel to or angled forward of a plane, the plane being vertical when the user is in a standing position with the user's head held level.

Preferably each prong has an outlet and in use the general plane of the outlet is parallel to the bottom wall of the user's nasal passage or angled forwardly towards the front wall of the user's nasal passage.

Preferably each prong has an outlet, and the outlet is not visible when the nasal prong is viewed from the rear and along a line parallel to where the bottom of the user's nasal passage would be relative to the prong in use.

Preferably each nasal prong has an outlet, and in use the outlet of each nasal prong faces the front wall of the user's nasal passage.

Preferably the area contacts an upper lip region of the user, in use headgear pulling the area against the user's upper lip.

Preferably the nasal prong is angled or curved so that a longitudinal axis of the prong at the tip of the prong is parallel to or angled forwardly of the plane of the area in contact with the user's upper lip region.

Preferably the angle between the longitudinal axis of the prong at the tip of the prong and the plane of the area in contact with the user's upper lip is at least 10°.

Preferably the area extends across most of the user's upper lip region.

Preferably the area contacts the user's septum.

Preferably the area contacts the junction between the user's septum and the user's upper lip, in use the headgear pulling the cannula against said junction.

Preferably in use contact between the area and the user's nose or face or both setting the position of the prongs forwardly in the user's nostrils to provide a gap between a rear extend of the nasal prong and the back of the user's nostril.

Preferably the size of the gap between the rear extent of the prong and the back of the user's nostril is at least 50% of the diameter of the prong.

Preferably the size of the gap between the rear extent of the prong and the back of the user's nostril is at least 100% of the diameter of the prong.

Preferably the nasal prong is curved about a centre of curvature located towards the front of the user's nose so that the prong curves towards the front of the user's nasal passage in use.

Preferably the nasal prong is substantially straight.

Preferably the body comprises a pair of side arms, each side arm in use passing across a user's upper lip region.

Preferably in use a distal end of each side arm rests substantially on the front of a user's face adjacent a side of the user's nose.

Preferably the body is an integrally formed unit comprising the inlet, nasal prongs and side arms.

Preferably a connection is formed in each side arm for connecting the nasal cannula to headgear for holding the nasal cannula in place on a user's head in use.

Preferably the body comprises a bridge portion, in use the bridge portion supporting the cannula on a user's upper lip region, the bridge portion providing a channel between the bridge portion and a rear extent of the nasal prongs, the channel providing a path for exhaled gases to flow.

Preferably the cross section of the channel is adjustable to adjust the distance the nasal prongs are spaced from the area of the body in contact with a user's upper lip region in use.

Preferably the cross section of the channel is adjustable by a screw received in a screw thread.

Preferably the nasal cannula comprises a single nasal prong for insertion into a user's nostril in use, the user's other nostril being vacant, and the body comprising a channel aligned with the vacant nostril for exhaled gases to flow through.

In another aspect, the present invention consists in a nasal cannula for use in a system for providing a flow of respiratory gases to a user, the nasal cannula comprising: a body made from a pliable first material comprising an inlet for receiving a flow of gases and at least one nasal prong for insertion into a user's nostril in use, the at least one nasal prong fluidly connected to the inlet, wherein the body comprises an area for contacting the user's face or nose or both, in use contact between the area and the user's nose or face or both setting the position of the prongs forwardly in the user's nostrils to provide a gap between a rear extend of the nasal prong and the back of the user's nostril, and wherein in use contact between the area and the user's nose or face or both sets the angle of the prongs in the user's nasal passage so that the flow of gases are directed towards a front wall of the user's nasal passage, and a frame made from a second material more rigid than the first material, the frame attached to or integrally formed with the body.

Preferably the at least one nasal prong is fluidly connected to the inlet via a chamber and a wall of the chamber comprising a membrane, the at least one prong extending from the membrane, the radial wall thickness of the at least one prong being greater than the membrane thickness.

Preferably the membrane is annular and surrounds the root of the nasal prong.

Preferably a radial length of the annular membrane is greater than the radial distance from an inner circumferential perimeter to an outer circumferential perimeter, the nasal prong extending from the inner circumferential perimeter.

Preferably a tip of the at least one nasal prong is angled to approximately match the angle of a nasal passage wall.

Preferably each nasal prong has an outlet for the flow of respiratory gases to flow from the cannula, and the nasal prong and outlet are arranged so that the outlet is not visible when the nasal prong is viewed from the rear and along a line parallel to where the bottom of the user's nasal passage would be relative to the prong in use.

Preferably wherein in use the outlet of each nasal prong faces the front wall of the user's nasal passage.

In another aspect, the present invention consists in a nasal interface for use in a system for providing a flow of respiratory gases to a user, the nasal interface comprising: a body made from a pliable first material comprising an inlet for receiving a flow of gases and at least one nasal outlet comprising a tubular structure for interfacing with a user's nostril in use, the at least one nasal outlet fluidly connected to the inlet, wherein at least one plastically deformable member is attached to or integrally formed with the body, the plastically deformable member having an elastic limit substantially less than the elastic limit of the first material.

Preferably a said plastically deformable member is integrally formed with the first material in a wall of a said nasal outlet.

Preferably the body comprises a pair of side arms, each side arm extending from a side of a central portion to in use pass across a user's upper lip region, and a said plastically deformable member is integrally formed with the first material of both side arms to extend across the user's upper lip region in use.

Preferably the at least one plastically deformable member is a metal wire.

Preferably the at least one plastically deformable member is a metal strap.

Preferably the nasal interface is a nasal cannula, the at least one nasal outlet is a nasal prong for insertion into a user's nostril in use.

Preferably the at least one nasal outlet is a nasal pillow for providing a seal against a user's nostril in use.

In another aspect the present invention consists in a restrictor for use in a system for providing a flow of respiratory gases to a user, the system comprising a gases source, a patient interface, a flow path between the gases source and the patient interface comprising at least one conduit, in use the restrictor providing a dominant flow restriction in the flow path such that the flow rate or pressure of the flow of respiratory gases provided by the gases source or received by the user is substantially unaffected when the conduit or patient interface is partially occluded.

Preferably the flow restrictor comprises a gradually reducing cross sectional flow area.

Preferably the restriction comprises a bullet or approximate ogive shaped piece mounted coaxially within a cylinder and supported by spokes extending from an inner surface of the cylinder, the tip of the bullet or approximate ogive shaped piece facing into the flow of gases.

Preferably the spokes extend longitudinally in an axial direction.

Preferably the restrictor is adapted to be retrofitted to an existing system.

Preferably the restrictor is fitted to a patient interface or the conduit.

Preferably the restrictor is integrally formed with a patient interface or the conduit.

In another aspect the present invention consists in a system for providing a flow of respiratory gases to a user comprising a gases source, a patient interface, a flow path between the gases source and the patient interface comprising at least one conduit, and a restrictor positioned in the flow path, the restrictor providing a dominant flow restriction in the flow path such that the flow rate or pressure of the flow of respiratory gases provided by the gases source or received by the user is substantially unaffected when the conduit or patient interface is partially occluded.

Preferably the system comprises a controller for controlling the gases source to provide a gases flow to the flow path, the controller adapted to receive a user settable input, in use the controller controlling the gases source to provide a gases flow to the flow path at a first pressure, and when the controller receives said input the controller controlling the gases source to provide a gases flow to the flow path at a second pressure, the second pressure being higher than the first pressure by an amount approximately equivalent to a pressure drop across the restrictor.

Preferably the system comprises a display for displaying information to a user, the display displaying the first pressure when the controller controls the gases source to provide a gases flow to the flow path at the second pressure.

In another aspect, the present invention consists in a patient interface for use in a system for providing a flow of respiratory gases to a user, the system comprising a gases source and a flow path between the gases source and the patient interface comprising at least one conduit, wherein the patient interface comprises a restrictor, in use the restrictor providing a dominant flow restriction in the flow path such that the flow rate or pressure of the flow of respiratory gases provided by the gases source or received by the user is substantially unaffected when the conduit or patient interface is partially occluded.

In another aspect the present invention consists in a nasal interface for use in a system for providing a flow of respiratory gases to a user, the nasal interface comprising: an inlet for receiving a flow of gases, at least one nasal outlet comprising a tubular structure for interfacing with a user's nostril in use, the at least one nasal outlet fluidly connected to the inlet, and a strap for passing over and contacting a user's nose to support the nasal interface, the strap extending from the nasal interface either side of a central location on the nasal interface.

Preferably the nasal interface comprises a pair of side arms, each side arm extending from a side of the central portion to in use pass across a user's upper lip region, a distal end of each side arm resting substantially on the front of a user's face adjacent a side of the user's nose, and the strap extending from near the distal end of each side arm.

Preferably the strap and nasal interface are integrally formed.

Preferably the distal end of each side arm is provided with a connection for attachment to head gear for holding the nasal interface in place on a user's face in use, the strap extending from each side arm adjacent each connection.

Preferably the connection is a slot for receiving a head gear strap through to attach the head gear to the side arm, the slot being substantially perpendicular to a longitudinal axis of the side arm.

Preferably the nasal interface is a nasal cannula, the at least one nasal outlet is a nasal prong for insertion into a user's nostril in use.

Preferably the at least one nasal outlet is a nasal pillow for providing a seal against a user's nostril in use.

In another aspect, the present invention consists in a nasal interface for use in a system for providing a flow of respiratory gases to a user, the nasal interface comprising: an inlet for receiving a flow of gases, at least one nasal outlet comprising a tubular structure for interfacing with a user's nostril in use, a chamber fluidly connecting the at least one nasal outlet to the inlet, wherein a wall of the chamber comprises a membrane, the at least one outlet extending from the membrane, the radial wall thickness of the at least one outlet being greater than the membrane thickness.

Preferably the membrane is annular and surrounds the root of the nasal outlet.

Preferably a radial length of the annular membrane is greater than the radial distance from an inner circumferential perimeter to an outer circumferential perimeter, the nasal outlet extending from the inner circumferential perimeter.

Preferably the membrane is shaped to be approximately a fraction of a torus, the torus being formed by rotating a closed first curve about a line in its plane but not intersecting it, the fraction of a torus being formed by truncating the torus through a plane approximately perpendicular to said line.

Preferably the membrane is shaped to be approximately a half torus formed by truncating the torus through the centre of the closed first curve.

Preferably the first curve is a circle.

Preferably the wall of the outlet extends from the inner circumferential perimeter of the fraction of a torus and the wall of the chamber extends from an outer circumference of the fraction of torus.

Preferably the wall of the outlet extends from the inner circumferential perimeter of the fraction of torus with the inside of first curve facing a tip of the outlet.

Preferably the first curve is a circle and the wall of the prong extends approximately perpendicularly to a radius of the first curve.

Preferably the first curve is a circle and the wall of the chamber extends approximately parallel to a radius of the first curve.

Preferably the membrane is shaped to be approximately a fraction of a sphere, the fraction of a sphere being formed by truncating a sphere on a first plane and a second plane, the inner circumferential perimeter being on the first plane and the outer circumferential perimeter being on the second plane.

Preferably the second plane is approximately through the centre of the sphere.

Preferably the outlet extends from a convex side of the membrane.

Preferably the nasal interface is a nasal cannula, the at least one nasal outlet is a nasal prong for insertion into a user's nostril in use.

Preferably the at least one nasal outlet is a nasal pillow for providing a seal against a user's nostril in use.

In another aspect the present invention consists in a nasal cannula for use in a system for providing a flow of respiratory gases to a user, the nasal cannula comprising: an inlet for receiving a flow of gases, at least one nasal prong for insertion into a user's nostril in use, the at least one nasal prong fluidly connected to the inlet, wherein an outlet at the tip of the at least one nasal prong is angled to approximately match the angle of a nasal passage wall.

Preferably the outlet at the tip of the at least one nasal prong is angled to approximately match the angle of the nasal passage side wall, the outlet being angled downwards from a centreline of the user's nose when viewed from the front of the user.

Preferably the angle between the nasal passage side wall and the nasal prong tip is less than 30°.

Preferably the at least one nasal prong is angled to match angle of the front of the nasal passage, the tip being angled forwardly.

Preferably the angle between the front of the nasal passage and the nasal prong tip is less than 20°.

In another aspect, the present invention consists in a nasal cannula for use in a system for providing a flow of respiratory gases to a user, the nasal cannula comprising: an inspiratory flow path comprising an inlet for receiving a flow of gases, at least one nasal prong for insertion into a user's nostril in use, the at least one nasal prong fluidly connected to the inlet, wherein a noise suppression material is provided in the inspiratory flow path.

In another aspect, the present invention consists in a nasal cannula for use in a system for providing a flow of respiratory gases to a user, the nasal cannula comprising: an inspiratory flow path comprising an inlet for receiving a flow of gases, at least one nasal prong for insertion into a user's nostril in use, the at least one nasal prong fluidly connected to the inlet, an expiratory flow path, in use expiratory gases flowing from the user's nostril via the expiratory flow path, wherein a noise suppression material is provided in the inspiratory flow path or the expiratory flow path or both.

Preferably the inspiratory flow path comprises a chamber fluidly connecting the inlet to the at least one nasal prong, the noise suppression material located in the chamber.

Preferably the cannula comprises a bridge portion, in use the bridge portion supporting the cannula on a user's upper lip region, the bridge portion providing a channel between the bridge portion and a rear extent of the at least one nasal prong, the channel providing the expiratory flow path.

Preferably the cross section of the channel is adjustable to adjust the distance the nasal prongs are spaced from the area of the face contacting portion in contact with a user's upper lip region in use.

Preferably the cross section of the channel is adjustable by a screw received in a screw thread.

Preferably the nasal cannula comprises a single nasal prong for insertion into a user's nostril in use, the user's other nostril being vacant, and the face contacting portion comprising a channel aligned with the vacant nostril, the channel providing the expiratory gases flow path.

In another aspect, the present invention consists in a nasal interface comprising: an inlet, at least one nasal outlet for interfacing with a nostril of a user, a chamber for fluidly connecting the inlet to the nasal prong, a bridge portion for supporting the cannula on an upper lip region of a user, a space between the bridge portion and the chamber providing an air gap between the chamber and the user's upper lip region.

Preferably the distance between the bridge portion and the chamber is adjustable to adjust the distance the chamber is spaced from the user's upper lip region in use.

Preferably the distance between the bridge portion and the chamber is adjustable by a screw received in a screw thread.

Preferably the nasal interface is a nasal cannula, the at least one nasal outlet is a nasal prong for insertion into a user's nostril in use.

Preferably the at least one nasal outlet is a nasal pillow for providing a seal against a user's nostril in use The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples only.

BRIEF DESCRIPTION OF THE DRAWINGS

Preferred embodiments of the invention will be described by way of example only and with reference to the drawings.

FIGS. 5A to 5D are various embodiments of headgear for use with a nasal cannula.

FIG. 17 is a cross sectional view of a flow restrictor according to another embodiment of the present invention.

FIG. 18 is a perspective view of the restrictor of FIG. 17.

FIG. 19 is an end view of the flow restrictor of FIG. 17.

FIG. 20 is a perspective view of a nasal cannula comprising plastically deformable members according to another embodiment of the present invention.

FIGS. 21A to 21E are sectional views of various forms of a nasal cannula comprising a membrane from which the nasal prong extends according to another embodiment of the present invention.

DETAILED DESCRIPTION OF THE PREFERRED EMBODIMENT

A preferred form of nasal interface arrangement is described below with reference to use as part of a patient interface for use in a medical gases system. It should be noted that the nasal interface arrangement can be used with any suitable system that provides a gases stream from a gases source to a patient in use. For example, it could be used as part of a system to provide supplementary oxygen to a user, with the oxygen provided from a source such as a gas bottle or wall outlet. However, it is described below by example for use in a system that provides a heated, humidified, gases stream to a patient or user. The nasal interface is suitable for use in the home or in a hospital environment. The nasal interface can be varied in size (with the proportions kept generally the same) for use with users of different sizes. For example, two (or more) different sizes could be produced for adult and infant users, but still fall within the scope of the present invention.

Figure 1:
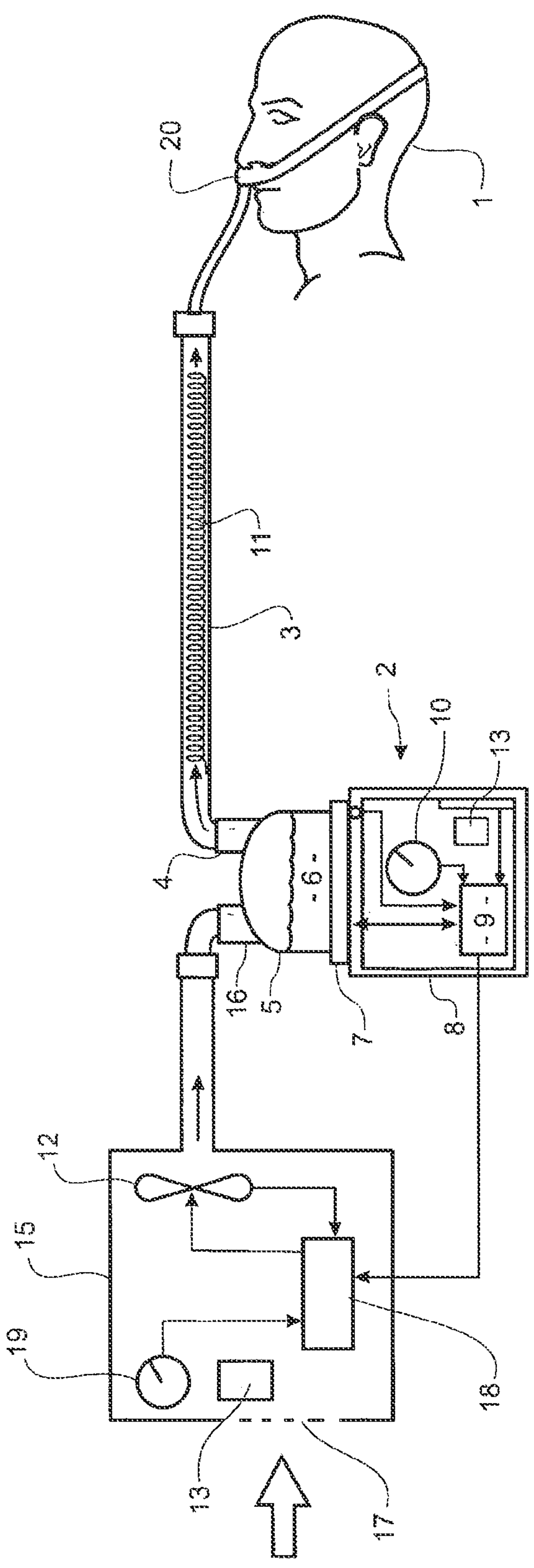
FIG. 1 is a schematic of a respiratory humidification system that comprises a gases source unit, a humidifier connected to the gases source unit, a gases supply conduit connected to an outlet of the humidifier, and a patient interface connected to an outlet of the supply conduit to provide a flow of gases to a user.

Referring to FIG. 1 a respiratory humidification system such as might be used with a preferred embodiment of nasal interface arrangement is shown. A patient or user 1 is receiving a humidified stream of gases through a patient interface 20 which includes the nasal interface arrangement and which will be described in detail below. The patient interface 20 is connected to a delivery conduit 3, the delivery conduit 3 being connected between a humidifier unit 2 and the patient interface 20. The humidifier unit 2 consists of a humidification chamber 5 that in use contains a volume of water 6, and a base unit 8. The preferred embodiment of humidification chamber 5 is formed from a plastics material and in the preferred embodiment includes a conductive base (for example aluminium) which is in direct contact with a heater plate 7 of the humidifier base unit 8. The humidifier base unit 8 is in the preferred embodiment provided with a control mechanism or electronic controller 9 which comprises a microprocessor based controller executing computer software commands stored in the controller's memory.

In the preferred form as shown in FIG. 1, the humidifier 2 receives gases from a gas source unit 15, the gases becoming heated and humidified as they pass through the chamber 5. It should be noted that as outlined above, the gas source unit 15 could be replaced or supplemented by a wall port or a gas bottle. The gas source unit could be a gas bottle, a gas blender, a venturi device or a standard blower unit, or any other suitable system or device that supplies a gases stream. Humidified gases flow from the humidifier 2 through the delivery conduit 3 to the patient by way of the patient interface 20.

It should be noted that the system used with the nasal interface does not require the use of a humidifier—that is, the gases stream could be dry and unheated if required. Various types of therapy can be delivered by using the nasal interface. The preferred form of therapy will be described later. Generally any gases and respiratory gases delivery system can be used with the nasal interface. The respiratory humidification described here is just an example of the type of therapy and system the nasal interface can be used with or as part of.

The controller 9 receives inputs from sources such as user input via dial 10, through which a user of the device may, for example, set a predetermined required value of humidity or temperature of gases supplied to the patient 1. In response to the user input or input from any other possible inputs like sensors (for example temperature or humidity sensors, not shown), the controller 9 determines when to and what level to energise the heater plate 7 to heat the water 6 within the humidification chamber 5. As the volume of the water 6 within the humidification chamber 5 is heated, water vapour begins to fill the remaining volume of the humidification chamber 5. The gases which are provided to the humidifier unit 2 from the gas source unit 15 enter the humidification chamber 5 above the surface of the water 6, and are humidified by the water vapour within the humidification chamber as they pass through the chamber 5. The heated humidified gases exit the humidification chamber 5 through an outlet 4 and are transferred to the patient interface 20 by the delivery conduit 3.

By example, the gas source unit is a blower unit. The preferred form of blower 15 is provided with a variable speed pump or fan 12 which draws air or other gases through a blower inlet 17. The speed of the pump or fan 12 is in the preferred embodiment controlled by a further control apparatus 18. Alternatively control of the pump or fan speed can be carried out by controller 9. The fan controller 18 can also be adapted to receive inputs from sensors in the system, or a user input from a control panel or control unit 19. As noted above, the blower unit 15 can be supplemented by or replaced by a gases source such as a gases bottle or a wall-mounted outlet connected to a central gases source. Alternatively the blower unit and humidifier unit may be packaged into a single integrated blower and humidification unit.

The preferred system also comprises a user display 13 for communicating information to a user such as operating mode selection and operating parameters such as actual pressure or flow provided by the blower, temperature of gases flow, humidity of gases flow, compliance hours of use and other information useful to a user.

The preferred form of delivery conduit 3 includes a heating element 11 to prevent condensation of humidified gases occurring within the conduit 3 ('rain out').

Figure 27:
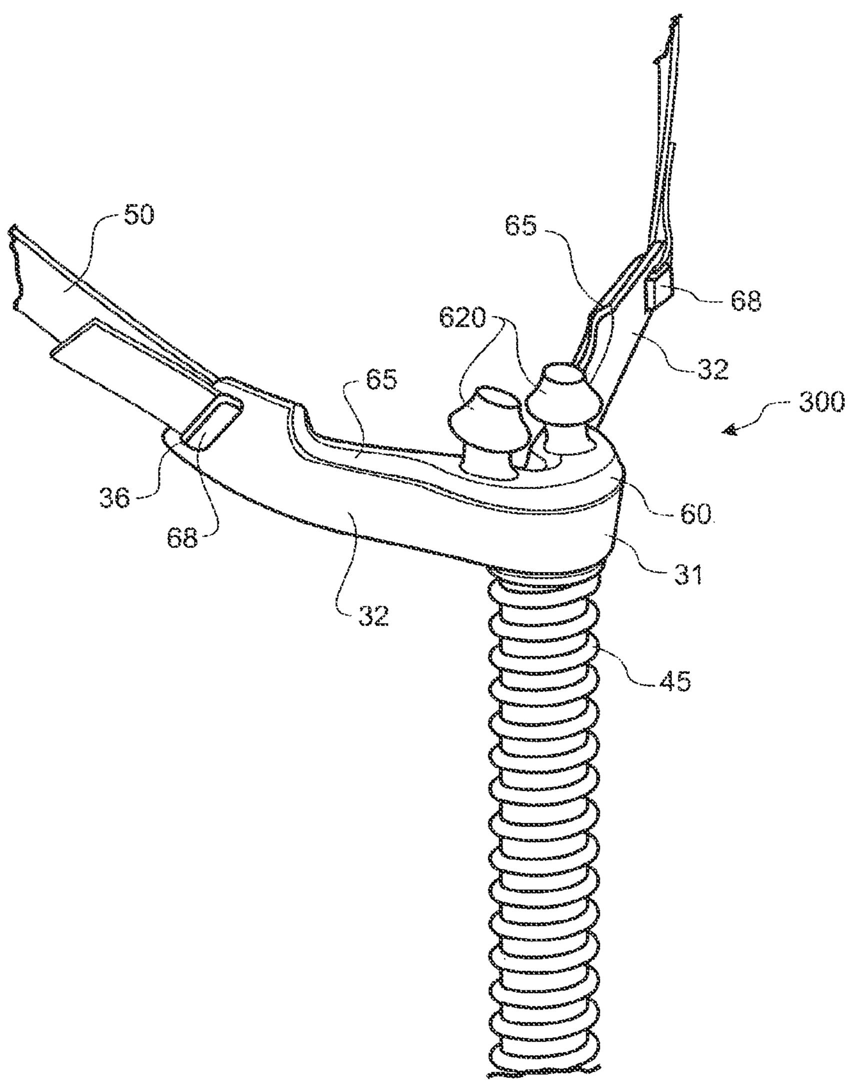
FIG. 27 is a perspective view of a nasal interface including nasal outlets with pillows according to one embodiment of the present invention.

The preferred form of humidification system has been described above, with the nasal interface described as being included as part of the patient interface 20. Various inventions relating to nasal interfaces are described below with reference to nasal cannulae. However, one or more inventions described and claimed below may be useful in nasal interfaces comprising nasal outlets with pillows for providing a seal at the user's nostrils. Inventions are described with reference to nasal cannulae by way of example only. An alternative patient interface 200 including nasal outlets with pillows 620 according to one or more present inventions is shown in FIG. 27.

Patient Interface

Figure 2:
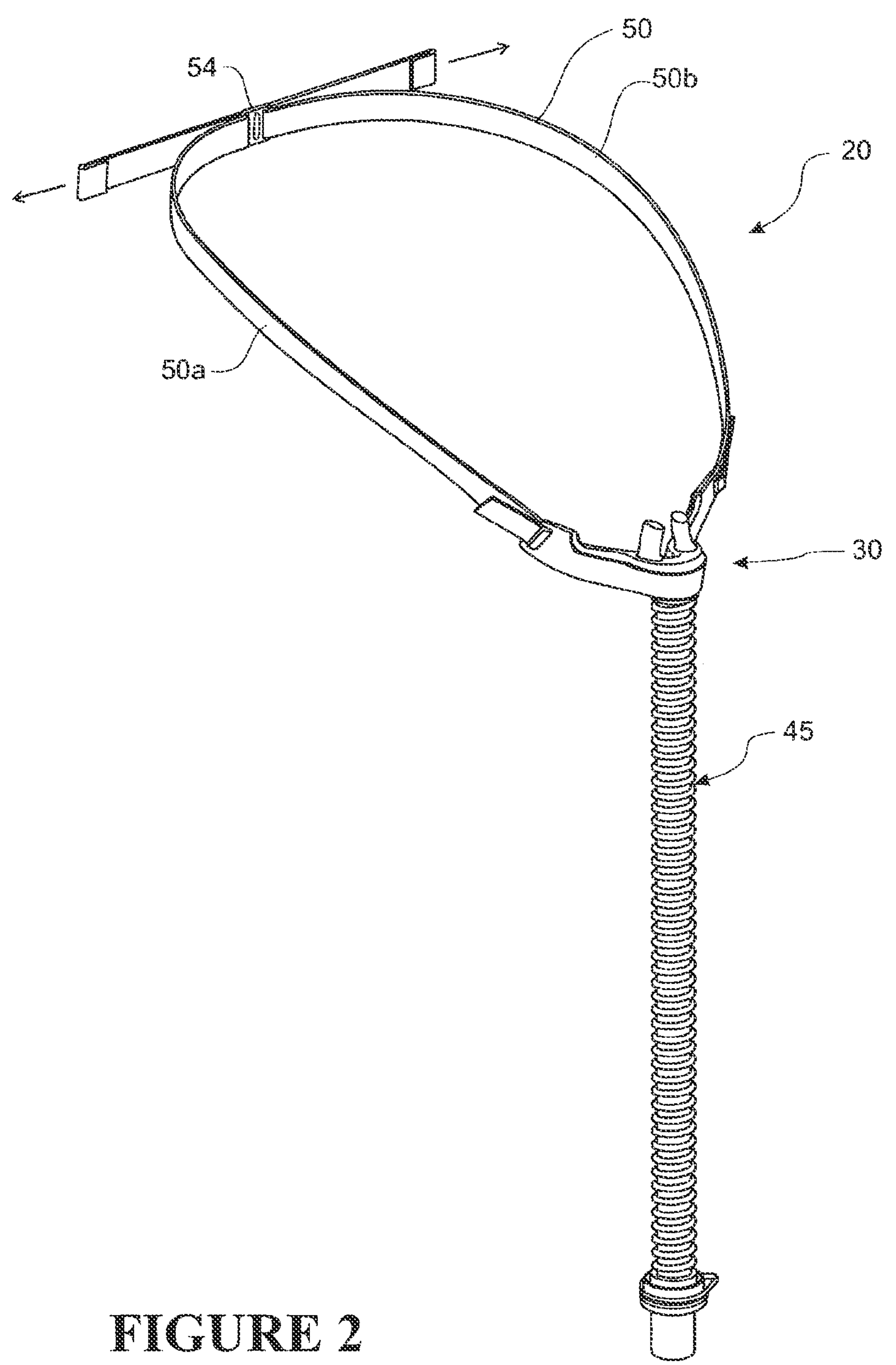
FIG. 2 is a perspective view of a nasal cannula according to one embodiment of the present invention.

FIG. 2 shows the first embodiment of the patient interface 20 of FIG. 1 in more detail. The patient interface 20 broadly consists of a head securement mechanism and a nasal cannula 30. A gases inlet conduit or secondary supply conduit 45 is also shown. The head securement mechanism enables a user to place and maintain the nasal cannula 30 in the correct operational position. The gases inlet conduit or secondary supply conduit 45 gaseously or fluidly connects between the outlet end of the main delivery conduit 3 and the nasal cannula 30. The secondary supply conduit 45 and the nasal cannula 30 will be described in detail below.

Head Securement

In the preferred embodiment, the patient interface 20 is secured to the patient's head or face by a strap 50, as shown in FIG. 2. The strap 50 in use connects with a side of the nasal cannula 30, passes around the back of the users head to connect to the other side of the cannula 30. In use the strap 50 preferably passes across each side of the user's head above each ear. The strap 50 may be a single strap, each end of strap 50 connected to a respective side of the cannula.

The most preferred form of head strap device is adjustable to allow patients of different sizes and head shapes to use the nasal cannula 30. For example, an adjustment buckle could be included which allows a patient to loosen or tighten the head strap 50.

Preferably the strap 50 comprises two separate straps 50*a* and 50*b*. As shown in FIG. 2, each strap 50*a* and 50*b* is connected between a respective side of the cannula 30 and a respective side of a buckle 54. In use, buckle 54 is positioned towards the back of the users head. In this position, excess strap length is maintained away from the user's face, preventing loose ends of straps 50*a* and 50*b* touching the user's face.

Figure 3:
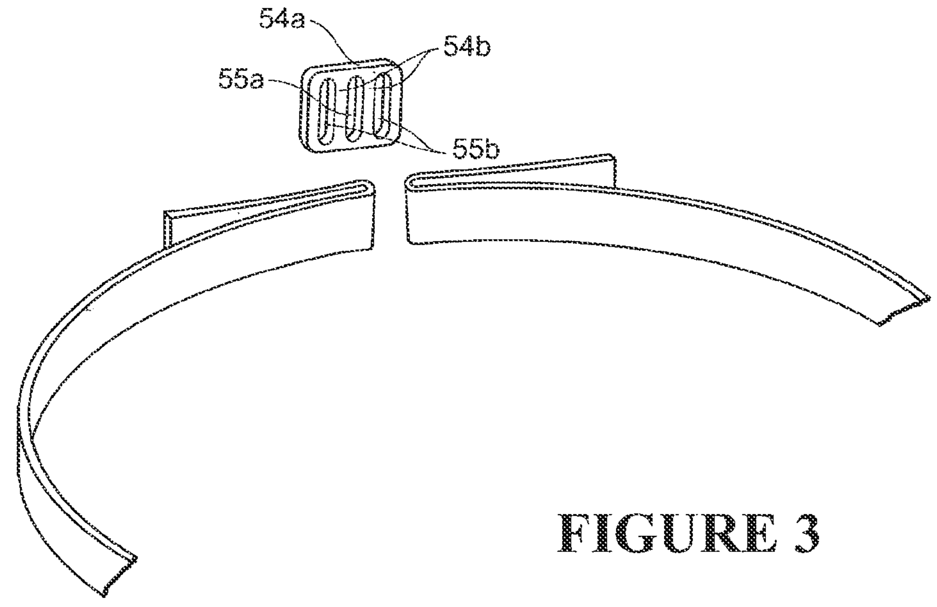
FIG. 3 is a part perspective view of a head gear strap for use with a patient interface according to another embodiment of the present invention.

As best shown in FIG. 3, buckle 54 comprises a perimeter frame 54*a* and two cross pieces 54*b*. Cross pieces 54*b* are substantially vertical and substantially parallel to the sides of the perimeter frame 54*a*. Cross pieces 54*b* and frame 54*a* are arranged to form three substantially vertical slots 55. A central slot 55*a* may be approximately double the thickness of side slots 55*b*, side slots 55*b* arranged either side of the central slot 55*a*. In use straps 50*a* and 50*b* extend from a respective side of the cannula assembly 30 to both pass through the central slot 55*a*. Each strap loops about a respective cross piece 54*b* to pass through a respective side slot 55*b*. Loose ends of straps 50*a* and 50*b* are positioned on an outer side of the portion of straps 50*a* and 50*b* extending between cannula 30 and buckle 54. The buckle 54 allows a patient to loosen or tighten the side straps in order to achieve a comfortable fit. Loose strap ends may be pulled away from the buckle 54 as indicated by the arrows in FIG. 2 to tighten the cannula assembly into position adjacent the upper lip of the user. Preferably the strap 50 or straps 50*a* and 50*b* are elastic and can be stretched over a patient's head. The elasticity of the straps exerts a force upon the head to hold the nasal cannula in the optimal position when in use.

The buckle 54 is particularly flat and small so that the user does not feel the buckle in use, even when the weight of the user's head rests on the buckle where the buckle is positioned between the user's head and the user's bedding.

Figure 4:
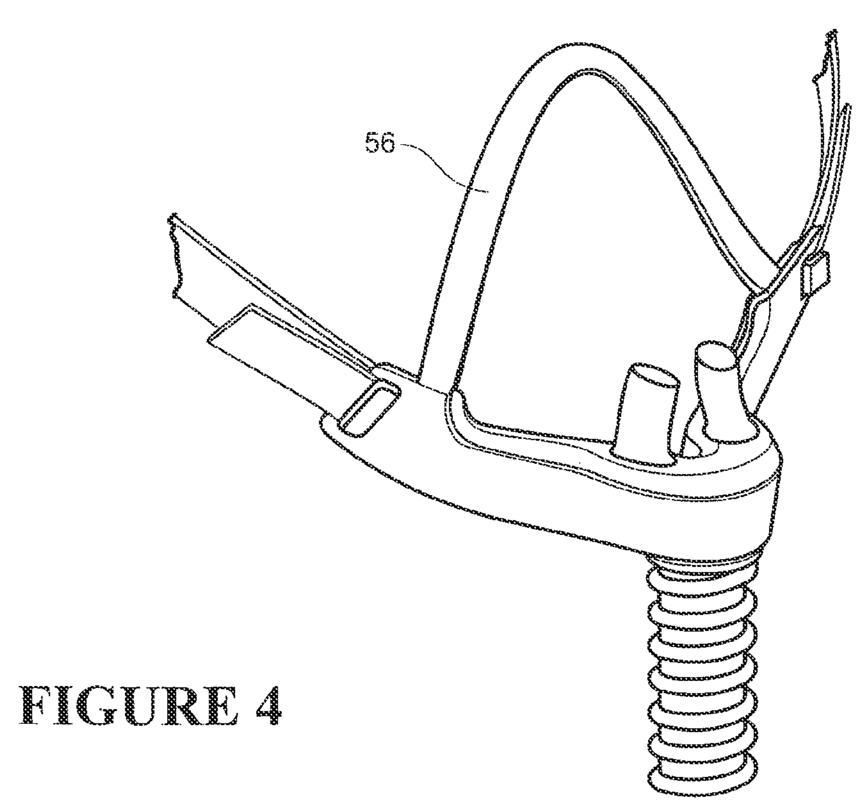
FIG. 4 is a nasal cannula including a strap for passing over a user's nose in use to support the cannula according to another embodiment of the present invention.

The head securement mechanism may further comprise a loop 56 that passes over the user's nose in use, as shown in FIG. 4. The loop 56 is configured to pass over a patient's nose to support the weight of the cannula 30. Preferably the loop 56 passes over the bridge of the user's nose. The loop 56 is connected to the nasal cannula either side of a central location on the nasal cannula. The loop 56 is preferably elastic. The elasticity of the loop exerts a force upon the nose to hold the nasal interface in the optimal position when in use. Alternatively the loop is not elastic. For example, the loop 56 may be integrally formed with a moulded component of the nasal cannula.

FIGS. 5A to 5B illustrate further alternative embodiments of headgear for use with a nasal cannula. The headgear of FIG. 5A includes a crown strap 57 in addition to strap 50. The crown strap 57 passes over the top of the user's head to assist with securing the nasal cannula in place correctly. Preferably the strap 57 is elastic to suit a range of different users. The crown strap 57 may comprise a buckle to provide adjustment to suit a range of different users.

The cannula illustrated in FIG. 5B comprises side arms 32 that extend towards the rear of the user's head and in use pass over the user's ears. A strap 50 extends from a distal end of side arms 32 to pass around the rear of the user's head. The side arms are integrally formed with a moulded component of the cannula. The side arms are preferably made from an elastomer or thermoplastic material. Strap 50 connects between a left and right side arm 32. The strap 50 may comprise at least two parts joined by a buckle for adjustment. Alternatively, as shown in FIG. 5C, the cannula side arms may combine to form a continuous loop 132 that passes fully around the user's head for use without a strap 50. The loop 132 is integrally formed with a moulded component of the nasal cannula 30. The loop 132 may not be continuous, for example two sides of the loop joining via an adjustment buckle.

The headgear of FIG. 5D includes a widened portion 58. In use widened portion 58 contacts over an area of the back of a user's head. The widened portion 58 may diverge from a side strap 50 on one side of the user's head into two or more spaced apart straps at the back of the user's head before converging to a single strap on the opposite side of the user's head.

Gases Inlet Conduit

The secondary supply conduit 45 will now be described in detail. The secondary supply conduit 45 is a short length of conduit or tubing which runs between the outlet of the main delivery conduit 3 and the nasal cannula 30. In use, gases exit the main delivery conduit 3 and enter the secondary supply conduit 45, to flow along the secondary supply conduit 45 to the patient. One reason that a secondary conduit is used is as follows: the main delivery conduit 3 is relatively heavy and cumbersome as it is used to transport gases over a reasonably long distance (from the humidifier unit 2 to a point close to the patient). The main delivery conduit 3 is therefore required to have a wall that is strong enough to support its own weight without collapsing. As the main delivery conduit 3 is therefore relatively long (e.g. 2 to 3 metres), this additional length and the thicker wall structure adds to the weight of the main delivery conduit 3. If the outlet of the main delivery conduit 3 is connected directly to the patient interface in such a manner that the user 2 is required to support this weight, this can cause discomfort to the user due to the weight of main delivery conduit acting on the user. A lighter, shorter secondary conduit (e.g. secondary supply conduit 45) is therefore frequently used, running between the outlet of the main delivery conduit 3 and the patient interface 20. Secondary supply conduit 45 is lighter and shorter than the main delivery conduit 3.

In order to reduce condensate forming in the unheated secondary supply conduit 45, a conduit that has vapour transmission properties can be provided. The secondary supply conduit 45 can be integrally formed with the main delivery conduit 3 or may be attached by some connection mechanism, allowing for detachment of the secondary supply conduit 45 from the main delivery conduit 3. The connection mechanism can be a threaded screw type connector or a friction locking mechanism. The secondary supply conduit is preferably made from a hydrophilic material, for example SYMPATEX.

The secondary conduit may, for example, be approximately 300 mm long. The result of providing a short secondary supply conduit 45 is that a majority of humidity in the gases is transported to the patient, and there is an insignificant and immeasurable loss of humidity through the breathable wall of the short secondary supply conduit, while condensate forming is reduced.

The secondary conduit 45 preferably has a smaller diameter than the conduit 3. For example, the secondary conduit may have an internal diameter of approximately 11 mm and the conduit 3 may have an inner diameter of approximately 16 mm.

The nasal cannula and its various features will now be described in more detail.

Nasal Cannula

The preferred form of the nasal cannula 30 that forms part of the patient interface 20 shall now be described in more detail with particular reference to FIGS. 6 to 9.

The preferred cannula assembly comprises two main parts, a resilient, flexible, pliable cannula body and a clip or frame that provides support or structural strength to the cannula assembly. Preferably the body contacts the user's face in use, for example an upper lip region of the user's face.

The cannula body 60 comprises a manifold 61 and a nasal prong or nasal prongs 62. Each nasal prong extends into a user's nostril in use. The manifold has an inlet or aperture 63 for receiving a conduit. Preferably the aperture is sized to receive a secondary conduit as described above. Alternatively the inlet may be adapted to receive the conduit 3. However this is less preferred. The aperture or inlet is fluidly connected to a nasal prong or pair of nasal prongs. In use, a respiratory gases flow provided to the cannula assembly via the conduit connected to the cannula assembly enters the cannula assembly via the inlet, passes through the manifold to exit each prong to enter the user's nostrils.

The nasal prongs do not seal to the nostrils of the user. Where the user exhales via his or her nostrils, exhaled gases pass out of the nostrils via clearance between the inner wall of the nostrils and the outside of the nasal cannula prongs.

A conduit for connection to the cannula comprises a connector 40 for attachment to the nasal cannula assembly. Preferably connector and matching aperture are circular. However, other shapes may be substituted, for example an oval shape. The connector 40 is fitted to an end of the conduit and may be considered to be a part of the conduit or an end of the conduit. For example an outer diameter of the connector may be received in an internal diameter of the conduit. The connector may be bonded or moulded to the conduit.

The connector 40 comprises a groove or a circumference 41 located between a first lip or surface 42 extending radially from the connector and a second lip or surface 43 extending radially from the connector. Groove 41 is annular and extends around the circumference of connector 40. Preferably the first lip and second lip extend fully around the circumference of the connector. Alternatively, the first and second lip 42, 43 may extend for a portion of the circumference of the connector 40.

The manifold 61 further comprises an internal groove 64 extending around the perimeter of the aperture. In use the first lip 42 is received in the manifold groove 64, fluidly connecting the conduit to the manifold of the cannula body.

In the preferred embodiment of the nasal cannula, the manifold inlet is oriented to face downwards when a user is wearing the nasal cannula in a standing position. With the conduit connected to the cannula body, the conduit can hang downwards from the cannula. With the user in a standing position, the nasal pongs extend upwards from a top surface of the cannula body.

As the cannula body is made from a resilient, flexible, pliable material, the aperture is easily stretched over the first lip 42 of the conduit connector so that the lip 42 seats within the groove. The fit between the groove and the lip 42 is preferably a tight fit. However, because the body is a flexible and made from a resilient and pliable material, the conduit connector can be twisted relative to the cannula body.

The cannula body preferably further comprises side arms 65. Each side arm extends from a side of a central portion of the cannula body and in use passes across a user's upper lip region to terminate adjacent a corresponding cheek region. Preferably each side arm is angled slightly backwards from the central portion towards the face of the user in use, and angled upwards so that the side arms each extend from the central portion on a line that passes near the top of each ear. In use the ends of the side arms distal from the central portion rest substantially on the front of a user's face adjacent a side of the user's nose where the user's upper lip region terminates.

Preferably the cannula body 60 comprising the side arms, manifold and nasal prongs is an integrally formed flexible, resilient, pliable unit. Preferably the cannula body is made from silicone with a Shore A hardness of between 10 and 60. However, any other suitable pliable material with similar properties may be used.

In use head gear (described above) is coupled adjacent to the distal ends of each side arm to hold the nasal cannula assembly in place on a user's face. With appropriate connections provided to each side arm, in use the nasal cannula 30 may comprise only the integrally formed cannula body, attached to the conduit 3 or 45 and the head gear. However, the preferred cannula embodiment is an assembly further comprising the frame or clip 31.

The frame 31 provides support to the cannula assembly 30 and helps to secure the conduit connector 40 to the cannula 30. Without the frame, the connector 40 is retained within the aperture of the cannula body by first lip 42 of connector 40 residing within the groove in the resilient and pliable material of the cannula body only. In this case, only a relatively small axial force is required to pull the connector away from the manifold, to deform the pliable aperture over the first lip 42 of connector 40.

The frame is formed from a relatively stiff material; a material that has a higher stiffness compared to the resilient, flexible or pliable cannula body. For example, the frame is formed from a suitable rigid or semi-rigid material such as a polycarbonate plastic, a polypropylene plastic or other suitable material. The pliable cannula body can be deformed easily, for example a portion of the cannula body can be bent to be doubled over on itself without noticeable plastic deformation. In contrast, the rigid or semi rigid frame is capable of elastic deflection, but the frame has a significantly higher Youngs Modulus compared to the cannula body. A portion of the frame cannot be bent over on itself without plastic deformation. The cannula body material is softer than the frame material.

Figure 7:
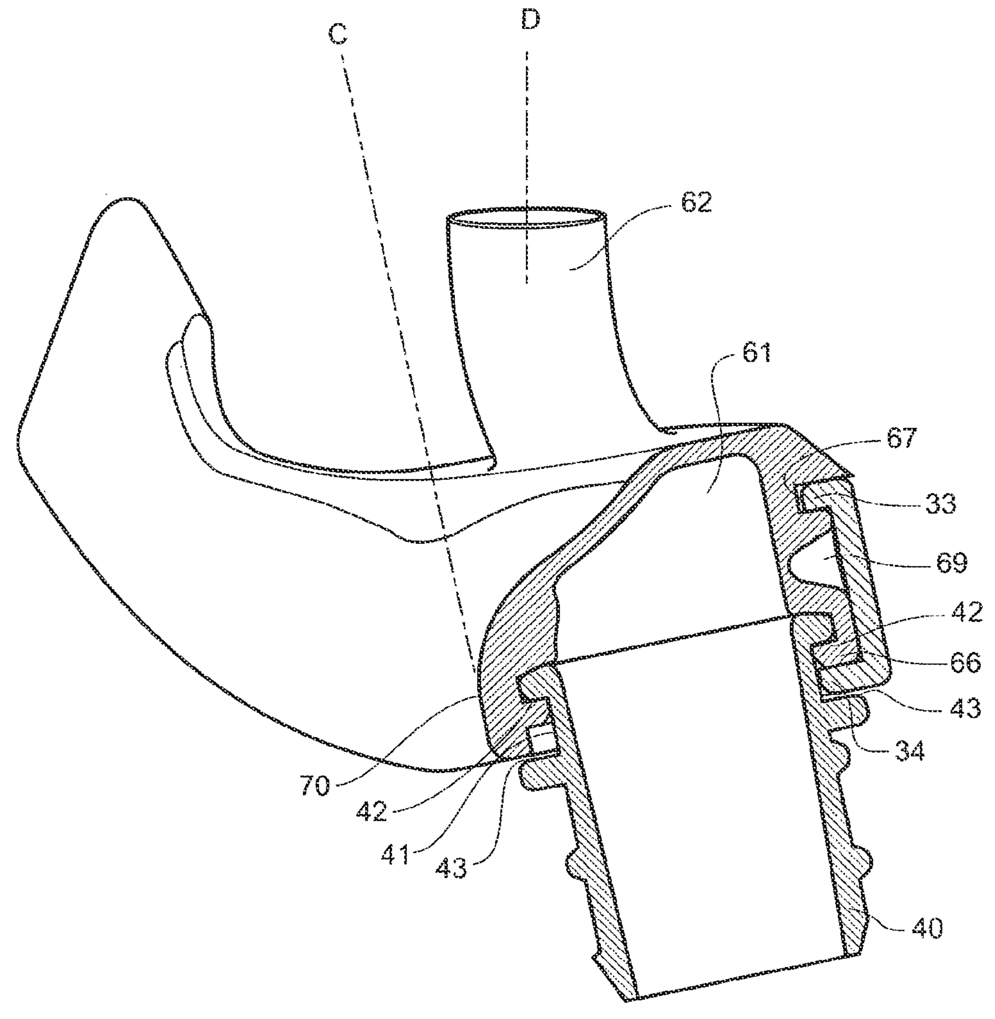
FIG. 7 is a cross sectional view of the nasal cannula of FIG. 2.
Figure 8A:
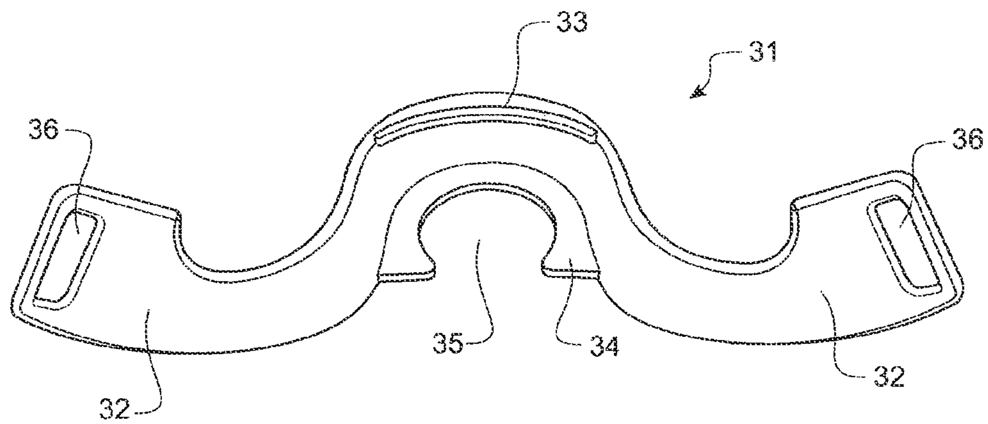
FIG. 8A is a perspective view of a frame of the nasal cannula of FIG. 2.
Figure 8B:
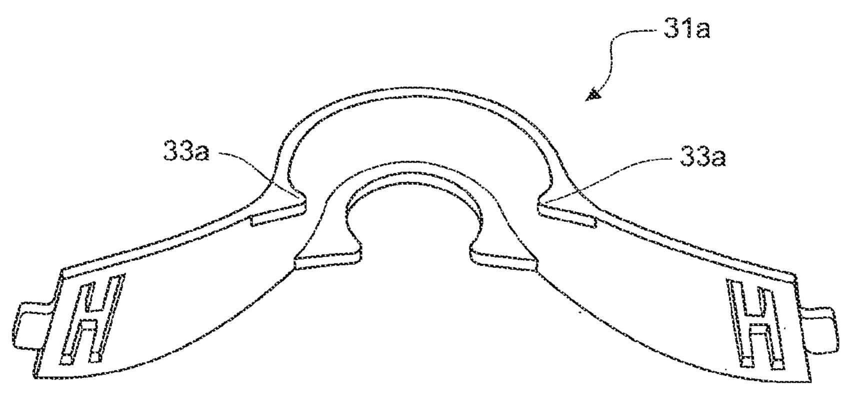
FIG. 8B is a perspective view of an alternative frame.
Figure 9:
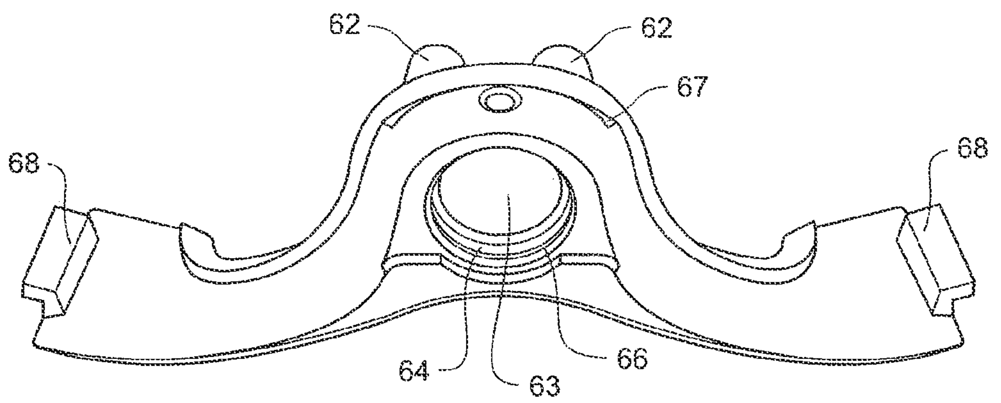
FIG. 9 is a perspective view of a face contacting portion of the nasal cannula of FIG. 2.

The frame 31 comprises an at least one first projection and an at least one second projection. The first projection engages to the conduit connector. As best shown in FIGS. 7 and 8, preferably the first projection is a flange 34 that secures within the groove 41 of conduit connector 40, between the first lip 42 and second lip 43 of conduit connector. When correctly assembled, a rim 66 of aperture 63 (refer FIG. 9) is sandwiched between the first lip 42 of connector 40 and flange 34 of frame. When correctly assembled, rim 66 and flange 34 are sandwiched between the first and second lip 42, 43 of connector 40.

In the preferred embodiment the flange 34 is substantially perpendicular to the axis of conduit connector 40. The flange 34 comprises a hole 35 for clasping about the groove of connector 40. The hole 35 is circular and is open on one side for receiving connector 40. The internal diameter of hole 35 matches the external diameter of groove 41 such that a loose fit is achieved between the groove 41 and hole 35 when connector 40 is received in hole 35. The width of the opening in the side of the hole is less than the diameter of the groove 41. To attach frame 31 to connector 40, connector 40 is pushed via the opening into hole 35. The frame is elastically deformed to spread the opening wide enough to receive the groove of connector 40 during attachment of the connector to frame 31. Once the connector is located within the hole, with the centres of the hole and connector substantially aligned, the frame returns to its undeformed state, radially capturing the connector groove within hole 35. The first and second lip 42 and 43 of connector 40 rest either side of flange 34 to retain the connector within the flange of frame 31 in a direction along the axis of the connector. The matched diameters of the hole 35 and the groove 41 allow the connector to swivel or rotate about the axis of the conduit. The conduit may be detached from the frame by spreading the opening of hole 35 to allow the groove to pass via the opening.

As described previously, the aperture of the cannula body is fitted over the first lip 42 of the connector 40. Thus the cannula body is radially captured on the connector 40.

To securely retain the cannula body on the connector 40 in an axial direction, the frame comprises the at least one second projection. The second projection engages to the face contacting portion. Without the second projection, the cannula body could be pulled axially away from the connector 40 relatively easily. In the assembled cannula assembly, the second projection 33 is received in a corresponding recess 67 in the cannula body, as best shown in FIG. 7. The engagement of the second projection in the recess prevents relative axial movement between the cannula body and the frame. As frame 31 is axially coupled to connector 40 by flange 34 flange 34 engaged around groove 41, the frame therefore couples the cannula body to the conduit connector 40 in an axial direction.

The second projection is preferably a second flange that is received in a corresponding recess in the cannula body. Preferably the second flange extends substantially perpendicular to the axis of the connector 40. With the second projection received in the recess, the cannula body is securely retained in an axial direction.

Alternatively, the second projection may be a peg to be fitted into a corresponding hole in the cannula body, or any other projection to be received in a corresponding recess.

To assemble the cannula assembly together, in a first step the cannula body 60 is attached to connector 40 of conduit 3 or 45, by stretching the rim 66 of the inlet aperture of the manifold over the first lip 42 of connector 40. In a second step, the frame is pushed in a direction substantially perpendicular to the axis of connector 40, to capture the first projection or flange 34 of frame around the groove 41 of connector 40, while simultaneously engaging the second projection 33 of frame 31 with recess 67. To disassemble the cannula assembly the first and second steps are reversed.

Alternatively, the cannula body and frame may be assembled together in a first step. In a second step the connector may be attached to the frame and cannula body by pushing the connector into the hole in a direction along the axis of the conduit. For example, as shown in FIG. 6, the upper lip 42 of connector 40 may have an upper surface **42*a* that is inclined to the axis of connector 40 to assist with pushing the connector into the hole 35 and 63. However this assembly method is less preferred Alternatively, the frame may be attached to the connector 40 in a first step. In a second step, the cannula body is pushed axially onto the first lip of connector 40** and the second projection of frame is eased into the recess in the cannula body. However this assembly method is the least preferred.

The frame may comprise a plurality of first projections and a plurality of second projections. For example, in alternative embodiment of FIG. 8B, the frame has two second projections **33*a***.

In the preferred embodiment the frame 31 further comprises side arms 32. The frame side arms, first projection and second projection are preferably integrally formed. Each side arm extends from a central portion and in use passes across a user's upper lip region to terminate adjacent a corresponding cheek region. Preferably each side arm is angled slightly backwards from the central portion towards the face of the user in use, and angled upwards from the central portion so that the side arms each extend on a line that passes near the top of each ear. In use the ends of the side arms distal from the central portion locate substantially at the front of a user's face adjacent a side of the user's nose where the user's upper lip region terminates.

In the preferred embodiment, in use, the cannula body side arms 65 rest in between a user's face and the frame side arms 32. As described above, the material of the cannula body is softer than the frame material. The cannula body provides a cushion between the frame 31 and the user's face.

The distal end of each frame side arm 32 is provided with a connection for attachment to the head gear for holding the cannula in place on a user's face. Preferably each frame side arm includes a slot 36 for passing a strap 50 of the head gear through, to attach the head gear to the frame. Preferably the slot is substantially perpendicular to a longitudinal axis of the side arm, so that a longitudinal axis of the strap extends approximately in line with the longitudinal axis of the frame side arm. Alternatively the head gear may be attached to the cannula via a quick release connector provided with one or both side arms for quickly disconnecting the head gear from at least one side of the cannula 30.

In the preferred cannula assembly, each cannula body side arm 65 comprises a retainer for attaching the cannula body side arm to the corresponding frame side arm. For example, the cannula body side arm may include a peg extending from a surface of the side arm facing the frame. The peg is received in a corresponding hole in the frame side arm. Interference between the peg and the corresponding hole retains the cannula body side arm in proximity with the corresponding frame side arm.

Figure 6A:
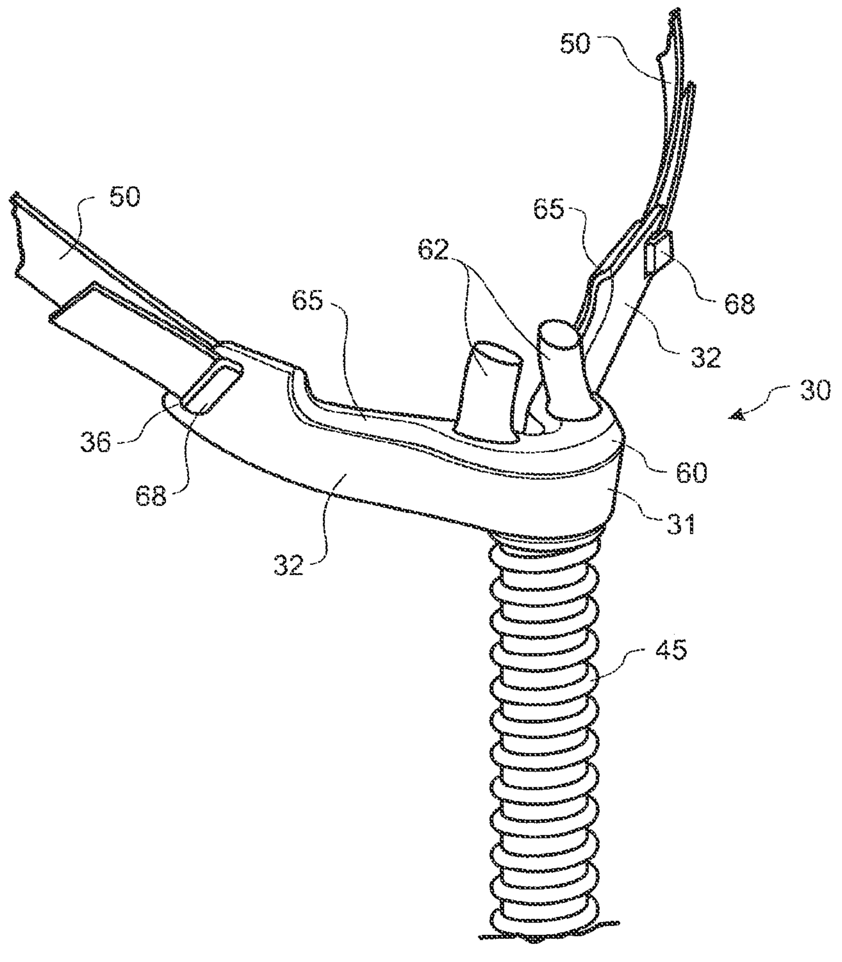
FIG. 6A is the nasal cannula of FIG. 2 shown in more detail.
Figure 6B:
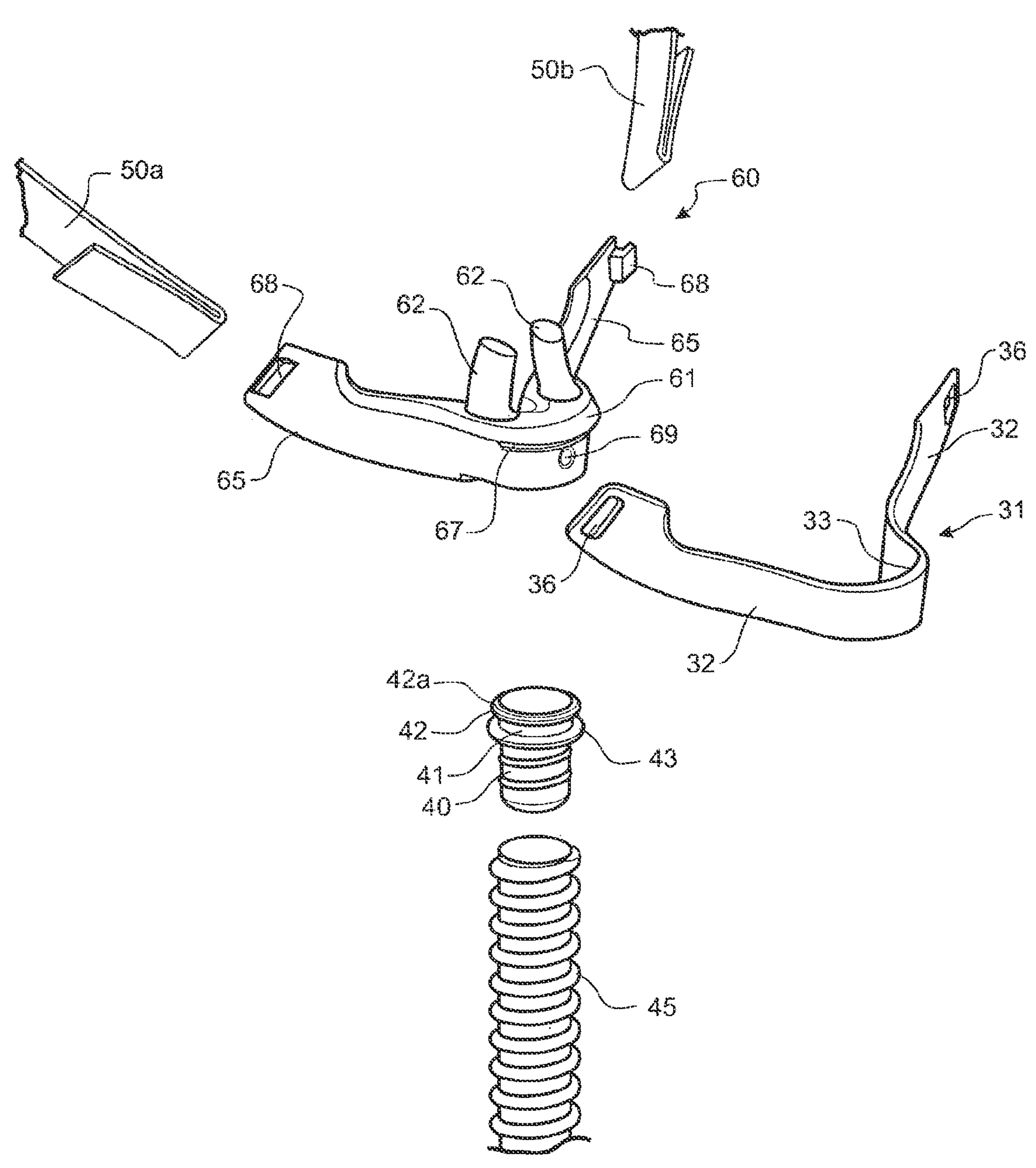
FIG. 6B is an exploded view of the nasal cannula of FIG. 2.

In the preferred cannula assembly as shown in FIGS. 6A and 6B, each cannula body side arm includes a tab 68 that is received in a corresponding slot in the frame side arm to retain the cannula body side arm relative to the corresponding frame side arm. Preferably the slot that receives the tab is slot 36 that receives the head gear strap, the tab 68 being located at a distal end of the cannula body side arm. Such an arrangement results in a simple frame part requiring only a single slot for receiving both the head gear strap 50 and the cannula body side arm tab 68. A further advantage of this arrangement is the distal end of the cannula body side arm is retained near to the head gear strap, the soft side arm and head gear strap providing an almost continuous soft interface against the users face in use. Alternatively in addition to the slot for receiving the headgear strap, an additional slot may be provided in the side arm for receiving the tab. However this alternative arrangement is less preferred.

Alternatively, frame 31 may not have side arms. In this case the headgear strap is attached to the cannula body side arms.

In a further alternative embodiment, frame 31 may not be removable or separable from the cannula body 60. For example, the frame may be integrally moulded with the cannula body.

Figures 23, 24:
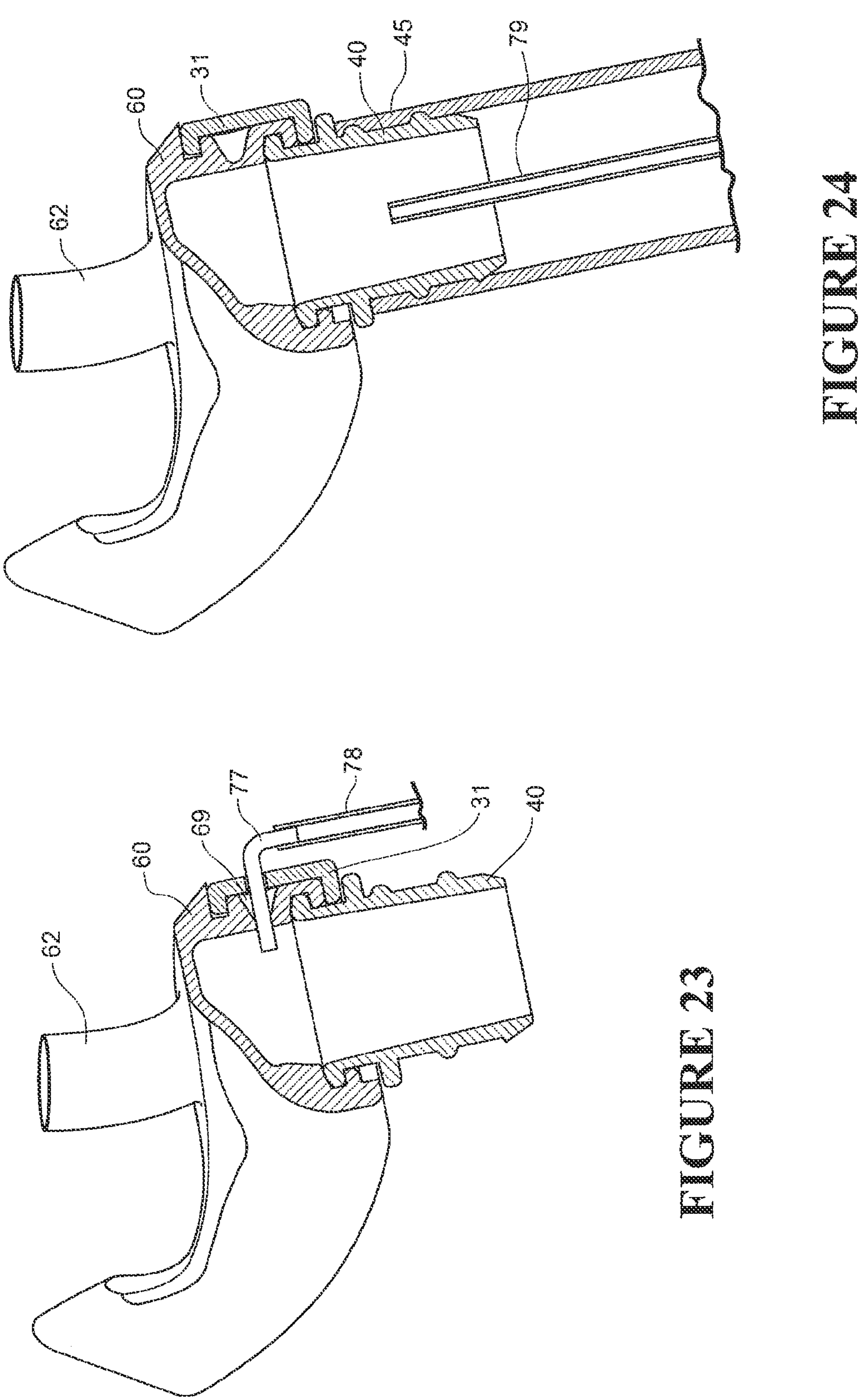
FIG. 23 is a sectional view of a nasal cannula comprising a port for a titration probe and the titration probe installed in the port according to another embodiment of the present invention.
FIG. 24 is a nasal cannula comprising a titration tube located coaxially within a gases supply conduit connected to an inlet of the cannula according to another embodiment of the present invention.

The cannula may include one or more titration ports to allow a sensor to communicate with the flow of gases at the cannula. For example, as shown in FIG. 6 and FIG. 7, the cannula body may include a recess or indent 69 for receiving a titration probe. A corresponding hole (not shown) is provided in the frame to provide access to the indent 69 on the cannula body. A suitable probe includes a spike for penetrating the wall of the face contacting potion to communicate with the inside of the cannula. The indent 69 provides a locating recess for receiving the probe, and also provides a thin wall section through which the probe can be pushed relatively easily. FIG. 23 illustrates a titration probe 77 inserted through the recess 69 to provide communication with a sensor communication conduit 78. Alternatively, the conduit 45 connected to the cannula may include a titration tube 79 arranged internally within the lumen of the conduit 45. For example, as shown in FIG. 24, titration tube 79 may be located coaxially within conduit 45. An end of the titration tube 79 is located near to the cannula inlet to provide communication between a sensor attached to the titration tube and the inside of the cannula. Such an arrangement allows a sensor to measure, for example, the pressure of the gases flow at the cannula.

Cannula Nasal Prong Orientation

Figure 10:
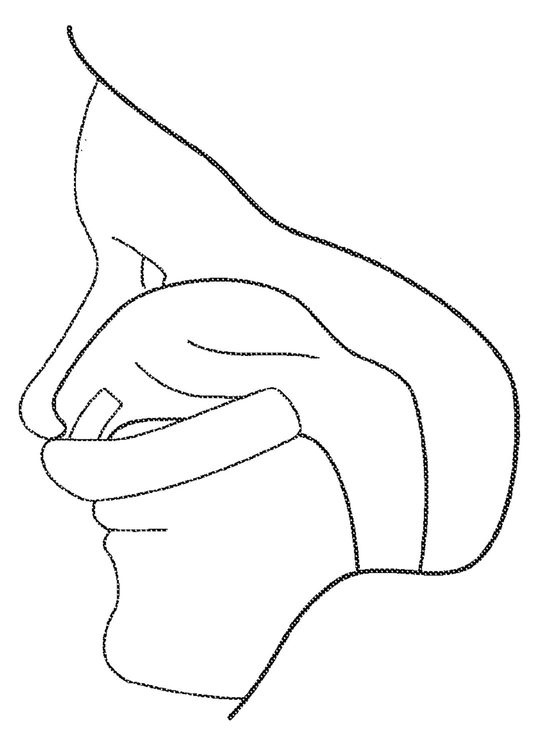
FIG. 10 is a view of a prior art nasal cannula positioned on a user's face for use, the nasal passage of the user indicated.

Prior art nasal cannula assemblies include nasal prongs that are angled or curved backwards into the user's head to match the angle of the user's nasal passages. Such an arrangement has been considered beneficial in order to provide a comfortable fit. To receive the nasal prong comfortably in the nasal passage the nasal prong is shaped to follow the nasal passage. An example of this arrangement is shown in FIG. 10.

Figure 11:
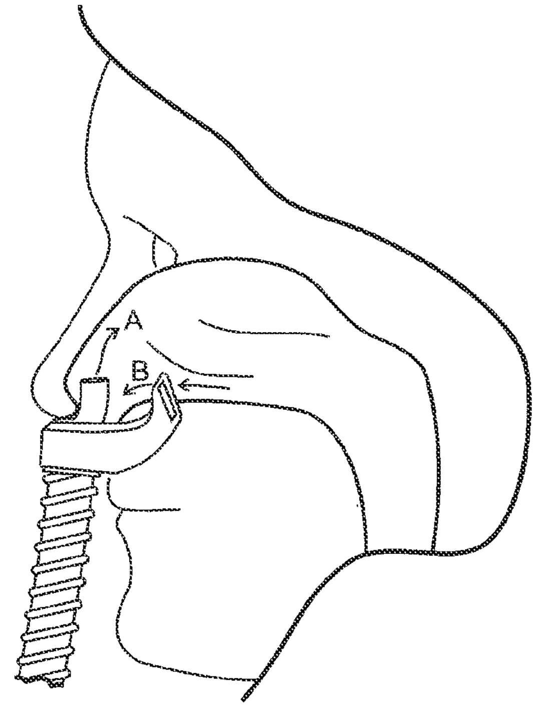
FIG. 11 is a view of a nasal cannula positioned on a user's face for use, the nasal cannula comprising nasal prongs that direct the inspiratory gases forwardly in the user's nasal passage according to another embodiment of the present invention.

However, the inventors have found the surprising result that an improvement in user comfort can be achieved with nasal prongs that are aligned towards the front of the user's nasal passage within the user's nose. The benefit of such an arrangement is a reduction in noise during use. A reduction in noise results from a reduction in flow collision between inspiratory and expiratory respiratory gases. Inspiratory gases are directed up the front of the nasal passage within the user's nose, as indicated by arrow A in FIG. 11. The inspiratory gases flow up the front of the nasal passage before flowing towards the back of the patient's nasal cavity. This inspiratory flow path leaves a space towards the rear of the nasal passage and nostril for exhaled gases to pass, as indicated by arrow B. This reduces the amount of mixing or collision between the inspiratory and expiratory gases. A reduction in the collision between inhaled and exhaled gases reduces noise during use.

Preferably in use the cannula is arranged so that a longitudinal axis of each nasal prong at the tip of each nasal prong is parallel to or angled forward of a plane, the plane being vertical when the user is in a standing position with the user's head held level.

Preferably, in use each nasal prong is arranged to direct the flow of gases towards the front wall of the user's nasal passage within the user's nose.

Preferably, in use each nasal prong is arranged to direct the flow of gases towards the front wall of the user's nasal passage within the user's nose adjacent the user's nostril.

The inventors also believe a reduction in noise is achieved by reducing the amount exhalation gases flow onto the outlet of each nasal prong. Each nasal prong provides an outlet for the respiratory gases to exit the nasal prong and enter the user's nasal passage. In the preferred cannula the outlet of each nasal prong is angled so that a plane of the outlet is parallel to or angled away from the flow path of the exhalation gases. It is thought by the inventors that the exhalation gases flow from the rear of the user's nasal passages generally along the bottom of the nasal cavity. With the user in a standing position and with his or her head held level, the bottom of the nasal passage is approximately horizontal, and the exhalation gases flow generally horizontally along the bottom of the nasal passage. With the user in this position, it is preferable that the outlet is angled so that a plane of the outlet is horizontal to the bottom wall of the nasal passage or angled forwardly towards the front wall of the nasal passage. Alternatively, the preferred angle of the nasal prong outlet may be described as follows. The nasal prong outlet is angled so that the general plane of the nasal prong outlet is approximately parallel to the bottom of the user's nasal passage or angled forwardly towards the front wall of the user's nasal passage in use. Yet another way of describing the preferred angle of the nasal prong outlet is that the outlet is angled so that it is not visible when the prong is viewed from the rear and along a line parallel to where the bottom of the nasal passage would relative to the nasal prong in use.

The outlet may be formed as a planar outlet across the nasal prong perpendicular to the longitudinal axis of the prong at the tip of the prong. In this case, the correct angle of the outlet is achieved by a nasal prong angled so that the longitudinal axis of the prong at the tip of the prong is perpendicular to the bottom wall of the nasal passage or angled forwardly towards the front wall of the nasal passage. In this arrangement, the nasal prong outlet is not visible when the prong is viewed from the rear and along a line of the bottom of the nasal passage.

In other arrangements the nasal prong outlet maybe angled relative to the longitudinal axis of the prong. In this form the prong may extend rearwards in the user's nasal passage to generally follow the nasal passage. In this case the outlet of the prong would be formed at an angle sufficiently far from perpendicular to the axis of the prong, so that the outlet is angled to be parallel to the bottom wall of the nasal passage or face the front wall of the nasal passage. Again the outlet is angled so that the outlet is not visible when the prong is viewed from the rear and along a line of the bottom of the nasal passage. A person skilled in the art will understand there are many different combinations of prong angle and corresponding outlet angle that can be used to achieve an outlet that is parallel to the bottom surface of the nasal passage or angled forwardly towards the front wall of the nasal passage.

Figure 12:
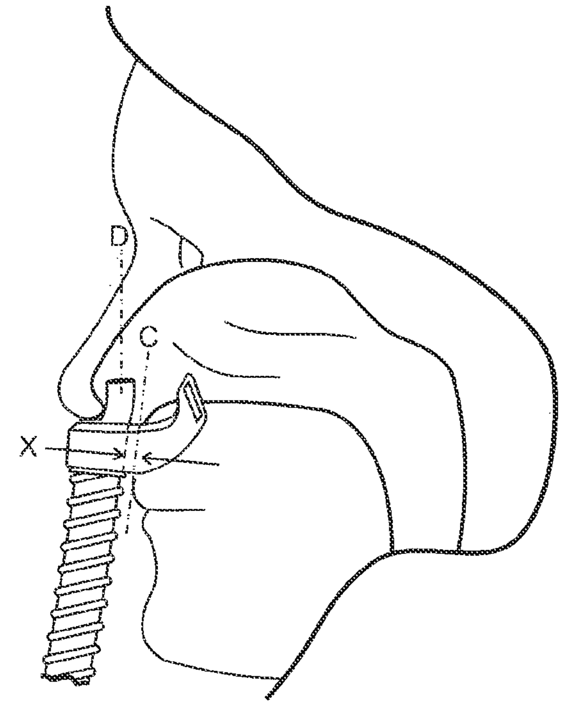
FIG. 12 is a view of a nasal cannula positioned on a user's face, the nasal cannula comprising a face contacting area to position the nasal prongs forwardly in the user's nostrils according to another embodiment of the present invention.

To facilitate the correct orientation of the nasal prong or nasal prong outlet in the nasal passage, the cannula has a face contacting area 70 (FIG. 7) that rests against a region of the user's face or nose to set the position of the prongs within the user's nostrils. For example in a preferred embodiment the area contacts the user's upper lip region. In use the head gear pulls the cannula against the user's upper lip to position the cannula correctly. A plane of the face contacting area in contact with the user's upper lip region is indicated by the dashed line C in FIG. 7 and FIG. 12. The nasal prong is angled or curved so that a longitudinal axis D (FIG. 12) of the nasal prong at the tip of the nasal prong is parallel to or angled forwardly in the user's nose to direct the flow of gases towards the front wall of the nasal passage. In the illustrated embodiment the nasal prong is angled or curved so that a longitudinal axis D is parallel to or angled forward of the plane of an area of a cannula body in contact with the user's upper lip region.

With the face contacting area sitting flat against the user's upper lip region, the angle of the prong is set correctly to ensure inspiratory air is directed towards the front of the nasal passage. Preferably the nasal prong is curved with a centre of curvature towards the front of the user's nose so that the prong curves towards the front of the nasal passage. The curve of the nasal prong may not be circular, for example, there may be more than one centre of curvature about which the prong is curved. Alternatively the nasal prong is straight. For example the prong may be straight with a longitudinal axis parallel to or angled forward relative to the plane of a cannula body in contact with the users upper lip region.

In one embodiment, the longitudinal axis of the prong at the tip of the prong is preferably angled at least 10° forward of the plane of the area contact with the user's upper lip region.

An area of the cannula may contact other areas of the user's face. For example the cannula may rest on the cheeks of the user, this contact with the user's cheeks setting the angle of the prongs in the user's nasal passages correctly. In an alternative but preferred embodiment, the cannula contacts the junction between the user's upper lip region and the user's septum, in use the head gear pulls the cannula against this junction to position the nasal prongs correctly.

With the face contacting area sitting flat against the user's upper lip region or other region of the user's face or nose, the prong is spaced correctly towards the front of the nostril, creating a gap at the rear of the nasal passage for the expiratory gases to exit the nostril. In the illustrated embodiment of FIG. 12, a rear extent of the nasal prong is spaced forwardly of the area of a cannula body in contact with the user's upper lip region by a distance X.

The part of the cannula in contact with the user's face or nose is preferably made from a pliable, flexible, resilient material. However, the cannula preferably does not easily collapse in the region between the users face or nose (e.g. the upper lip area) and the rear extent of the nasal prong. This may be achieved by having a solid cross section between the rear extent of the nasal prong and the area of the cannula in contact with the user's face or nose. For example, the hollow manifold of the cannula body does not extend significantly rearward of the rear extent of the nasal prong.

Figure 13:
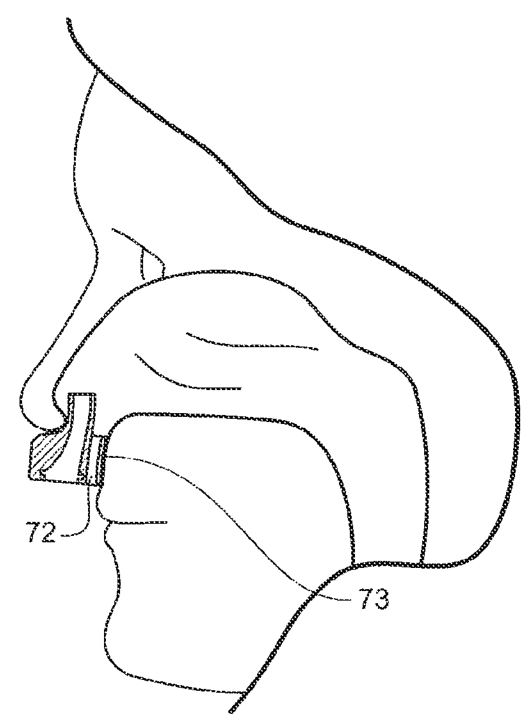
FIG. 13 is a view of a nasal cannula positioned on a user's face for use, the nasal cannula comprising an expiratory gases flow path according to another embodiment of the present invention.
Figure 14:
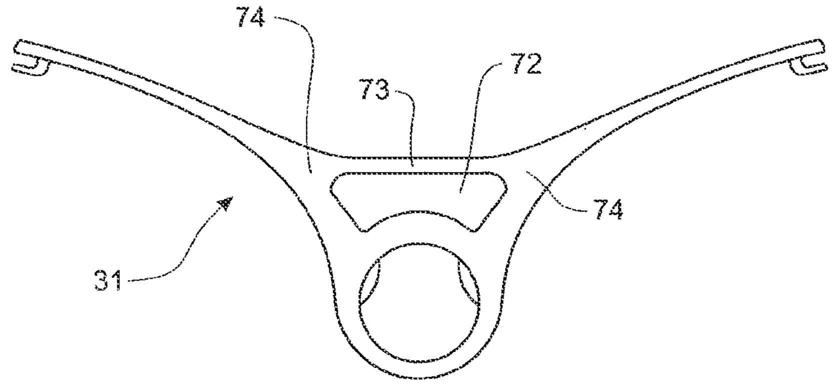
FIG. 14 is a bottom view of an example nasal cannula comprising an expiratory gases flow path according to another embodiment of the present invention.

In a further embodiment, the nasal cannula may include an expiratory flow path between the manifold and an area of the cannula body in contact with the user's upper lip region. As shown in FIG. 13, expiratory flow path or channel 72 is provided. A stand off or bridge portion 73 is provided to rest against a user's upper lip region to set the nasal prongs a distance away from the user's upper lip region. The space or channel 72 between the manifold and the bridge portion allows exhaled gases to pass via the channel and exit below the cannula. The channel is illustrated in FIG. 14 as having an elongated cross section, the channel cross section extending across the user's upper lip region in use. However, the channel may be a circular hole or holes provided through the cannula body towards a rear surface of the cannula body.

The bridge portion 73 may be integrally formed with the cannula body, for example from a pliable, resilient, flexible material. The bridge portion may act substantially as a leaf spring that bends about the connection points 74 that connect the bridge portion 73 to the remainder of the cannula body 31 of the cannula 30. Preferably the bridge portion and connection points 74 provide enough resiliency to ensure the channel does not close up with the bridge portion collapsing towards the manifold due to tension provided by the head gear straps. Satisfactory resiliency can be achieved by choosing a suitable cross section for the channel.

Figure 15:
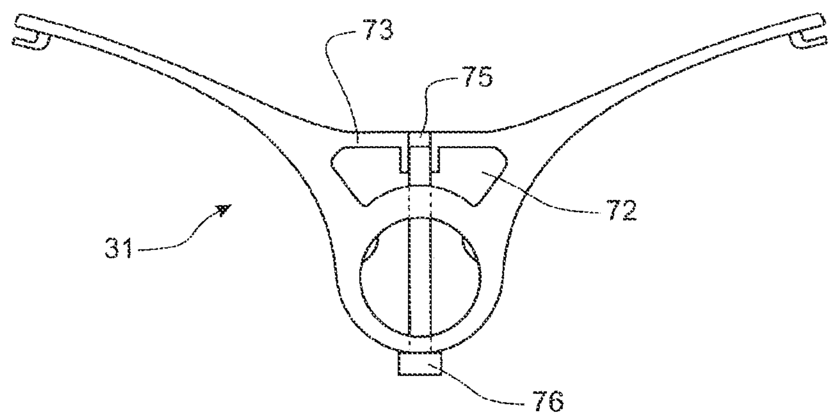
FIG. 15 is a bottom view of a nasal cannula according to another embodiment of the present invention comprising an adjustable expiratory gases flow path and providing adjustable prong positioning relative to the user's upper lip region.

In a further embodiment, the cross section of the channel may be adjustable to suit a particular user. For example, as shown in FIG. 15 the bridge portion comprises a threaded socket 75. The cannula further comprises a screw 76 engaged with threaded socket 75. Turning the screw in the socket adjusts the cross section of the channel and also the distance the nasal prongs are spaced from the user's upper lip. The distance between the bridge portion and the nasal prongs can be adjusted to suit a particular user to set the nasal prongs at the front of that user's nostrils.

Another benefit of the bridge portion is the manifold is spaced from the user's upper lip. When providing heated gases to a user, heat from the gases can be transferred via conduction through the cannula material to the user's upper lip region. This heat can cause the user's upper lip region to perspire which can be uncomfortable for the user. The bridge portion helps to insulate the user's upper lip region from the warm gases by providing an air gap between the manifold and the lip region.

Figure 16:
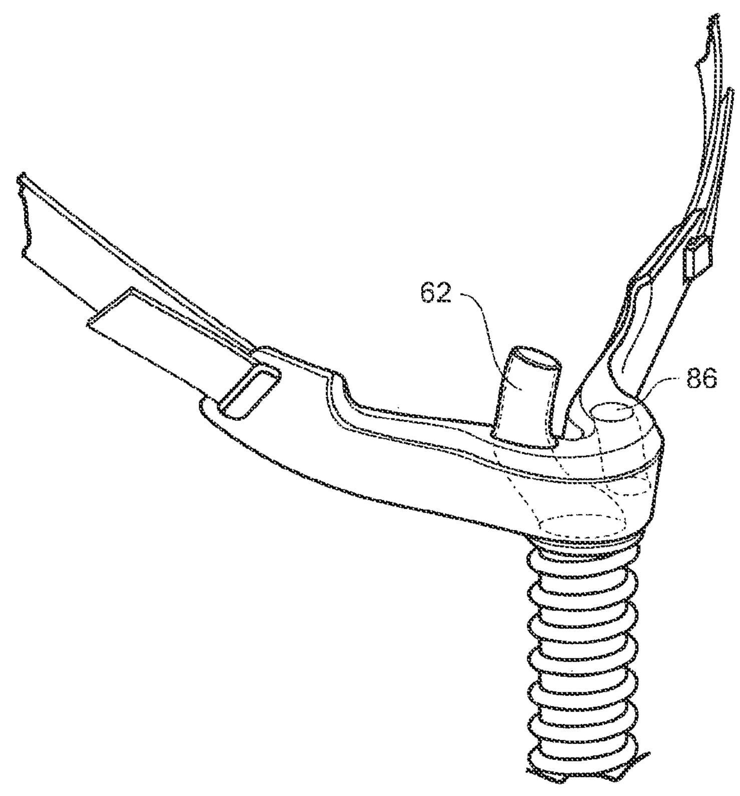
FIG. 16 is a perspective view of a nasal cannula comprising a single nasal prong and an expiratory gases flow path according to another embodiment of the present invention.

An alternative embodiment nasal cannula comprises a single nasal prong only. An example is illustrated in FIG. 16. In use, the single prong interfaces with a corresponding nostril of a user. The user therefore has a vacant nostril through which expired air may pass without interfering with the inspiratory gases. Such an arrangement may result in reduced noise during use. Furthermore, the cannula may include a path way or channel 86 to be aligned with the vacant nostril in use for the exhaled gases to flow through.

Figures 26A, 26B:
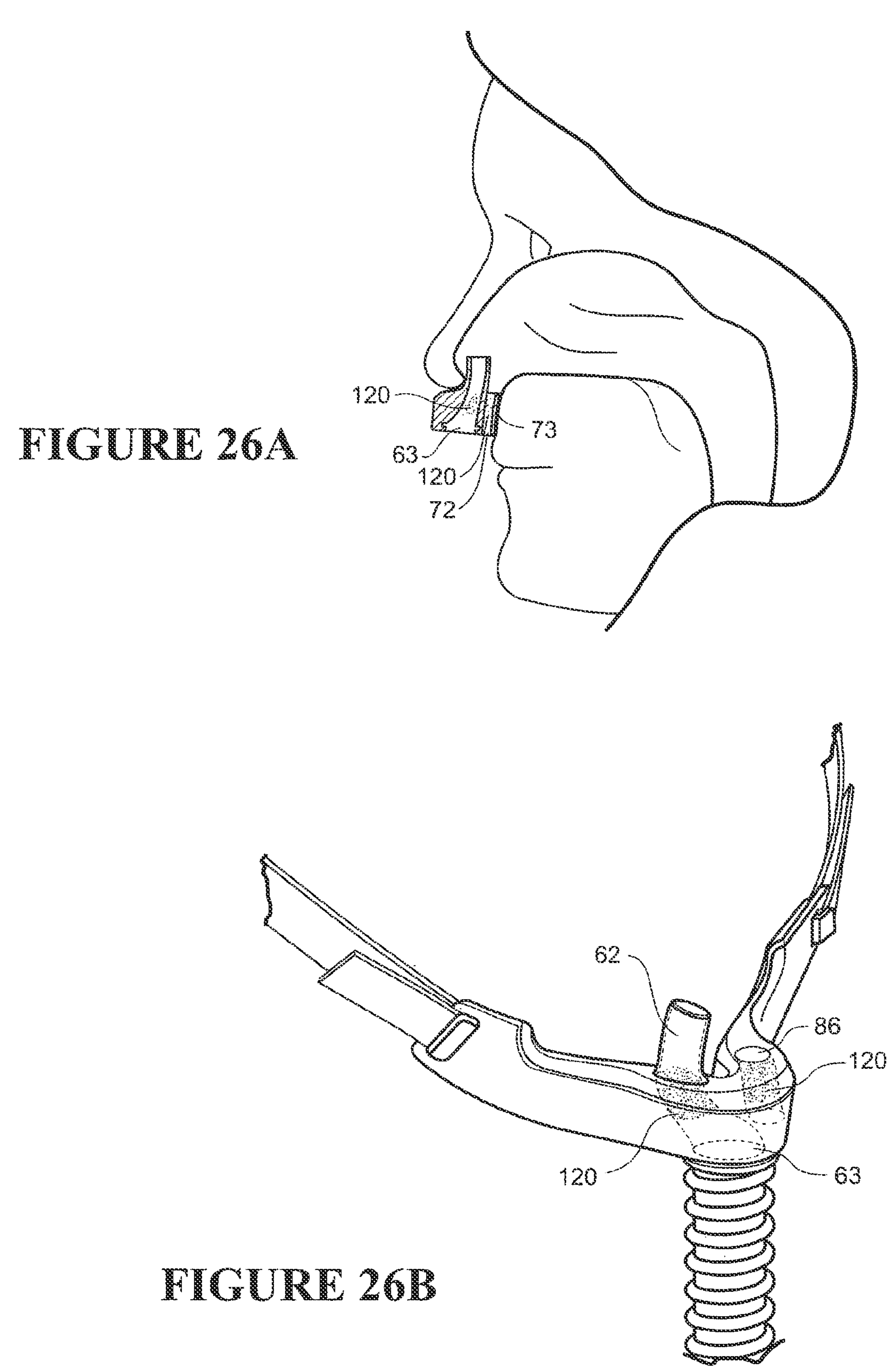
FIGS. 26A and 26B are the nasal cannulas of FIGS. 13 and 16 comprising noise suppression material in the inspiratory and expiratory gases flow paths according to another embodiment of the present invention.

A noise suppression media may be utilised to suppress noise created by the inspiratory gases or expiratory gases in the nasal passages or cannula, or noise transmitted through the pathway from the gases source unit. For example, as shown in FIGS. 26A and 26B, a noise suppression media 120 may be utilised in the inlet 63 or manifold of the cannula, or in the expiratory gases channels 72, 86, or in both the inspiratory and expiratory flow paths 63, 72, 86. The noise suppression media may be a filter type material of low density that attenuates sound but avoids restriction of the gases flow.

Figure 25A:
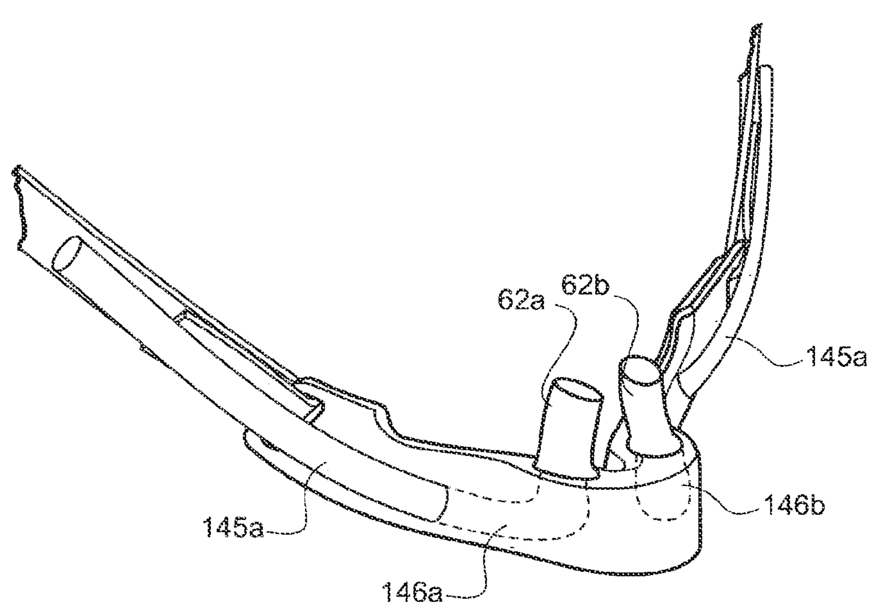
FIGS. 25A and 25B are alternative forms of nasal cannula comprising lumen in a side arm of the cannula according to another embodiment of the present invention.
Figure 25B:
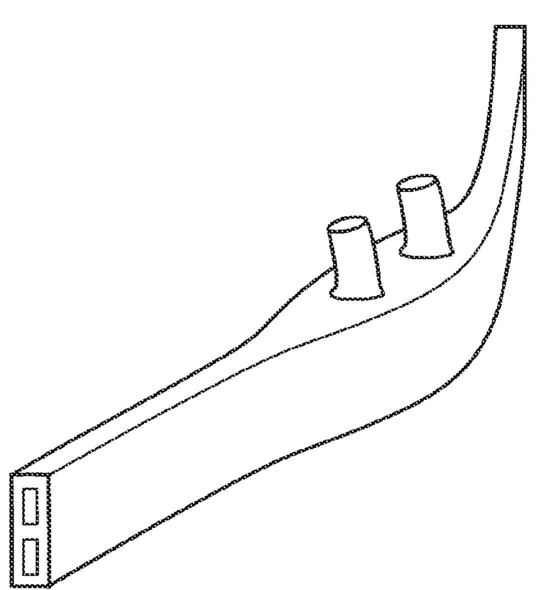

In a further alternative embodiment, a conduit providing a flow of gases to the cannula may communicate with a nasal prong or prongs via a connection in a side arm. For example, as shown in FIG. 25B, a conduit 145*a* connects to lumen 146*a* in side arm 65*a* of the cannula. The side arm lumen 146*a* communicates with a nasal prong 62*a*, connecting the conduit 145*a* to the nasal prong 62*a*. The gases flow passage provided by the conduit 145*a*, lumen 146*a* and nasal prong 62*a* is mirrored on the other side of the cannula by conduit 145*b*, lumen 146*b* in side arm 65*b*, and nasal prong 62*b*. Conduits 145*a* and 145*b* preferably connect to a common conduit, the common conduit connected to a gases source for example by a Y connection attached to headgear supporting the cannula.

Alternatively a conduit may be provided to one side of the nasal cannula only, connecting with a side arm lumen that communicates with both a left and right nasal prong. The side arm may comprise a single lumen communicating with both nasal prongs. Alternatively the side arm may comprise a multi-lumen. For example the side arm may comprise a double lumen, one lumen per nasal prong, as shown in FIG. 25B.

Flow Restrictor

Another invention described herein relates to a flow restrictor incorporated in the air flow path between the gas source unit 15 and the patient. The flow restrictor may be incorporated into any suitable medical gases system that provides a gases stream from a gases source to a patient in use. However, it is described below by example for use in a system that provides a heated, humidified, gases stream to a patient or user.

The flow restrictor may be located in the air flow path at any position between the gas source unit and the patient. For example, the air flow restrictor may be located at an outlet end of the conduit 3, an inlet end of the secondary conduit 45, an outlet end of the secondary conduit 45, or a patient interface, for example a nasal interface comprising the nasal cannula assembly 30, or any other patient interface such as a nasal mask or a full face mask. By example only, the air flow restrictor 80 is shown in FIG. 17 in an inlet end of the secondary conduit 45.

In use, a patient using a gases supply system may restrict the gases flow by inadvertently squashing the conduit 3. For example, a patient may roll onto the conduit 3 during sleep, the patient's body squashing the cross section of the conduit thereby restricting the flow of gases provided to the patient. This situation is undesirable.

The air flow restrictor is provided to be a dominant flow restriction in the air flow system. The air flow restrictor will be the dominant flow restriction even when a portion of the conduit 3 is squashed or pinched. Typical conduits for use in medical gases systems are flexible in an axial direction, but are relatively stiff radially to prevent complete occlusion should the conduit be squashed or pinched by a user. With the cross section partially occluded, the flow restrictor remains the dominant flow restriction in the system. Therefore, even with the conduit 3 partially occluded, the flow received by the patient is not affected. Also, any variation in resistance to flow downstream of the flow restrictor does not affect the operation of the gases source unit, as the dominant flow restriction provided by restrictor 80 acts to decouple the system downstream of the flow restrictor from the system upstream of the flow restrictor. For example the effect on the gases source unit of the partial occlusion of a nasal prong or prongs is mitigated by the flow restrictor. In this case, it may be beneficial to locate the flow restrictor at an outlet of the gases source unit.

With the inclusion of the flow restrictor, to achieve a desired gases flow rate or pressure provided to a patient, the air pressure provided by the gases source unit is increased compared to the same or similar system without the flow restrictor. The increased gases source unit pressure overcomes the pressure drop across the flow restrictor to result in the desired flow or pressure at the patient. With partial occlusion of the conduit 3, the flow or pressure at the patient is not substantially affected.

The air flow restrictor may be a simple orifice plate or any other suitable localized restriction in the system. For example, the restrictor may comprise a small diameter cylinder mounted in-line between the cannula and conduit 3, the air flow passing through and being restricted by the small diameter cylinder. Alternatively and by example only, the restriction could be a cylinder with a disc located coaxially within the cylinder, the disc supported by a spoke or spokes extending from an internal surface of the cylinder. In the preferred embodiment, the flow restrictor comprises a gradually reducing cross section. Air flow passing through a sudden restriction such as an orifice in a plate can create significant noise which is undesirable. Air passing through a gradually reducing cross section is quieter by comparison. For example, as shown in FIG. 17, the restriction comprises a bullet or approximate ogive shaped piece 81 mounted coaxially within a cylinder 82 and supported by spokes 83 extending from an inner surface of the cylinder, the tip of the bullet or approximate ogive shaped piece facing into the flow of gases. The restrictor provides a substantially annular cross section between an outer surface of the bullet shape and the inner surface of the cylinder, the spokes extending across the annular cross section, the area of the annular cross section decreasing in an axial direction along the restrictor in the direction of the flow. Alternatively the restrictor is a cone mounted on spokes coaxially within a cylinder.

Alternatively the restrictor is trumpet shaped, the cross section of the restrictor being circular and decreasing in an axial direction along the restrictor in the direction of the flow.

Preferably the spokes of the restrictor of FIGS. 17 to 19 extend longitudinally in an axial direction. Longitudinal spokes help maintain a laminar flow to reduce noise created by the air flow passing through the restrictor.

By example, the preferred embodiment comprises a cylinder with an internal diameter of approximately 10 mm, and a bullet shaped member of approximately 7.5 mm outside diameter. This restrictor is suitable for use with a 30 cm lone secondary tube having an internal diameter of 10 mm and a 1.5 m-1.8 m long conduit having an internal diameter of approximately 11 mm.

Without the flow restrictor placed in the system, the gases source unit or blower is set to provide gases at a pressure equal to the pressure expected at the patient interface. When the flow restrictor is placed in the system, the blower pressure is offset by a predetermined amount above the pressure expected at the patient interface to account for the pressure drop across the restrictor.

The preferred system includes a selectable function for indicating to the system controller 18 that the flow restrictor is incorporated into the system. For example, controller 18 is configured to receive an input selectable by a user, for example by a push button on the blower unit. Where the restrictor is used, the user sets the input to indicate to the controller the flow restrictor is in place. In response to receiving the input, the controller automatically adds an offset to the pressure provided by the blower unit. The blower unit display 13 does not display the actual pressure provided by the blower, but displays the pressure expected downstream of the restrictor.

The restrictor may be a standalone item that may be retrofitted to an existing system. For example, the restrictor may be fitted to an inlet of a patient interface such as the cannula assembly 30, or to either end of the secondary conduit or the outlet end of conduit 3. For example, an inlet end of the restrictor comprises an external diameter 84 matched to interface with an internal diameter of the outlet of the conduit 3. An outlet end of the restrictor comprises an internal diameter 85 matched to interface with an internal diameter of the inlet of the secondary conduit 45. Alternatively, the restrictor may be integrally formed with any one of the conduit 3, secondary conduit 45 or a patient interface. The restrictor may be integrally formed with or attached to any type of patient interface, for example a nasal cannula, face mask, nasal mask or any other patient interface known in the art.

Plastic Deformable Inserts for Holding Cannula Shape

The cannula body described earlier may further comprise at least one plastically deformable member. For example, the cannula body may be integrally formed with a metal wire 90 as indicated in FIG. 20. The metal wire has a low yield strength (low elastic limit) so that it can be easily deformed plastically. The yield strength of the plastically deformable member is significantly lower than the yield strength of the flexible, resilient, pliable material from which the cannula body is made. The cannula body will deform elastically at high strain, whereas the plastically deformable member will deform plastically at low strain. Whereas the cannula body material can be bent doubled over on itself without noticeable plastic deformation, the plastically deformable material requires only a small amount of bending to reach the elastic to plastic limit.

Once plastically deformed the metal wire holds its deformed shape. Therefore the inclusion of the metal wire gives the resilient, flexible, pliable cannula body a shape memory allowing the cannula body to hold its shape once bent, twisted or otherwise formed to match a user's facial profile.

For example, the cannula body may include one or more wires 91 formed in the wall of each nasal prong. In use a patient or other person may manipulate the orientation of each prong to fit the nasal prongs to the patient's nasal passages in a comfortable way. Once manipulated to the desired orientation, the wire will retain the position of the prongs. The cannula body may comprise a wire or other plastically deformable member that extend across the users upper lip region, from one corner of the mouth to the other corner of the mouth. This plastically deformable member can be bent or otherwise manipulated to match the curve of the users upper lip region. The plastically deformable member may be a wire or strap 92 of material or other shape suitable for integrating with the cannula body. The plastically deformable material is preferably a metal with a low elastic to plastic limit. For example the plastic deformable member may be copper, aluminium or other ductile material.

Rolling Diaphragm

Patient interfaces such as cannula assemblies, nasal masks and full face masks are designed to fit a range of different users. However a small number of users may fall outside the typical design range. For such a user, a particular patient interface may not provide an optimal fit. For example, during use a nasal prong may touch or press against a wall of the user's nasal passage. This may cause discomfort over an extended period of use and can result in user non-compliance with a prescribed treatment regime. A very thin walled nasal prong may be utilised so that little pressure against the wall of the nasal passage results should there be contact between the nasal passage wall and nasal prong. However, should a thin walled nasal prong press against the wall of the nasal passage, the cross sectional area of the prong can be partially occluded easily. This causes an increase in air flow which can also cause discomfort and also result in excessive noise.

To help alleviate one or more of the aforementioned problems, an improved nasal cannula comprises a thin section of material between the root of the nasal prong and the surface from which the prong extends. The thin section has a thickness less than the thickness of the wall of the nasal prong. The improvement comprises a cannula with a manifold having a thin membrane in a wall of the manifold and a nasal prong extending from the thin membrane. The thin membrane has a thickness less than the thickness of the wall of the nasal prong. For example as shown in FIG. 21A a wall of the manifold comprises a thin annular membrane 111 surrounding the root of the nasal prong, the prong extending from the thin annular membrane,. Alternatively, the whole wall of the manifold from which the prong extends has a thickness less than the thickness of the wall of the nasal prong. For example, the nasal cannula described previously comprises a nasal prong or pair of nasal prongs extending from an upper surface of a manifold. The upper wall of the manifold could be a thin membrane from which two nasal prongs extend.

The thin membrane provides a weak point at or near the root of the nasal prong. When a lateral force is provided to a side of the nasal prong, for example at a tip of the nasal prong, the nasal prong is deflected laterally by bending at the root of the nasal prong. The cross sectional area of the nasal prong is not significantly affected, as the thickness of the prong wall provides sufficient strength compared to the thin membrane such that the prong retains its shape. Therefore the flow rate of gases exiting the nasal prong remains substantially the same, while pressure against the wall of the nasal passage is minimal.

Preferably the thin membrane 111 is an annulus around the root of the prong, the prong extending from the annulus. With reference to FIGS. 21B to 21E, preferably a radial length of the annular membrane is longer than the radial distance from an inner circumferential perimeter 112 to an outer circumferential perimeter 113 of the membrane. The wall of the nasal prong extends from the inner circumferential perimeter. For example the thin membrane may be shaped to be approximately a fraction of a torus. A torus is formed by rotating a closed first curve, for example a circle, about a line in its plane but not intersecting it. By a fraction of a torus we mean the torus is truncated on a plane approximately perpendicular to the line. For example, a half torus is a torus truncated through the centre of the closed first curve.

The wall of the prong extends from the inner circumferential perimeter 112 of the fraction of torus and the wall of the manifold extends from the outer circumferential perimeter 113 of the fraction of torus. Preferably the wall of the prong extends from the inner circumferential perimeter with the inside of the first curve facing the tip of the prong. Preferably the first curve is a circle and the wall of the prong extends approximately perpendicularly to a radius of the first curve. Preferably the first curve is a circle and the wall of the manifold extends approximately parallel to a radius of the first curve.

Alternatively, the thin membrane 111 may be approximately a fraction of a sphere formed by truncating a sphere on a first plane and a second plane, the inner circumferential perimeter being on the first plane and the outer circumferential perimeter being on the second plane. For example, the thin membrane is approximately hemispherical as shown in FIG. 21C, the second plane being approximately through the centre of the sphere. Preferably the prong extends from a convex side of the membrane. Other alternative shapes for the thin membrane are shown in FIGS. 21D and 21E.

With the radial length of the thin membrane 111 being longer than the radial distance from the inner circumferential perimeter 112 to the outer circumferential perimeter 113, the thin membrane acts as a diaphragm, and allows the root of the nasal prong to roll or pivot. This allows the prong to move laterally with respect to the longitudinal axis of the nasal prong. The flexibility of movement provided by the thin membrane allows a thicker walled nasal prong to be utilised without reducing comfort of fit in the user's nasal passage. The thicker walled nasal prong retains its cross sectional shape when a sideways or lateral force is exerted to the prong, for example by a contacting nasal passage side wall.

Truncated Tips

As discussed previously, the preferred cannula comprises nasal prongs that are biased or arranged towards the front of the nasal passage. The length of the nasal prongs is selected by the cannula designer to ensure the tip of the prong does not contact the wall of the nasal passage. Contact with the nasal passage may cause discomfort to the user. Ideally the length of the prong is sufficiently long enough to direct the flow of gases in a desired direction. For example, the length of the prong is sufficiently long enough to direct the flow of gases towards the front of the nasal passage, to reduce the amount of flow collision with expiratory gases as explained earlier. Therefore it is desirable to have nasal prongs with sufficient length to direct the flow of gases in a desired direction, while avoiding contact with the wall of the nasal passage.

Figure 22A:
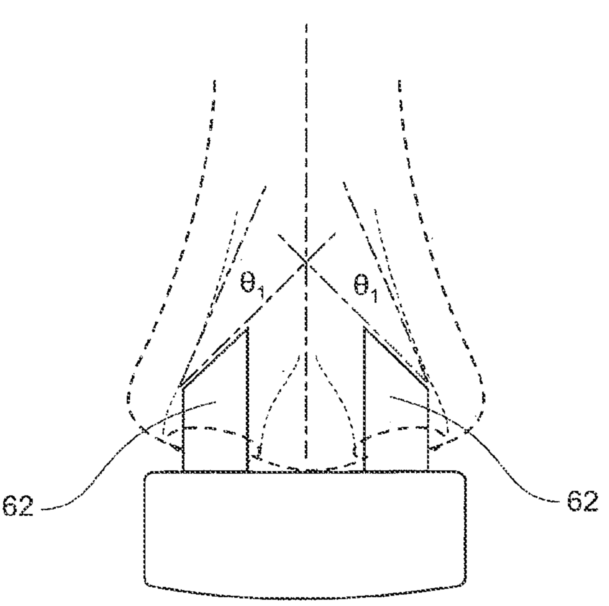
FIGS. 22A and 22B are views of a nasal cannula comprising nasal prongs with tips angled to match the angle of a user's nasal passage walls according to another embodiment of the present invention.
Figure 22B:
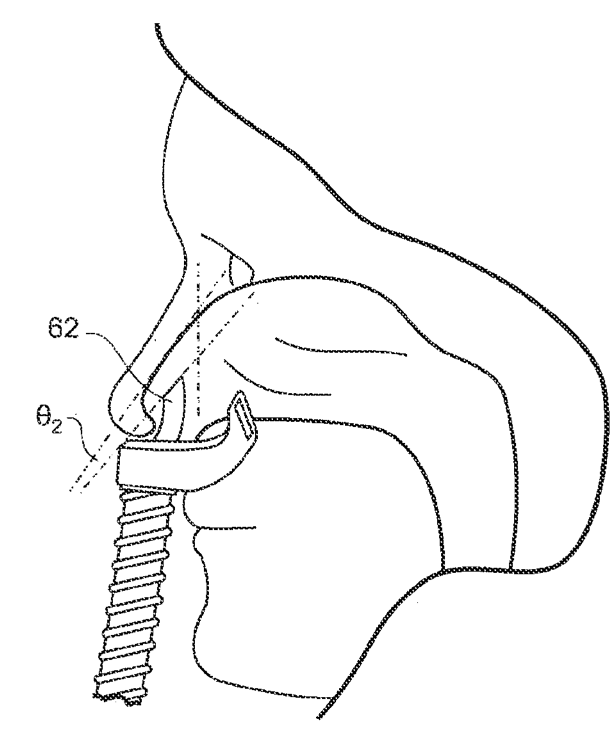

In the preferred cannula, to assist with directing the flow of gases while avoiding contact with the wall of the nasal passage, the tip of each nasal prong is truncated to match the angle of the nasal passage side walls. As shown in FIG. 22A, when viewed from the front, the tip of each nasal prong is angled downwards from a centreline of the nose. For example, the angle $\theta_1$ between the nasal passage side wall and the tip of the nasal prong is less than 30°. Preferably the angle between the nasal passage side wall and the tip of the nasal prong is less than 20°. Similarly, when viewed from a side of the nose as shown in FIG. 22B, the tip of the nasal prong is angled forwardly. For example, the angle $\theta_2$ between the front of the nasal passage wall and the tip of the nasal prong is less than 20°. Preferably the angle between the nasal passage side wall and the tip of the nasal prong is less than 10°.

The foregoing description of the invention includes preferred forms thereof. Modifications may be made thereto without departing from the scope of the invention as defined by the accompanying claims.

What is claimed is:

1. A cannula assembly for providing a flow of respiratory gases to a user, comprising:
- a cannula body that is resilient and flexible and configured to contact a user's upper lip region in use, the cannula body comprising:
  - at least one nasal prong configured to extend into a user's nostril in use, but not sealing to the user's nostril; and
  - a manifold comprising an inlet for receiving a conduit, the inlet being fluidly connected to the at least one nasal prong;
- a frame that is at least semi-rigid and provides support to the cannula assembly, the frame comprising a first frame side arm and a second frame side arm extending from a central portion, the first frame side arm and the second frame side arm configured to be positioned along opposing sides of a user's face, the first frame side arm and the second frame side arm configured to attach the cannula assembly to a headgear;
- wherein the cannula body is positioned between the frame and the user's face in use;
- wherein a portion of the cannula body is configured to be bent to be doubled over on itself substantially without plastic deformation, and the frame is capable of elastic deflection;
- wherein the frame has a first projection configured to engage the conduit, to secure the conduit to the frame; and
- wherein the cannula body further comprises a first cannula body side arm and a second cannula body side arm extending from a respective one of opposing sides of a central portion of the cannula body, wherein at least a portion of each of the first cannula body side arm and the second cannula body side arm extends along each of the respective one of the first frame side arm and the second frame side arm at least to a connection configured to attach the headgear to the frame.

2. The cannula assembly of claim 1, wherein each of the first frame side arm and the second frame side arm is angled backwards from the central portion towards the user's face in use.

3. The cannula assembly of claim 1, wherein each frame side arm is angled upwards from the central portion so that the first frame side arm and the second frame side arm each are configured to extend on a line that passes near a top of each ear of the user in use.

4. The cannula assembly of claim 1, wherein a distal end of each of the first frame side arm and the second frame side arm is provided with a connection for attachment to a headgear for holding the cannula assembly in place on the user's face.

5. The cannula assembly of claim 1, wherein the first cannula body side arm and the second cannula body side arm and is configured in use to pass across a user's upper lip region to terminate adjacent a corresponding cheek region, and wherein a portion of each of the first cannula body side arm and the second cannula body side arm is configured to rest in between a user's face and one of the first frame side arm and the second frame side arm in use.

6. The cannula assembly of claim 1, wherein one or both of the first frame side arm and the second frame side arm is provided with a quick release connector to attach or disconnect the headgear to or from the cannula assembly.

7. The cannula assembly of claim 1, wherein the frame comprises a material that has a higher stiffness compared to the cannula body or the cannula body comprises a material that has a lesser stiffness than the material of the frame.

8. The cannula assembly of claim 1, wherein the frame has a higher Youngs Modulus compared to the cannula body.

9. The cannula assembly of claim 1, wherein the frame is formed from a polycarbonate plastic or a polypropylene plastic material.

10. The cannula assembly of claim 1, wherein the cannula body comprises a material with a Shore A hardness of between 10 and 60.

11. The cannula assembly of claim 1, wherein the cannula body is overmoulded to the frame.

12. The cannula assembly of claim 1, wherein the cannula body is made from silicone.

13. The cannula assembly of claim 1, wherein, wherein a height of at least a portion of each of the first cannula body side arm and the second cannula body side arm is at least as great as a corresponding height of a respective one of the first frame side arm and the second frame side arm of the frame.

14. The cannula assembly of claim 1, wherein the frame comprises a second projection for engaging the cannula body to removably secure the cannula body to the frame thereby securing the conduit relative to the cannula body.

15. The cannula assembly of claim 14, wherein the cannula body comprises a recess for receiving the second projection and/or wherein the second projection is a second flange substantially perpendicular to a longitudinal axis of the conduit, and the recess is a corresponding slot for receiving the second flange.

16. The cannula assembly of claim 1, wherein the first projection is a first flange configured to be substantially perpendicular to a longitudinal axis of the conduit and to engage about a circumference of the conduit near an end of the conduit, the first flange having a hole having an opening on one side for receiving the conduit, a diameter of the hole being corresponding to an external diameter of the circumference, a width of the opening being less than the external diameter of the circumference, in use the frame being elastically deformed during attachment to the conduit.

17. The cannula assembly of claim 16, wherein the inlet of the cannula body is an aperture configured to receive the end of the conduit, wherein in use a rim around the aperture is sandwiched between the first flange and a surface extending radially from the conduit adjacent the circumference, sealingly engaging the inlet to the conduit, and wherein the cannula body has an annular groove extending about the aperture for receiving the surface extending radially from the conduit.

18. The cannula assembly of claim 16, further comprising the conduit, the conduit having a first radially extending surface and a second radially extending surface, the first flange engaging the conduit about a circumference between the first radially extending surface and the second radially extending surface, the first flange being captured in a direction along an axis of the conduit between the first radially extending surface and the second radially extending surface.

19. A nasal cannula assembly for providing a flow of respiratory gases to a user comprising:

- a cannula body that is resilient and flexible, the cannula body comprising:
  - two nasal prongs extending from the cannula body, and
  - an inlet for receiving a conduit, the inlet being fluidly connected to the two nasal prongs;
- a frame comprising a first side arm and a second side arm extending from a central portion of the frame, the first side arm and second side arm extending in opposing directions from a central portion of the frame, wherein the frame is at least semi rigid and provides support to the nasal cannula assembly, the first side arm and the second side arm configured to attach the nasal cannula assembly to a headgear;
- wherein the cannula body is pliable;
- wherein the cannula body can be elastically deformed easily without noticeable plastic deformation, each of the first side arm and the second side arm is angled upwards from the central portion of the cannula body;
- wherein a frame material has a higher stiffness compared to a cannula body material;
- wherein the cannula body is removably attached to the frame, the frame comprising a first projection configured to engage the conduit to secure the conduit to the frame, wherein the first projection is a flange that engages a conduit connector; and
- wherein the first projection is a first flange configured to be substantially perpendicular to a longitudinal axis of the conduit and to engage about a circumference of the conduit near an end of the conduit, the first flange having a hole having an opening on one side for receiving the conduit, a diameter of the hole being corresponding to an external diameter of the circumference, a width of the opening being less than the external diameter of the circumference, in use the frame being elastically deformed during attachment to the conduit.

20. A nasal cannula assembly for providing a flow of respiratory gases to a user comprising:

- a cannula body configured to contact a user's upper lip region, the cannula body comprising:
  - a pair of nasal prongs extending from the cannula body, and
  - an inlet for receiving a conduit, the inlet being fluidly connected to the pair of nasal prongs;

a frame integrally moulded with the cannula body, wherein the frame comprises a material that has a higher stiffness compared to the cannula body;

a first side arm and a second side arm extending outwardly in opposing directions from a central portion of the frame, wherein the first side arm and the second side arm are configured to be positioned along opposing sides of a user's face, wherein each of the first side arm and second side arm is angled backwards from the central portion towards the user's face in use, wherein a distal end of each of the first side arm and the second side arm is provided with a quick release connector to attach or disconnect a headgear to or from the nasal cannula assembly; and wherein the inlet of the cannula body is an aperture configured to receive an end of the conduit, wherein in use a rim around the aperture is sandwiched between a first flange and a surface extending radially from the conduit adjacent a circumference, sealingly engaging the inlet to the conduit, and wherein the cannula body has an annular groove extending about the aperture for receiving the surface extending radially from the conduit.

* * * * *